(12) United States Patent
Siddiqui et al.

(10) Patent No.: US 7,553,864 B2
(45) Date of Patent: Jun. 30, 2009

(54) COMPOUNDS FOR THE TREATMENT OF INFLAMMATORY DISORDERS AND MICROBIAL DISEASES

(75) Inventors: M. Arshad Siddiqui, Newton, MA (US); Umar Faruk Mansoor, Framingham, MA (US); Panduranga Adulla P. Reddy, Walpole, MA (US); Vincent S. Madison, Mountain Lakes, NJ (US)

(73) Assignee: Schering Corporation, Kenilworth, NJ (US)

( * ) Notice: Subject to any disclaimer, the term of this patent is extended or adjusted under 35 U.S.C. 154(b) by 56 days.

(21) Appl. No.: 11/605,927

(22) Filed: Nov. 29, 2006

(65) Prior Publication Data

US 2007/0129378 A1    Jun. 7, 2007

Related U.S. Application Data

(60) Provisional application No. 60/741,264, filed on Dec. 1, 2005.

(51) Int. Cl.
  *A01N 43/36* (2006.01)
  *A61K 31/40* (2006.01)
  *C07D 295/00* (2006.01)
  *C07D 207/00* (2006.01)
(52) U.S. Cl. .................................. 514/408; 548/400
(58) Field of Classification Search ................ None
  See application file for complete search history.

(56) References Cited

U.S. PATENT DOCUMENTS

2006/0178366 A1    8/2006   Siddiqui et al.

FOREIGN PATENT DOCUMENTS

| WO | WO 02/102791   | 12/2002 |
|----|----------------|---------|
| WO | WO 2005/019194 | 3/2005  |
| WO | WO 2005/121130 | 12/2005 |

OTHER PUBLICATIONS

Vippagunta et al. Advanced Drug Delivery Reviews, 2001, 48, 3-26.*
International Search Report for International Application No. PCT/US2006/045739, mailed Mar. 29, 2007—5 pgs.

* cited by examiner

*Primary Examiner*—James O Wilson
*Assistant Examiner*—Noble Jarrell
(74) *Attorney, Agent, or Firm*—Krishna G. Banerjee

(57) ABSTRACT

This invention relates to compounds of the Formulae (I)-(IX):

formula (VI)
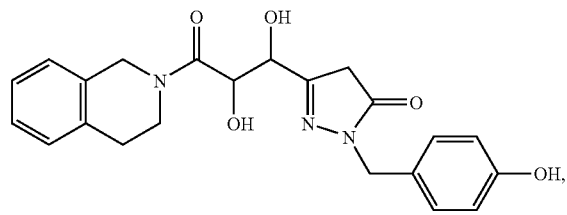
formula (VIII)
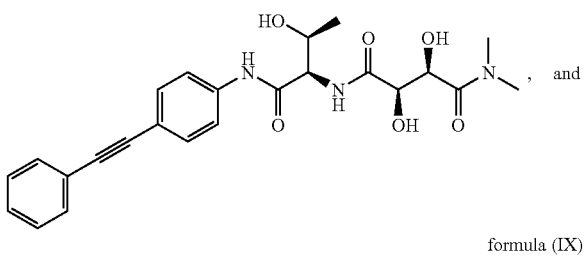
and
formula (VII)
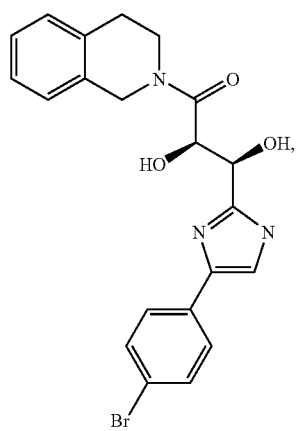
formula (IX)
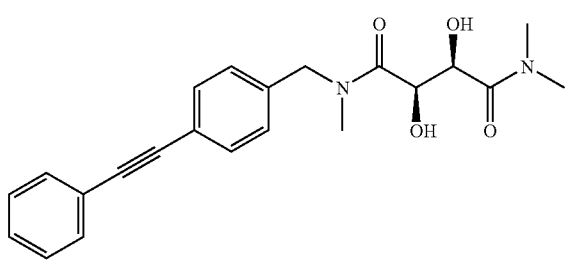
or a pharmaceutically acceptable salt, solvate, ester or isomer thereof, which can be useful for the treatment of diseases or conditions mediated by MMPs, aggrecanase, ADMP, LpxC, ADAMs, TACE, TNF-α or combinations thereof.
14 Claims, No Drawings

COMPOUNDS FOR THE TREATMENT OF INFLAMMATORY DISORDERS AND MICROBIAL DISEASES

This Application claims the benefit of U.S. Provisional Application Ser. No. 60/741,264, filed Dec. 1, 2005, which is incorporated herein by reference in its entirety.

BACKGROUND OF THE INVENTION

1. Field of the Invention

This invention relates generally to tartaric acid functional compounds that can inhibit matrix metalloproteinases (MMPs), a disintegrin and metalloproteases (ADAMs), aggrecanase or aggrecan degrading metallo protease (ADMP) and/or tumor necrosis factor alpha-converting enzyme (TACE) and in so doing prevent the release of tumor necrosis factor alpha (TNF-α), pharmaceutical compositions comprising such compounds, and methods of treatment using such compounds. The invention also relates to tartaric acid functional compounds that can inhibit UDP-3-O—(R-3-hydroxymyristoyl)-N-acetylglucosamine deacetylase (LpxC), and as a result have antimicrobiall activity.

2. Description

Osteo- and rheumatoid arthritis (OA and RA, respectively) are destructive diseases of articular cartilage characterized by localized erosion of the cartilage surface. Findings have shown that articular cartilage from the femoral heads of patients with OA, for example, had a reduced incorporation of radiolabeled sulfate over controls, suggesting that there must be an enhanced rate of cartilage degradation in OA (Mankin et al. J. Bone Joint Surg. 52A (1970) 424-434). There are four classes of protein degradative enzymes in mammalian cells: serine, cysteine, aspartic and metalloproteases. The available evidence supports the belief that it is the metalloproteases that are responsible for the degradation of the extracellular matrix of articullar cartilage in OA and RA. Increased activities of collagenases and stromelysin have been found in OA cartilage and the activity correlates with severity of the lesion (Mankin et al. Arthritis Rheum. 21, 1978, 761-766, Woessner et al. Arthritis Rheum. 26, 1983, 63-68 and Ibid. 27, 1984, 305-312). In addition, aggrecanase (a newly identified metalloprotease) has been identified that provides the specific cleavage product of proteoglycan, found in RA and OA patients (Lohmander L. S. et al. Arthritis Rheum. 36, 1993, 1214-22).

Metalloproteases (MPs) have been implicated as the key enzymes in the destruction of mammalian cartilage and bone. It can be expected that the pathogenesis of such diseases can be modified in a beneficial manner by the administration of MP inhibitors (see Wahl et al. Ann. Rep. Med. Chem. 25, 175-184, AP, San Diego, 1990).

MMPs are a family of over 20 different enzymes that are involved in a variety of biological processes important in the uncontrolled breakdown of connective tissue, including proteoglycan and collagen, leading to resorption of the extracellular matrix. This is a feature of many pathological conditions, such as RA and OA, corneal, epidermal or gastric ulceration; tumor metastasis or invasion; periodontal disease and bone disease. Normally these catabolic enzymes are tightly regulated at the level of their synthesis as well as at their level of extracellular activity through the action of specific inhibitors, such as alpha-2-macroglobulins and TIMPs (tissue inhibitor of MPs), which form inactive complexes with the MMP's.

Tumor necrosis factor alpha (TNF-α) is a cell-associated cytokine that is processed from a 26 kDa precursor form to a 17 kd active form. See Black R. A. "Tumor necrosis factor-alpha converting enzyme" Int J Biochem Cell Biol. 2002 January; 34(1):1-5 and Moss M L, White J M, Lambert M H, Andrews R C. "TACE and other ADAM proteases as targets for drug discovery" Drug Discov Today. 2001 Apr. 1; 6(8): 417-426, each of which is incorporated by reference herein.

TNF-α has been shown to play a pivotal role in immune and inflammatory responses. Inappropriate or over-expression of TNF-α is a hallmark of a number of diseases, including RA, Crohn's disease, multiple sclerosis, psoriasis and sepsis. Inhibition of TNF-α production has been shown to be beneficial in many preclinical models of inflammatory disease, making inhibition of TNF-α production or signaling an appealing target for the development of novel anti-inflammatory drugs.

TNF-α is a primary mediator in humans and animals of inflammation, fever and acute phase responses, similar to those observed during acute infection and shock. Excess TNF-α has been shown to be lethal. Blocking the effects of TNF-α with specific antibodies can be beneficial in a variety of conditions, including autoimmune diseases such as RA (Feldman et al, Lancet, (1994) 344, 1105), non-insulin dependent diabetes mellitus (Lohmander L. S. et al., Arthritis Rheum. 36 (1993) 1214-22) and Crohn's disease (Macdonald T. et al., Clin. Exp. Immunol. 81 (1990) 301).

Compounds that inhibit the production of TNF-α are therefore of therapeutic importance for the treatment of inflammatory disorders. Recently it has been shown that metalloproteases, such as TACE, are capable of converting TNF-α from its inactive to active form (Gearing et al Nature, 1994, 370, 555). Since excessive TNF-α production has been noted in several disease conditions also characterized by MMP-mediated tissue degradation, compounds which inhibit both MMPs and TNF-α production may also have a particular advantage in diseases where both mechanisms are involved.

One approach to inhibiting the harmful effects of TNF-α is to inhibit the enzyme, TACE before it can process TNF-α to its soluble form. TACE is a member of the ADAM family of type I membrane proteins and mediates the ectodomain shedding of various membrane-anchored signaling and adhesion proteins. TACE has become increasingly important in the study of several diseases, including inflammatory disease, because of its role in cleaving TNF-α from its "stalk" sequence and thus releasing the soluble form of the TNF-α protein (Black R. A. Int J Biochem Cell Biol. 2002 34,1-5).

Aggrecan is the major proteoglycan of cartilage and provides this tissue with its mechanical properties of compressibility and elasticity. In arthritic conditions one of the earliest changes observed in cartilage morphology is the depletion of aggrecan [Mankin et al. (1970) J. Bone Joint Surg. 52A, 424-434], which appears to be due to an increased rate of degradation.

The aggrecan molecule is composed of two N-terminal globular domains, G1 and G2, which are separated by an approximately 150 residue interglobular domain (IGD), followed by a long central glycosaminoglycan (GAG) attachment region and a C-terminal globular domain, G3 [Hardingham et al. (1992) in Articular Cartilage and Osteoarthritis: Aggrecan, The Chondroitin Sulfate/Keratan Sulfate Proteoglycan from Cartilage (Kuettner et al.) pp. 5-20, Raven Press, New York and Paulson et al. (1987) Biochem. J. 245, 763-7721. These aggrecan molecules interact through the GI domain with hyaluronic acid and a link protein to form large molecular weight aggregates which are trapped within the cartilage matrix [Hardingham et al. (1972) Biochim. Biophys. Acta 279, 401-405, Heinegard et al. (1974) J. Biol. Chem. 249, 4250-4256, and Hardingham, T. E. (1979) Biochem. J. 177, 237-247]. Loss of aggrecan from cartilage in arthritic conditions involves proteolytic cleavage of the aggrecan core protein within the IGD, producing a N-terminal G-1 fragment that remains bound to hyaluronic acid and the link protein within the matrix, releasing a large C-terminal GAG-containing aggrecan fragment that diffuses out of the cartilage matrix. Loss of the C-terminal fragment results in cartilage deficient in its mechanical properties. This deficiency arises because the GAGs which are present on the C-terminal portion of the aggrecan core protein are the components of aggrecan that impart the mechanical properties to the molecule through their high negative charge and water binding capacity.

Therefore compounds that exhibit inhibition against aggrecanase or aggrecan degrading metalloprotease (ADMP) could serve as potential therapeutic agents for treating aggrecanase-related disorders cited above, and are therefore desired.

Lipid A is the hydrophobic anchor of lipopolysaccharide (LPS) and forms the major lipid component of the outer monolayer of the outer membrane of gram-negative bacteria. Lipid A is required for bacterial growth and inhibition of its biosynthesis is lethal to the bacteria. Furthermore, blocking Lipid A biosynthesis increases the sensitivity of bacteria to other antibiotics.

One of the key enzymes of bacterial lipid A biosynthesis is LpxC. LpxC catalyzes the removal of the N-acetyl group of UDP-3-O—(R-3-hydroxymyristoyl)-N-acetylglucosamine. The LpxC enzyme is essential in gram negative bacteria for the biosynthesis of Lipid A, and it is notably absent from mammalian genomes. Since LpxC is essential for Lipid A biosynthesis and inhibition of Lipid A biosynthesis is lethal to bacteria, inhibitors of LpxC have utility as antibiotics. In addition, the absence of LpxC from mammalian genomes reduces potential toxicity of LpxC inhibitors in mammals. Accordingly, LpxC is an attractive target for antibacterial drug discovery.

There are several patents which disclose hydroxamate, carboxylate and/or lactam based MMP inhibitors.

U.S. Pat. No. 6,677,355 and U.S. Pat. No. 6,534,491(B2), describe compounds that are hydroxamic acid derivatives and MMP inhibitors.

U.S. Pat. No. 6,495,565 discloses lactam derivatives that are potential inhibitors of matrix metalloproteases and/or TNF-α.

U.S. patent application Ser. No. 11/142601 (filed Jun. 1, 2005) discloses tartrate compounds that are useful TACE inhibitors.

U.S. Pat. No. 5,925,659 teaches that certain heterocyclic hydroxamate compounds, in particular oxazoline compounds, have the ability to inhibit LpxC.

WO2004/00744 refers to N-Hydroxyamide derivatives having LpxC inhibitory activity and thus possessing antibacterial activity.

WO2004/062601 also refers to small molecule inhibitors of LpxC.

There is a need in the art for inhibitors of MMPs, ADAMs, aggrecanase, ADMP, TACE, and TNF-α, which can be useful as anti-inflammatory compounds and cartilage protecting therapeutics. The inhibition of TNF-α, ADMP, TACE and or other MMPs can prevent the degradation of cartilage by these enzymes, thereby alleviating the pathological conditions of OA and RA as well as many other auto-immune diseases.

There is also a need in the art for small molecule inhibitors of LpxC as potential antibacterial agents.

SUMMARY OF THE INVENTION

In its many embodiments, the present invention provides a novel class of compounds as inhibitors of LpxC, TACE, ADMP, aggrecanase, the production of TNF-α, MMPS, ADAMs or any combination thereof, methods of preparing such compounds, pharmaceutical compositions comprising one or more such compounds, methods of preparing pharmaceutical formulations comprising one or more such compounds, and methods of treatment, prevention, inhibition or amelioration of one or more diseases associated with LpxC, TACE, ADMP, aggrecanase, TNF-α, MMPs, ADAMs or any combination thereof using such compounds or pharmaceutical compositions.

In one embodiment, the present application discloses a compound, or pharmaceutically acceptable salts or solvates of said compound, said compound having the general structure shown in formula (I):

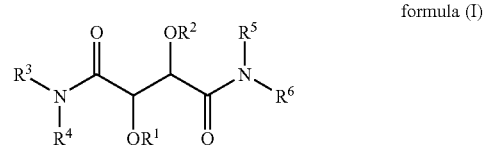

formula (I)

or a pharmaceutically acceptable salt, solvate or ester thereof, wherein:

(i) each of $R^1$ and $R^2$ independently is hydrogen or alkyl;

(ii) $R^3$ and $R^4$ taken together with the nitrogen to which they shown attached is heterocyclyl or heteroaryl, said heterocyclyl or heteroaryl having 1-3 heteroatoms including said nitrogen, said heterocyclyl or heteroaryl being optionally fused with aryl, heteroaryl, cycloalkyl, or heterocyclyl;

wherein said heterocyclyl or heteroaryl comprising $R^3$ and $R^4$ is substituted with one or two substituents, each substituent being independently selected from the group consisting of aryl and alkynyl;

wherein said aryl substituent is unsubstituted or is optionally substituted with one or two moieties selected independently from the group consisting of perhaloalkyl, halo, alkyl, alkoxy, cyano, perhaloalkoxy, and alkynyl moiety, wherein said alkynyl moiety is substituted with an aryl radical;

wherein said alkynyl subsituent is substituted with an aryl moiety, wherein said aryl moiety is unsubstituted or optionally substituted with one to three radicals selected from the group consisting of perhaloalkyl, halo, alkyl, alkoxy, cyano, and perhaloalkoxy; and (iii) each of $R^5$ and $R^6$ is alkyl, or alternatively $R^4$ and $R^5$ taken together with the nitrogen to which they shown attached is heterocyclyl having 1-3 heteroatoms including said nitrogen;

wherein said heterocyclyl comprising $R^5$ and $R^6$ is unsubstituted or optionally substituted with an aryl substitutent;

wherein said aryl substitutent is unsubstituted or optionally substituted with one to three moieties independently selected from the group consisting of perhaloalkyl, halo, alkyl, alkoxy, cyano, and perhaloalkoxy;

with the proviso that the aryl subsituent of said heterocyclyl or heteroaryl comprising $R^3$ and $R^4$ can be unsubstituted or optionally independently substituted with one to three moieties independently selected from the group consisting perhaloalkyl, halo, alkyl, alkoxy, cyano, and perhaloalkoxy only when $R^5$, $R^6$ taken together with the nitrogen to which $R^5$ and $R^6$ are shown attached is heterocyclyl.

In another embodiment, the present application discloses a compound, or pharmaceutically acceptable salts, solvates, or esters of said compound, said compound having the general structure shown in any one of those of formulae (II)-(IX):

formula (II)
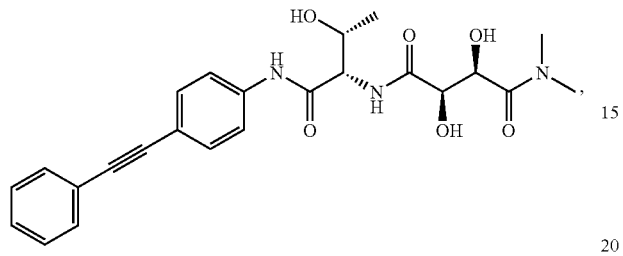

formula (III)
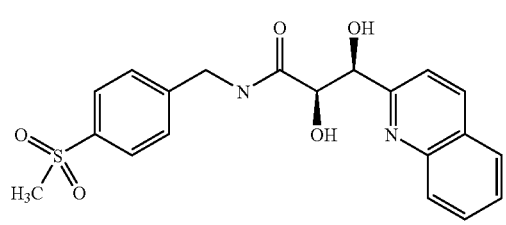

formula (IV)
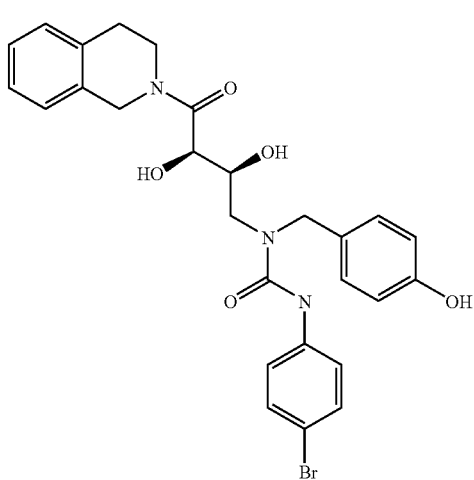

formula (V)
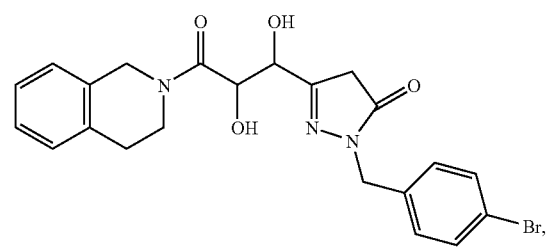

formula (VI)
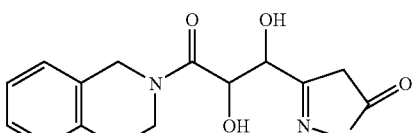

formula (VII)
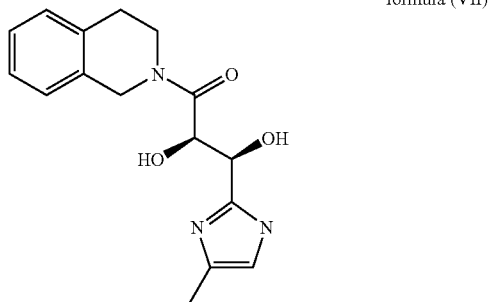

formula (VIII)
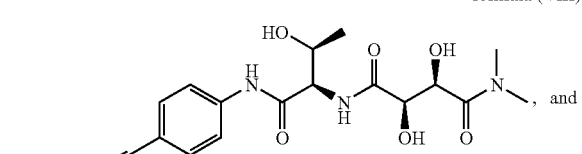

, and formula (IX)
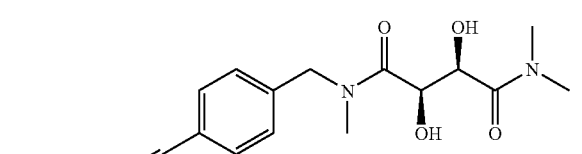

The compounds of Formulae (I) through (IX) can be useful as inhibitors and may be useful in the treatment and prevention of diseases associated with LpxC, TACE, aggrecanase, ADMP, TNF-α, MMPs, ADAMs or any combination thereof.

DETAILED DESCRIPTION OF THE INVENTION

In its several embodiments, the present invention provides a novel class of inhibitors of LpxC, TACE, aggrecanase, ADMP, the production of TNF-α, MMPs, ADAMs or any combination thereof, pharmaceutical compositions containing one or more of the compounds, methods of preparing pharmaceutical formulations comprising one or more such compounds, and methods of treatment, prevention or amelioration of one or more of the symptoms of inflammation.

In one embodiment, the present invention provides compounds which are represented by structural Formulae (I)-(IX) above or a pharmaceutically acceptable salt, solvate, ester or isomer thereof, wherein the various moieties are as described above.

In one embodiment of formula (I), $R^1$ and $R^2$ are both hydrogen.

In another embodiment of formula (I), the aryl substituent of the heterocyclyl or heteroaryl comprising $R^3$ and $R^4$ is substituted with an alkynyl moiety, wherein said alkynyl moiety is substituted with an aryl radical; and
the alkynyl substituent of the heterocyclyl or heteroaryl comprising $R^3$ and $R^4$ is substituted with an aryl moiety.

In another embodiment of formula (I), the heterocyclyl or heteroaryl comprising $R^3$ and $R^4$ is selected from the group consisting of pyrrolyl, benzopyrolyl, piperidinyl, benzopiperidinyl, pyrrolodinyl, and benzopyrrolodinyl.

In another embodiment of formula (I), the aryl substituent of the heterocyclyl or heteroaryl comprising the $R^3$ and $R^4$ is phenyl.

In another embodiment of formula (I), the aryl substituent of the heterocyclyl or heteroaryl comprising $R^3$ and $R^4$ is substituted with an alkynyl moiety, wherein said alkynyl moiety is substituted with an aryl radical, wherein said aryl radical is phenyl; and the alkynyl substituent of the heterocyclyl or heteroaryl comprising $R^3$ and $R^4$ is substituted with an aryl moiety.

In another embodiment of formula (I), $R^5$ and $R^6$ taken together with the nitrogen to which they shown attached is heterocyclyl.

In another embodiment of formula (I), $R^5$ and $R^6$ taken together with the nitrogen to which they shown attached is heterocyclyl, wherein said heterocyclyl comprising $R^5$ and $R^6$ is selected from the group consisting of pyrrolodinyl and piperizinyl.

In another embodiment of formula (I), the heterocyclyl comprising $R^5$ and $R^6$ is unsubstituted.

In another embodiment of formula (I), the heterocyclyl comprising $R^5$ and $R^6$ is substituted with an aryl substituent, wherein said aryl substituent is substituted with a halo moiety.

In another embodiment of formula (I), the heterocyclyl comprising $R^5$ and $R^6$ is substituted with an aryl substituent, wherein said aryl is phenyl, and wherein said phenyl is substituted with a halo moiety.

In another embodiment of formula (I), each of $R^5$ and $R^6$ is alkyl, which may be the same or different.

In another embodiment of formula (I), both $R^5$ and $R^6$ are methyl.

In another embodiment of formula (I): (i) $R^3$ and $R^4$ taken together with the nitrogen to which they shown attached is heterocyclyl or heteroaryl, said heterocyclyl or heteroaryl having 1-3 heteroatoms including said nitrogen, said heterocyclyl or heteroaryl being optionally fused with aryl, heteroaryl, cycloalkyl, or heterocyclyl;
wherein said heterocyclyl or heteroaryl comprising $R^3$ and $R^4$ is substituted with an aryl substituent;
wherein said aryl substituent is unsubstituted or is optionally substituted with one or two moieties selected independently from the group consisting of perhaloalkyl, halo, alkyl, alkoxy, cyano, perhaloalkoxy; and
(ii) $R^5$ and $R^6$ taken together with the nitrogen to which they are shown attached is heterocyclyl having 1-3 heteroatoms including said nitrogen;
wherein said heterocyclyl comprising $R^5$ and $R^6$ is unsubstituted or optionally substituted with an aryl substitutent;
wherein said aryl substitutent is unsubstituted or optionally substituted with one to three moieties independently selected from the group consisting of perhaloalkyl, halo, alkyl, alkoxy, cyano, and perhaloalkoxy.

In another embodiment of formula (I), the aryl substituent of the heterocyclyl or heteroaryl comprising $R^3$ and $R^4$ is unsubstituted or substituted with perhaloalkyl (e.g., $CF_3$).

In another embodiment of formula (I), the aryl substituent of the heterocyclyl or heteroaryl comprising $R^3$ and $R^4$ is is phenyl or benzyl.

In another embodiment of formula (I), the heterocyclyl comprising $R^5$ and $R^6$ is unsubstituted.

In another embodiment of formula (I), the heterocyclyl comprising $R^5$ and $R^6$ is unsubstituted, and is pyrrolodinyl.

In another embodiment, the compound of formula (I), is selected from the group consisting of:

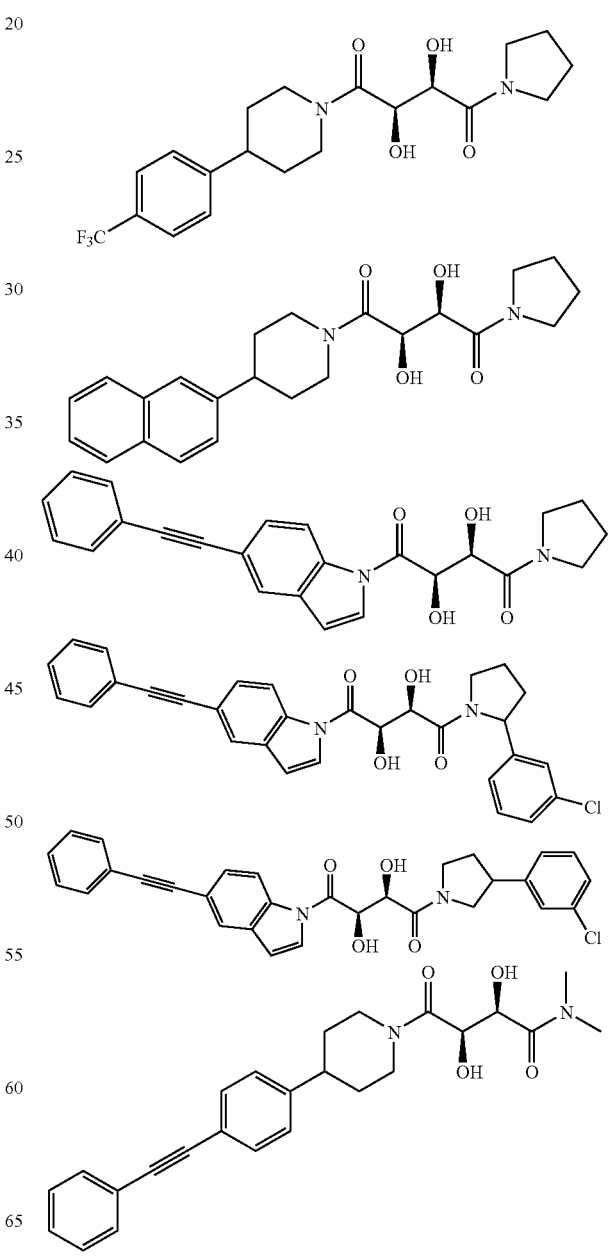

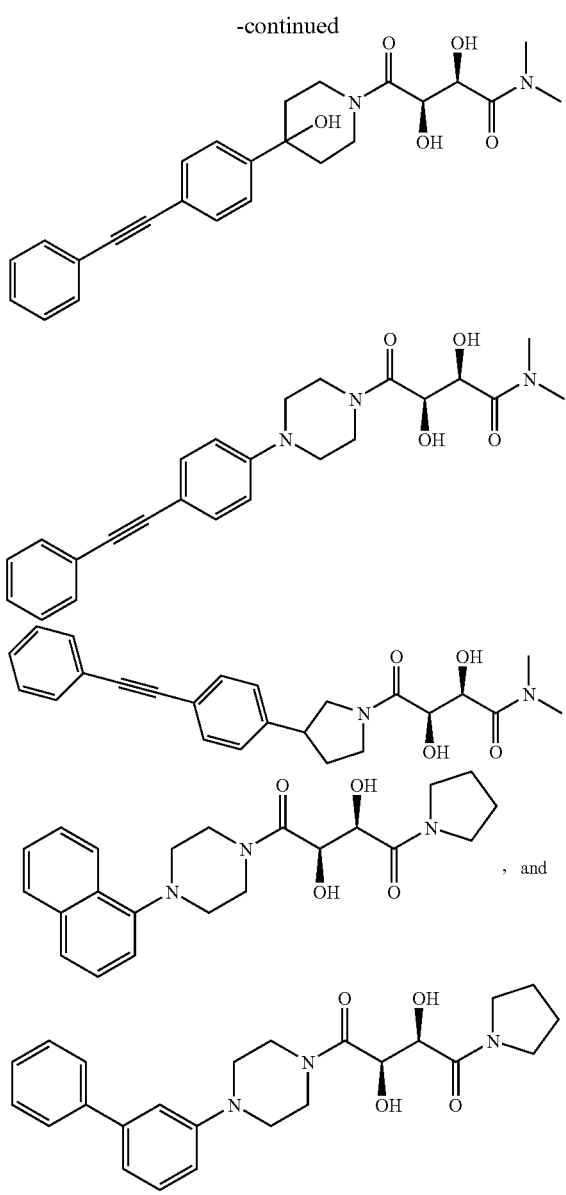

or a pharmaceutically acceptable salt, solvate or ester thereof.

As used above, and throughout this disclosure, the following terms, unless otherwise indicated, shall be understood to have the following meanings:

"Patient//subject" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. The term "substituted alkyl" means that the alkyl group may be substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, carboxy and —C(O)O-alkyl. Non-limiting examples of suitable alkyl groups include methyl, ethyl, n-propyl, isopropyl and t-butyl. The term "Fluoroalkyl" means an alkyl group in which alkyl is as previously described wherein one or more hydrogens are replaced with fluorine atoms.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. Non-limiting examples of suitable alkenyl groups include ethenyl, propenyl, n-butenyl, 3-methylbut-2-enyl, n-pentenyl, octenyl and decenyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. The term "substituted alkynyl" means that the alkynyl group may be substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl-group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like, as well as partially saturated species such as, for example, indanyl, tetrahydronaphthyl and the like.

"Halogen" means fluorine, chlorine, bromine, or iodine. Preferred are fluorine, chlorine and bromine.

The term "perhaloalkyl" means, unless otherwise stated, alkyl substituted with (2m'+1) halogen atoms, where m' is the total number of carbon atoms in the alkyl group. For example, the term "perhaloalkyl" includes trifluoromethyl, pentachloroethyl, 1,1,1-trifluoro-2-bromo-2-chloroethyl, and the like.

The term "perhaloalkoxy" means, unless otherwise stated, alkyloxy (i.e., alkoxy) substituted with (2m'+1) halogen atoms, where m' is the total number of carbon atoms in the alkoxy group. For example, the term "perhaloalkoxy" includes trifluoromethoxy, pentachloroethoxy, 1,1,1-trifluoro-2-bromo-2-chloroethoxy, and the like.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —C(=N—CN)—NH$_2$, —C(=NH)—NH$_2$, —C(=NH)—NH(alkyl), Y$_1$Y$_2$N—, Y$_1$Y$_2$N-alkyl-, Y$_1$Y$_2$NC(O)—, Y$_1$Y$_2$NSO$_2$— and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH$_3$)$_2$— and the like which form moieties such as, for example:

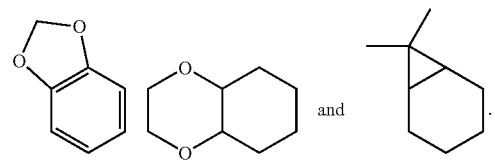

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

there is no —OH attached directly to carbons marked 2 and 5.

It should also be noted that tautomeric forms such as, for example, the moieties:

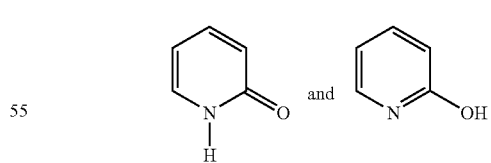

are considered equivalent in certain embodiments of this invention.

"Alkynylalkyl" means an alkynyl-alkyl- group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S(O$_2$)— group. Preferred groups are those in which the alkyl group is lower alkyl. The bond to the parent moiety is through the sulfonyl.

"Arylsulfonyl" means an aryl-S(O$_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "isolated" or "in isolated form" for a compound refers to the physical state of said compound after being isolated from a synthetic process or natural source or combination thereof. The term "purified" or "in purified form" for a compound refers to the physical state of said compound after being obtained from a purification process or processes described herein or well known to the skilled artisan, in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or in Formula (I)-(IX), its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of Formula I-IX or a salt and/or solvate thereof. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" is meant to describe an amount of compound or a composition of the present invention effective in inhibiting the CDK(s) and thus producing the desired therapeutic, ameliorative, inhibitory or preventative effect.

The compounds of Formula I-IX can form salts which are also within the scope of this invention. Reference to a compound of Formula I-IX herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I-IX contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I-IX may be formed, for example, by reacting a compound of Formula I-IX with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Compounds of Formula I-IX, and salts, solvates and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" "prodrug" and the like, is intended to equally apply to the salt, solvate and prodrug of enantiomers, stereoisomers, rotamers, tautomers, positional isomers, racemates or prodrugs of the inventive compounds.

Polymorphic forms of the compounds of Formula I-IX, and of the salts, solvates and prodrugs of the compounds of Formula I-IX, are intended to be included in the present invention.

The compounds according to the invention have pharmacological properties; in particular, the compounds of Formula I-IX can be inhibitors of LpxC, TACE, aggrecanase, ADMP, TNF-α, ADAM and/or MMP activity.

In one aspect, the invention provides a pharmaceutical composition comprising as an active ingredient at least one compound of formula (I)-(IX).

In another aspect, the invention provides a pharmaceutical composition of formula (I)-(IX) additionally comprising at least one pharmaceutically acceptable carrier.

In another aspect, the invention provides a method of treating disorders associated with LpxC, TACE, aggrecanase, ADMP, TNF-α, MMPs, ADAMs or any combination thereof or any combination thereof, said method comprising administering to a patient in need of such treatment a pharmaceutical composition which comprises therapeutically effective amounts of at least one compound of formula (I)-(IX).

In another aspect, the invention provides a use of a compound of formula (I)-(IX) for the manufacture of a medicament to treat disorders associated with LpxC, TACE, ADMP, aggrecanase, TNF-α, MMPs, ADAMs or any combination thereof.

The compounds of Formula I-IX can have anti-inflammatory activity and/or immunomodulatory activity and can be useful in the treatment of diseases including but not limited to septic shock, haemodynamic shock, sepsis syndrome, post ischaemic reperfusion injury, malaria, mycobacterial infection, meningitis, psoriasis, congestive heart failure, fibrotic diseases, cachexia, graft rejection, cancers such as cutaneous T-cell lymphoma, diseases involving angiogenesis, autoimmune diseases, skin inflammatory diseases, inflammatory bowel diseases such as Crohn's disease and colitis, OA and RA, ankylosing spondylitis, psoriatic arthritis, adult Still's disease, ureitis, Wegener's granulomatosis, Behcehe disease, Sjogren's syndrome, sarcoidosis, polymyositis, dermatomyositis, multiple sclerosis, sciatica, complex regional pain syndrome, radiation damage, hyperoxic alveolar injury, periodontal disease, HIV, non-insulin dependent diabetes mellitus, systemic lupus erythematosus, glaucoma, sarcoidosis, idiopathic pulmonary fibrosis, bronchopulmonary dysplasia, retinal disease, scleroderma, osteoporosis, renal ischemia, myocardial infarction, cerebral stroke, cerebral ischemia, nephritis, hepatitis, glomerulonephritis, cryptogenic fibrosing aveolitis, psoriasis, transplant rejection, atopic dermatitis, vasculitis, allergy, seasonal allergic rhinitis, reversible airway obstruction, adult respiratory distress syndrome, asthma, chronic obstructive pulmonary disease (COPD) and/or bronchitis. It is contemplated that a compound of this invention may be useful in treating one or more of the diseases listed.

The compounds of formula I-IX can also have antibacterial activity and can be useful in the treatment of a microbial infection, including gram negative and gram positive infections.

In another aspect, the invention provides a method of preparing a pharmaceutical composition for treating the disorders associated with LpxC, TACE, aggrecanase, ADMP, TNF-α, MMPs, ADAMs or any combination thereof, said method comprising bringing into intimate contact at least one compound of formula I-IX and at least one pharmaceutically acceptable carrier.

In another aspect, the invention provides a pharmaceutical composition for treating disorders associated with LpxC, TACE, aggrecanase, ADMP, TNF-α, MMP, ADAM or any combination thereof in a subject comprising, administering to the subject in need of such treatment a therapeutically effective amount of a compound of formula I-IX or a pharmaceutically acceptable salt, solvate, ester or isomer thereof.

In another aspect, the invention provides a compound of formula I-IX in purified form.

In another aspect, the invention provides a method of treating a condition or disease mediated by LpxC, TACE, aggrecanase, ADMP, MMPs, TNF-α, aggrecanase (such as aggrecanase 1, aggrecanase 2, aggrecanase 3, aggrecanase 4 or aggrecanase 5), or any combination thereof in a subject comprising: administering to the subject in need of such treatment a therapeutically effective amount of at least one compound of formula I-IX or a pharmaceutically acceptable salt, solvate or isomer thereof.

In another aspect, the invention provides a method of treating a condition or disease selected from the group consisting of rheumatoid arthritis, osteoarthritis, periodontitis, gingivitis, corneal ulceration, solid tumor growth and tumor invasion by secondary metastases, neovascular glaucoma, inflammatory bowel disease, multiple sclerosis and psoriasis in a subject, comprising: administering to the subject in need of such treatment a therapeutically effective amount of at least one compound of formula I-IX or a pharmaceutically acceptable salt, solvate or isomer thereof.

In another aspect, the invention provides a method of treating a condition or disease selected from the group consisting of fever, cardiovascular conditions, hemorrhage, coagulation, cachexia, anorexia, alcoholism, acute phase response, acute infection, shock, graft versus host reaction, autoimmune disease and HIV infection in a subject comprising administering to the subject in need of such treatment a therapeutically effective amount of at least one compound of formula I-IX or a pharmaceutically acceptable salt, solvate or isomer thereof.

In another aspect, the invention provides a method of treating a condition or disease selected from the group consisting of septic shock, haemodynamic shock, sepsis syndrome, post ischaemic reperfusion injury, malaria, mycobacterial infection, meningitis, psoriasis, congestive heart failure, fibrotic diseases, cachexia, graft rejection, cancers such as cutaneous T-cell lymphoma, diseases involving angiogenesis, autoimmune diseases, skin inflammatory diseases, inflammatory bowel diseases such as Crohn's disease and colitis, osteo and rheumatoid arthritis, ankylosing spondylitis, psoriatic arthritis, adult Still's disease, ureitis, Wegener's granulomatosis, Behcehe disease, Sjogren's syndrome, sarcoidosis, polymyositis, dermatomyositis, multiple sclerosis, sciatica, complex regional pain syndrome, radiation damage, hyperoxic alveolar injury, periodontal disease, HIV, non-insulin dependent diabetes mellitus, systemic lupus erythematosus, glaucoma, sarcoidosis, idiopathic pulmonary fibrosis, bronchopulmonary dysplasia, retinal disease, scleroderma, osteoporosis, renal ischemia, myocardial infarction, cerebral stroke, cerebral ischemia, nephritis, hepatitis, glomerulonephritis, cryptogenic fibrosing aveolitis, psoriasis, transplant rejection, atopic dermatitis, vasculitis, allergy, seasonal allergic rhinitis, reversible airway obstruction, adult respiratory distress syndrome, asthma, chronic obstructive pulmonary disease (COPD) and bronchitis in a subject comprising administering to the subject in need of such treatment a therapeutically effective amount of at least one compound of formula I-IX or a pharmaceutically acceptable salt, solvate or isomer thereof.

In another aspect, the invention provides a method of treating a condition or disease associated with COPD, comprising: administering to the subject in need of such treatment a therapeutically effective amount of at least one compound of formula I-IX or a pharmaceutically acceptable salt, solvate or isomer thereof.

In another aspect, the invention provides a method of treating a condition or disease associated with rheumatoid arthritis, comprising: administering to the subject in need of such treatment a therapeutically effective amount of at least one compound of formula I-IX or a pharmaceutically acceptable salt, solvate or isomer thereof.

In another aspect, the invention provides a method of treating a condition or disease associated with Crohn's disease, comprising: administering to the subject in need of such treatment a therapeutically effective amount of at least one compound of formula I-IX or a pharmaceutically acceptable salt, solvate or isomer thereof.

In another aspect, the invention provides a method of treating a condition or disease associated with psoriasis, comprising: administering to the subject in need of such treatment a therapeutically effective amount of at least one compound of formula I-IX or a pharmaceutically acceptable salt, solvate, ester or isomer thereof.

In another aspect, the invention provides a method of treating a condition or disease associated with ankylosing spondylitis, comprising: administering to the subject in need of such treatment a therapeutically effective amount of at least one compound of formula I-IX or a pharmaceutically acceptable salt, solvate or isomer thereof.

In another aspect, the invention provides a method of treating a condition or disease associated with sciatica, comprising: administering to the subject in need of such treatment a therapeutically effective amount of at least one compound of formula I-IX or a pharmaceutically acceptable salt, solvate or isomer thereof.

In another aspect, the invention provides a method of treating a condition or disease associated with complex regional pain syndrome, comprising: administering to the subject in need of such treatment a therapeutically effective amount of at least one compound of formula I-IX or a pharmaceutically acceptable salt, solvate or isomer thereof.

In another aspect, the invention provides a method of treating a condition or disease associated with psoriatic arthritis, comprising: administering to the subject in need of such treatment a therapeutically effective amount of at least one compound of formula I-IX or a pharmaceutically acceptable salt, solvate or isomer thereof.

In another aspect, the invention provides a method of treating a condition or disease associated with multiple sclerosis, comprising: administering to the subject in need of such treatment a therapeutically effective amount of at least one compound of formula I-IX or a pharmaceutically acceptable salt, solvate or isomer thereof, in combination with a compound selected from the group consisting of Avonex□, Betaseron, Copaxone or other compounds indicated for the treatment of multiple sclerosis.

Additionally, a compound of the present invention may be co-administered or used in combination with disease-modifying antirheumatic drugs (DMARDS) such as methotrexate, azathioprine, leflunomide, pencillinamine, gold salts, mycophenolate mofetil, cyclophosphamide and other similar drugs. They may also be co-administered with or used in combination with NSAIDS such as piroxicam, naproxen, indomethacin, ibuprofen and the like; COX-2 selective inhibitors such as Vioxx® and Celebrex®; immunosuppressives such as steroids, cyclosporin, Tacrolimus, rapamycin and the like; biological response modifiers (BRMs) such as Enbrel®, Remicade®, IL-1 antagonists, anti-CD40, anti-CD28, IL-10, anti-adhesion molecules and the like; and other anti-inflammatory agents such as p38 kinase inhibitors, PDE4 inhibitors, other chemically different TACE inhibitors, chemokine receptor antagonists, Thalidomide and other small molecule inhibitors of pro-inflammatory cytokine production.

Also, a compound of the present invention may be co-administered or used in combination with an H1 antagonist for the treatment of seasonal allergic rhinitis and/or asthma. Suitable H1 antagonists may be, for example, Claritin®, Clarinex®, Allegra®, or Zyrtec®.

In another aspect, the invention provides a method of treating a condition or disease mediated by TACE, aggrecanase, ADMP, MMPs, TNF-α, aggrecanase, or any combination thereof in a subject comprising: administering to the subject in need of such treatment a therapeutically effective amount of at least one compound of formula I-IX or a pharmaceutically acceptable salt, solvate or isomer thereof in combination with a therapeutically effective amount of at least one medicament selected from the group consisting of disease modifying anti-rheumatic drugs (DMARDS), NSAIDs, COX-2 inhibitors, COX-1 inhibitors, immunosuppressives, biological response modifiers (BRMs), anti-infammatory agents and H1 antagonists.

In another aspect, the invention provides a method of treating a condition or disease selected from the group consisting of rheumatoid arthritis, osteoarthritis, periodontitis, gingivitis, corneal ulceration, solid tumor growth and tumor invasion by secondary metastases, neovascular glaucoma, inflammatory bowel disease, multiple sclerosis and psoriasis in a subject, comprising: administering to the subject in need of such treatment a therapeutically effective amount of at least one compound of claim 1 or a pharmaceutically acceptable salt, solvate or isomer thereof in combination with a therapeutically effective amount of at least one medicament selected from the group consisting of DMARDS, NSAIDs, COX-2 inhibitors, COX-1 inhibitors, immunosuppressives, BRMs, anti-inflammatory agents and H1 antagonists.

In another aspect, the invention provides a method of treating a condition or disease selected from the group consisting of septic shock, haemodynamic shock, sepsis syndrome, post ischaemic reperfusion injury, malaria, mycobacterial infection, meningitis, psoriasis, congestive heart failure, fibrotic diseases, cachexia, graft rejection, cancers such as cutaneous T-cell lymphoma, diseases involving angiogenesis, autoimmune diseases, skin inflammatory diseases, inflammatory bowel diseases such as Crohn's disease and colitis, osteo and rheumatoid arthritis, ankylosing spondylitis, psoriatic arthritis, adult Still's disease, ureitis, Wegener's granulomatosis, Behcehe disease, Sjogren's syndrome, sarcoidosis, polymyositis, dermatomyositis, multiple sclerosis, sciatica, complex regional pain syndrome, radiation damage, hyperoxic alveolar injury, periodontal disease, HIV, non-insulin dependent diabetes mellitus, systemic lupus erythematosus, glaucoma, sarcoidosis, idiopathic pulmonary fibrosis, bronchopulmonary dysplasia, retinal disease, scleroderma, osteoporosis, renal ischemia, myocardial infarction, cerebral stroke, cerebral ischemia, nephritis, hepatitis, glomerulonephritis, cryptogenic fibrosing aveolitis, psoriasis, transplant rejection, atopic dermatitis, vasculitis, allergy, seasonal allergic rhinitis, reversible airway obstruction, adult respiratory distress syndrome, asthma, chronic obstructive pulmonary disease (COPD) and bronchitis in a subject comprising administering to the subject in need of such treatment a therapeutically effective amount of at least one compound of claim 1 or a pharmaceutically acceptable salt, solvate or isomer thereof in combination with a therapeutically effective amount of at least one medicament selected from the group consisting of DMARDS, NSAIDs, COX-2 inhibitors, COX-1 inhibitors, immunosuppressives, BRMs, anti-infammatory agents and H1 antagonists.

In another aspect, the invention provides a method for treating RA comprising administering a compound of the formula I-IX in combination with compound selected from the class consisting of a COX-2 inhibitor e.g. Celebrex® or Vioxx®; a COX-1 inhibitor e.g. Feldene®; an immunosuppressive e.g. methotrexate or cyclosporin; a steroid e.g. β-methasone; and anti-TNF-α compound, e.g. Enbrel® or Remicade®; a PDE IV inhibitor, or other classes of compounds indicated for the treatment of RA.

In another aspect, the invention provides a method for treating multiple sclerosis comprising administering a compound of the formula I-IX in combination with a compound selected from the group consisting of Avonex®, Betaseron, Copaxone or other compounds indicated for the treatment of multiple sclerosis.

In another aspect, the invention provides a method for the treatment of a microbial infection in a mammal, comprising administering to said mammal a therapeutically effective amount of a compound of formula I-IX or a pharmaceutically acceptable salt, solvate or ester thereof. In one embodiment, the microbe causing the infection is a bacteria, in another embodiment it is a fungus. In one embodiment, the microbial infection is a gram negative infection; in another embodiment, it is a gram negative infection.

In another aspect, the invention provides a method for the treatment of a microbial infection in a mammal, comprising administering to said mammal a therapeutically effective amount of a compound of formula I-IX in combination with one or more additional antibacterial or antifungal agent. In one embodiment, said additional antibacterial agent is active against gram negative bacteria. In onother embodiment, said additional antibacterial agent is active against gram positive bacteria.

In another embodiment, the bacterial infection is caused by at least one organism selected from the group consisting of *Acinetobacter baumannii, Acinetobacter calcoaceticus, Acinetobacter haemolyticus, Acinetobacter hydrophila, Actinobacillus actinomycetemcomitans, Aeromonas hydrophila, Alcaligenes xylosoxidans, Bacteroides distasonis, Bacteroides fragilis, Bacteroides melaninogenicus, Bacteroides ovatus, Bacteroides thetaiotaomicron, Bacteroides vulgatus, Bartonella henselae, Bordetella pertussis, Branhamella* catarrhalis, Brucella melitensis, Brucella abortus, Brucella canis, Burkholderia cepacia, Burkholderia mallei, Burkholderia pseudomallei, Campylobacter coli, Campylobacter fetus, Campylobacter jejuni, Citrobacter diversus, Citrobacter freundii, Citrobacter koseri, Coxiella burnetli, Edwarsiella tarda, Ehrlichia chafeenis, Eikenella corrondens, Enterobacter aerogenes, Enterobacter agglomerans, Enterobacter cloacae, Escherichia coli, Flavobacterium meningosepticum, Francisella tularensis, Fusobacterium spp., Haemophilus ducreyi, Haemophilus influenzae, Haemophilus parainfluenzae, Helicobacter pylori, Kingella kingae, Klebsiella oxytoca, Klebsiella ozaenae, Klebsiella pneumoniae, Klebsiella rhinoscleromatis, Legionella pneumophila, Moraxella catarrhalis, Morganella morganii, Neisseria gonorrhoeae, Neisseria meningitides, Pasteurella multocida, Plesiomonas shigelloides, Porphyromonas asaccharolytica, Porphyromonas gingivalis, Prevotella bivia, Prevotella buccae, Prevotella corporis, Prevotella endodontalis, Prevotella intermedia, Prevotella melaninogenica, Prevotella oralis, Proteus mirabilis, Proteus myxofaciens, Proteus penner, Proteus vulgaris, Providencia alcalifaciens, Providencia rettgeri, Providencia stuarfii, Pseudomonas aeruginosa, Pseudomonas fluorescens, Ricketsia prowozekii, Salmonella enterica, Serratia marcescens, Shigella boydii, Shigella dysenteriae, Shigella flexneri, Shigella sonnei, Stenotrophomonas maltophilia, Streptobacillus moniliformis, Vibrio alginolyticus, Vibrio cholerae, Vibrio parahaemolyticus, Vibrio vuluificus, Yersinia enterocolitica, Yersinia pestis, and Yersinia pseudotuberculosis.

In another embodiment, the bacterial infection is caused by at least one organism selected from the group consisting of Acinetobacter baumannii, Acinetobacter spp., Aeromonas hydrophila, Bacteroides fragilis, Bacteroides spp., Bordetella pertussis, Campylobacter jejuni, Campylobacter spp., Citrobacter freundii, Citrobacter spp., Enterobacter cloacae, Enterobacter spp., Escherichia coli, Fusobacterium spp., Haemophilus influenzae, Haemophilus parainfluenzae, Helicobacter pylori, Klebsiella pneumoniae, Klebsiella spp., Legionella pneumophila, Moraxella catarrhalis, Morganella morganii, Neisseria gonorrhoeae, Neisseria meningitides, Pasteurella multocida, Prevotella spp., Proteus mirabilis, Proteus spp., Providencia stuartii, Pseudomonas aeruginosa, Pseudomonas spp., Salmonella enterica, Salmonella typhi, Serratia marcescens, Shigella spp., Stenotrophomonas maltophilia, Vibrio cholerae, Vibrio spp., and Yersinia spp.

TACE activity is determined by a kinetic assay measuring the rate of increase in fluorescent intensity generated by TACE catalyzed cleavage of an internally quenched peptide substrate (SPDL-3). The purified catalytic domain of recombinant human TACE (rhTACEc, Residue 215 to 477 with two mutation (S266A and N452Q) and a 6xHis tail) is used in the assay. It is purified from the baculovirus/Hi5 cells expression system using affinity chromatography. The substrate SPDL-3 is an internally quenched peptide (MCA-Pro-Leu-Ala-Gln-Ala-Val-Arg-Ser-Ser-Ser-Dpa-Arg-NH2), with its sequence derived from the pro-TNF-α cleavage site. MCA is (7-Methoxycoumarin-4-yl)acetyl. Dpa is N-3-(2,4-Dinitrophenyl)-L-2,3-diaminopropionyl.

A 50 µl assay mixture contains 20 mM HEPES, pH 7.3, 5 mM $CaCl_2$, 100 µM $ZnCl_2$, 2% DMSO, 0.04% Methylcellulose, 30 µM SPDL-3, 70 pM rhTACEc and a test compound. RhTACEc is pre-incubated with the testing compound for 90 min. at 25° C. Reaction is started by addition of the substrate. The fluorescent intensity (excitation at 320 nm, emission at 405 nm) was measured every 45 seconds for 30 min. using a fluorospectrometer (GEMINI XS, Molecular Devices). Rate of enzymatic reaction is shown as Units per second. Effect of a test compound is shown as % of TACE activity in the absence of the compound.

The procedures of International Patent Publication WO00/05256 (published Feb. 3, 2000) were followed for detection of ADMP Activity and for measuring the $IC_{50}$ of the compounds of the present invention. This was indicative of activity against a desintgrin and metallopropeinase thrombo spondin 4 and 5 (ADAMTS-4-5).

The enzyme was purchased commercially from Calbiochem (Cat# PF113) and the peptide substrate described in the patent was custom-ordered from AnaSpec.

The standard LpxC assay consists of 0.2 nM LpxC enzyme, 1.0 µM UDP-3-O—(R-3-hydroxymyristoyl)-N-acetylglucosamine, and test compound, in assay buffer and 2% DMSO. Assay buffer is comprised of 25 mM HEPES, pH 7.3, 150 mM NaCl, 2.0 mM DTT, and 0.01% BSA. The enzyme reaction is carried out in a 96-well assay plate, in a final volume of 102 µL. Solutions of test compounds are prepared in 100% DMSO. Reaction additions, in order, are (1) 2.0 µL compound solution, (2) 80 µL of assay buffer, (3) 10 µL of 10 µM UDP-3-O—(R-3-hydroxymyristoyl)-N-acetylglucosamine (in assay buffer) and, (4) 10 µL of LpxC enzyme (20 nM in assay buffer) to initiate the reaction. In positive control reactions, addition (1) has 2.0 µL of 100% DMSO (without compound); these reactions are used as the total signal (TSB) value. Reactions are incubated at room temperature for 60 minutes when 10 µL of 1 N HCl is added to stop the reaction. The plate is shaken by hand for 10 seconds to ensure complete quenching. Assay plates are sealed with foil tape, and stored at −80° C. for 24-48 hr prior to analysis.

The concentrations of substrate and product in the reaction mixtures are determined with BioTrove's proprietary RapidFire™ high-throughput mass spectrometry (HTMS). Assay mixtures are partially purified with reverse phase chromatography, where they are washed with water containing 5 mM ammonium formate and eluted onto the mass spectrometer in 80% acetonitrile, 20% water, and 5 mM ammonium formate. The mass spectrometry peak areas of the substrate and product are measured to determine the concentration of these analytes. The assay signal is the percentage of substrate that is converted to product. Percent inhibition, % I, in test samples is determined from the following equation:

$$\% I = 100 * \frac{(TSB - SampleSignal)}{(TSB)}.$$

Inhibitory activities of representative compounds of the present invention are set forth in the table below. In this table below, greater than 30% inhibition is assigned a rating of "A", 10-30% inhibition is assigned a rating of "B", and less than 10% inhibition is assigned a rating of "C".

| S. No. | Structure | LpxC enzyme assay rating (% inhibition at indicated concentrations) ||||||||||
|---|---|---|---|---|---|---|---|---|---|---|---|
| | | 50 | 25 | 12.50 | 6.25 | 3.13 | 1.56 | 0.78 | 0.39 | 0.20 | 0.10 |
| 25 | 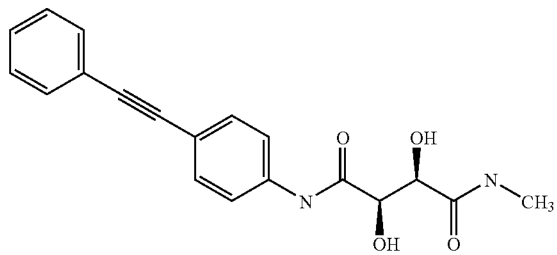 | C | C | B | C | C | C | C | C | C | C |
| 26 | 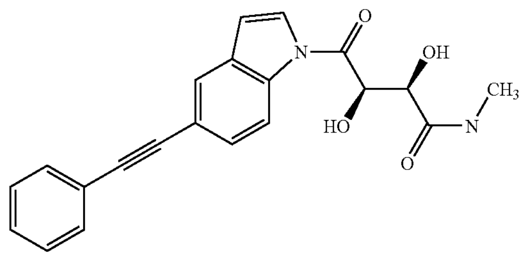 | B | C | B | C | C | C | C | C | C | C |
| 27 | 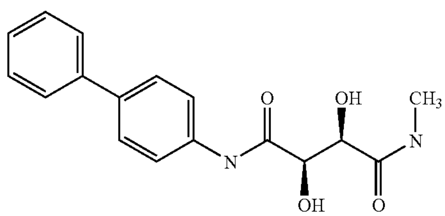 | B | B | B | B | B | C | C | C | C | C |
| 28 | 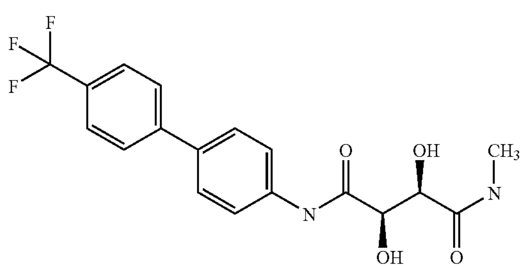 | C | C | B | C | C | C | C | C | C | C |
| 29 | 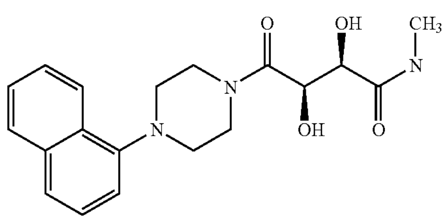 | B | B | B | B | B | B | C | C | C | C |
| 30 | 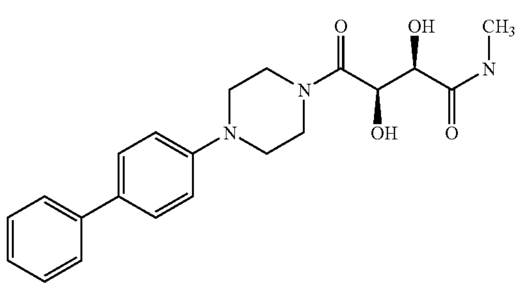 | A | B | B | B | B | C | C | B | B | C |

-continued

| S. No. | Structure | LpxC enzyme assay rating (% inhibition at indicated concentrations) | | | | | | | | | |
|---|---|---|---|---|---|---|---|---|---|---|---|
| | | 50 | 25 | 12.50 | 6.25 | 3.13 | 1.56 | 0.78 | 0.39 | 0.20 | 0.10 |
| 31 | 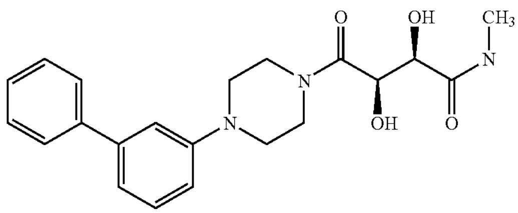 | B | B | B | C | B | B | B | C | B | C |
| 32 | 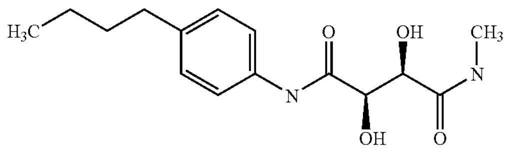 | B | B | B | C | B | C | B | B | B | B |
| 33 | 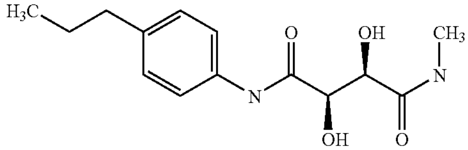 | C | C | C | B | B | B | C | C | C | C |
| 34 | 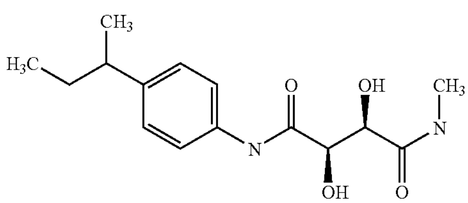 | B | B | C | B | C | B | B | C | B | C |
| 35 | 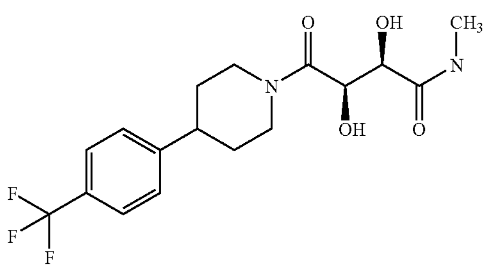 | B | C | C | C | C | B | C | C | C | C |
| 36 | 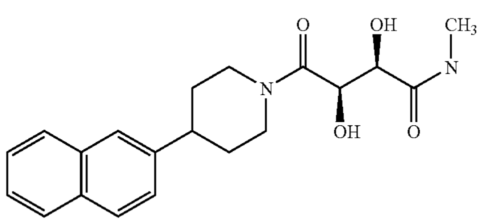 | C | C | C | C | C | C | C | C | C | C |
| 37 | 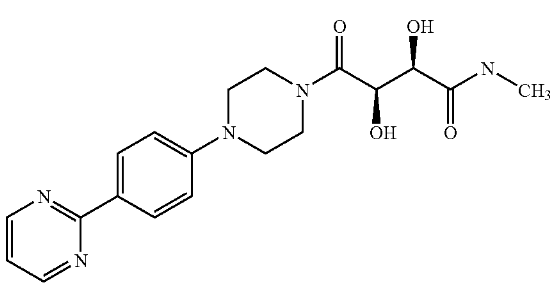 | C | B | C | B | C | C | C | C | C | C |

-continued

| S. No. | Structure | LpxC enzyme assay rating (% inhibition at indicated concentrations) | | | | | | | | | |
|---|---|---|---|---|---|---|---|---|---|---|---|
| | | 50 | 25 | 12.50 | 6.25 | 3.13 | 1.56 | 0.78 | 0.39 | 0.20 | 0.10 |
| 38 | (structure) | B | C | C | C | C | C | C | C | C | C |
| 39 | (structure) | B | C | C | B | B | C | B | C | C | C |
| 40 | (structure) | C | B | B | C | C | C | B | C | C | C |
| 41 | (structure) | B | B | C | B | B | B | C | C | C | C |
| 42 | (structure) | C | B | B | B | C | B | B | B | C | C |
| 43 | (structure) | A | A | A | B | B | B | C | C | B | C |

-continued

| S. No. | Structure | LpxC enzyme assay rating (% inhibition at indicated concentrations) | | | | | | | | | |
|---|---|---|---|---|---|---|---|---|---|---|---|
| | | 50 | 25 | 12.50 | 6.25 | 3.13 | 1.56 | 0.78 | 0.39 | 0.20 | 0.10 |
| 44 | 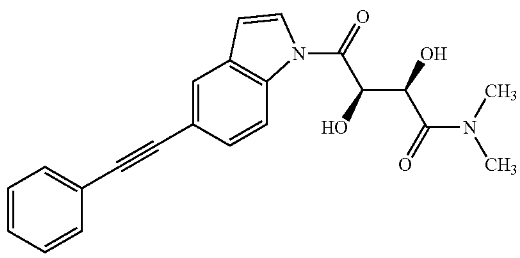 | A | A | A | B | B | C | C | C | B | C |
| 45 | 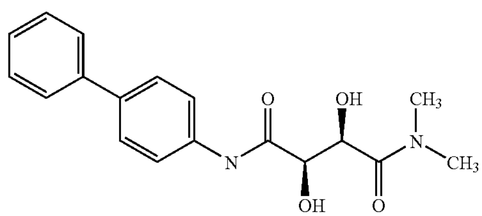 | C | C | C | C | C | C | C | C | C | C |
| 46 | 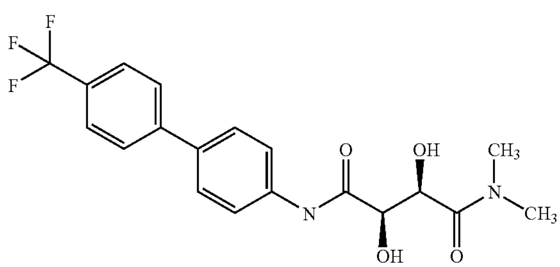 | A | B | B | C | C | C | C | C | C | C |
| 47 | 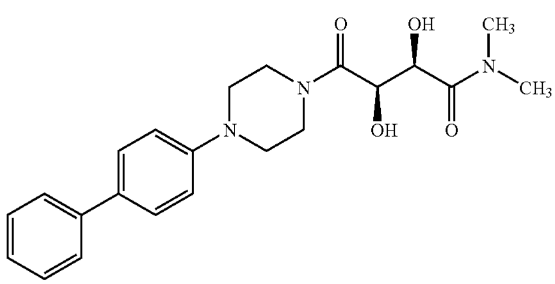 | B | C | B | B | B | C | B | C | B | B |
| 48 | 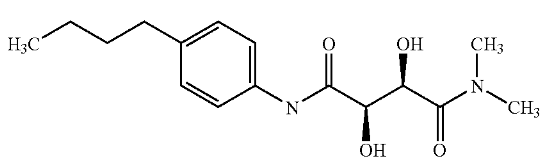 | B | C | B | C | B | C | C | C | C | B |
| 49 | 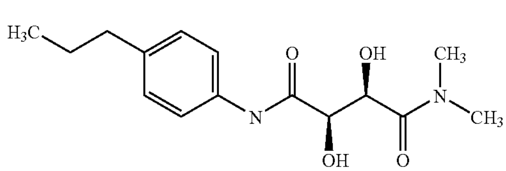 | C | B | C | C | C | C | C | B | C | C |

-continued
| S. No. | Structure | LpxC enzyme assay rating (% inhibition at indicated concentrations) | | | | | | | | | |
|---|---|---|---|---|---|---|---|---|---|---|---|
| | | 50 | 25 | 12.50 | 6.25 | 3.13 | 1.56 | 0.78 | 0.39 | 0.20 | 0.10 |
| 50 | 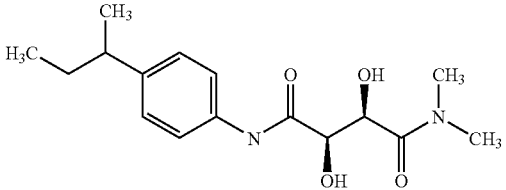 | B | C | B | B | C | C | B | C | C | C |
| 51 | 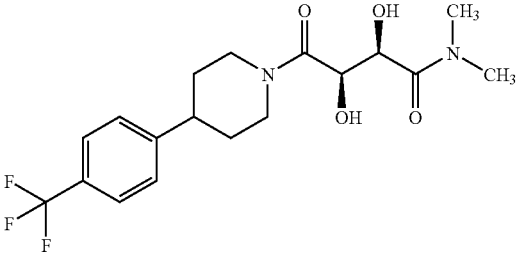 | B | B | C | C | C | B | C | C | C | B |
| 52 | 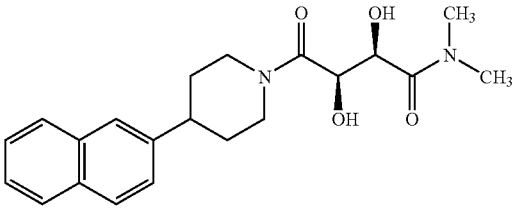 | A | B | B | B | C | C | C | C | C | C |
| 53 | 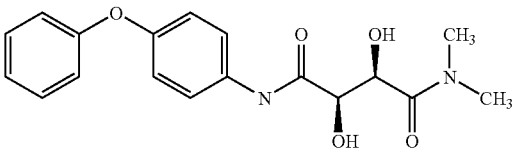 | C | C | C | C | C | C | B | C | C | C |
| 54 | 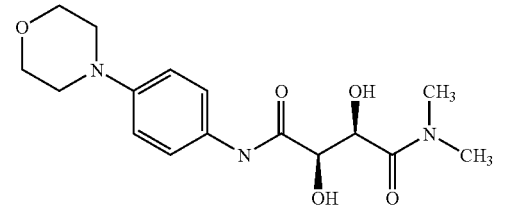 | C | C | C | C | B | C | C | C | C | C |
| 55 | 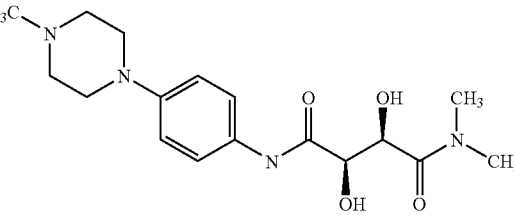 | B | B | C | C | B | B | B | C | B | C |
| 56 | 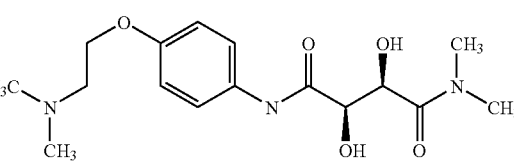 | C | C | C | B | C | C | C | C | B | C |

-continued

| S. No. | Structure | LpxC enzyme assay rating (% inhibition at indicated concentrations) | | | | | | | | | |
|---|---|---|---|---|---|---|---|---|---|---|---|
| | | 50 | 25 | 12.50 | 6.25 | 3.13 | 1.56 | 0.78 | 0.39 | 0.20 | 0.10 |
| 57 | 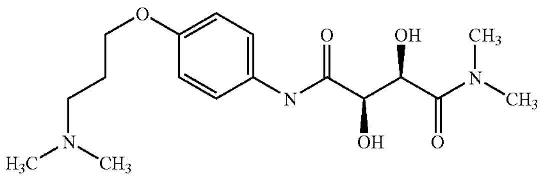 | C | B | C | C | C | C | C | B | C | B |
| 58 | 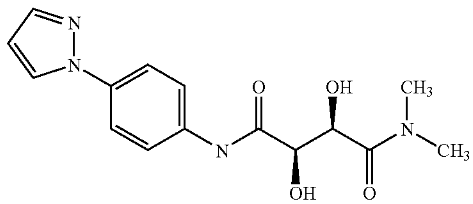 | B | C | B | B | B | C | B | C | B | C |
| 59 | 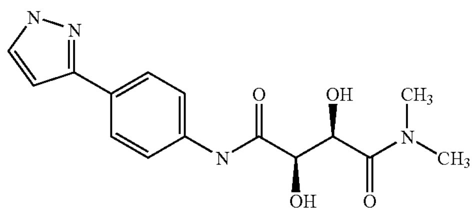 | C | B | C | C | C | C | C | B | C | B |
| 60 | 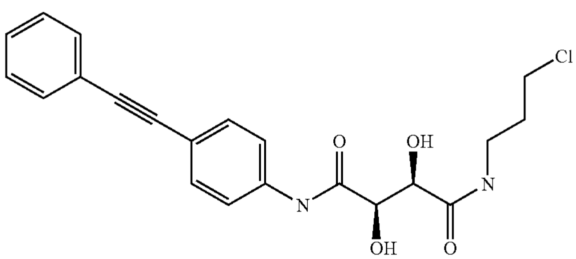 | C | C | B | B | B | C | B | B | C | C |
| 61 | 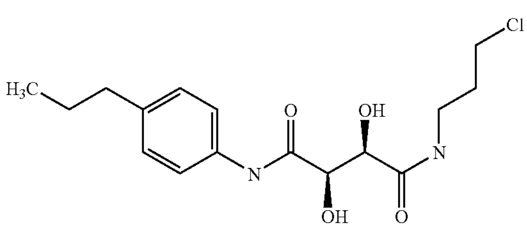 | B | B | C | C | C | C | C | C | C | C |
| 62 | 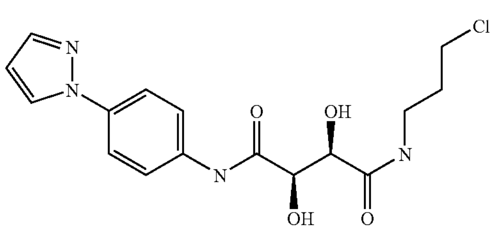 | C | B | B | B | C | B | C | C | C | C |

-continued

| S. No. | Structure | LpxC enzyme assay rating (% inhibition at indicated concentrations) | | | | | | | | | |
|---|---|---|---|---|---|---|---|---|---|---|---|
| | | 50 | 25 | 12.50 | 6.25 | 3.13 | 1.56 | 0.78 | 0.39 | 0.20 | 0.10 |
| 63 | (phenylethynyl-phenyl-NH-CO-CH(OH)-CH(OH)-CO-pyrrolidine) | A | A | A | B | B | B | C | B | B | B |
| 64 | (biphenyl-NH-CO-CH(OH)-CH(OH)-CO-pyrrolidine) | B | B | B | B | B | C | B | C | B | B |
| 65 | (4'-CF₃-biphenyl-NH-CO-CH(OH)-CH(OH)-CO-pyrrolidine) | B | B | B | B | B | B | C | B | B | B |
| 66 | (4-butyl-phenyl-NH-CO-CH(OH)-CH(OH)-CO-pyrrolidine) | B | A | B | B | B | B | C | B | C | C |
| 67 | (4-propyl-phenyl-NH-CO-CH(OH)-CH(OH)-CO-pyrrolidine) | B | B | C | B | C | C | C | B | B | B |
| 68 | (4-sec-butyl-phenyl-NH-CO-CH(OH)-CH(OH)-CO-pyrrolidine) | B | B | C | B | B | C | C | C | C | C |

| S. No. | Structure | LpxC enzyme assay rating (% inhibition at indicated concentrations) | | | | | | | | | |
|---|---|---|---|---|---|---|---|---|---|---|---|
| | | 50 | 25 | 12.50 | 6.25 | 3.13 | 1.56 | 0.78 | 0.39 | 0.20 | 0.10 |
| 69 | 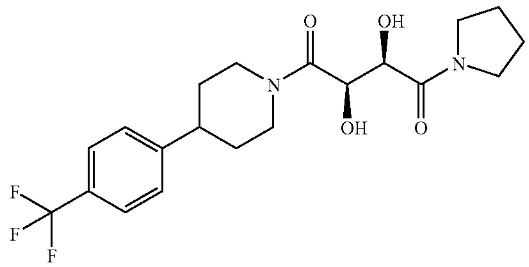 | C | C | C | C | C | C | C | C | C | C |
| 70 | 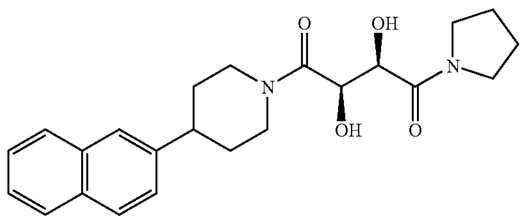 | C | B | C | C | C | C | B | C | C | C |
| 71 | 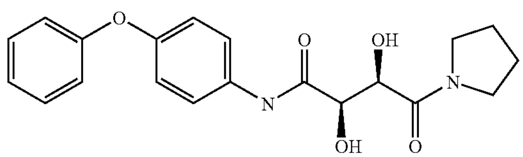 | C | C | C | C | B | B | B | B | C | B |
| 72 | 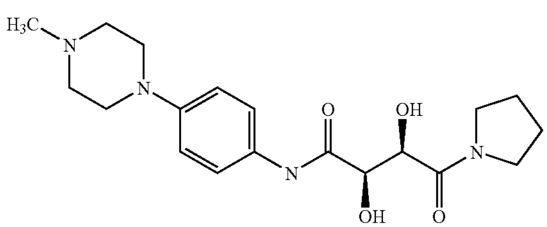 | B | C | C | C | C | C | C | C | C | B |
| 73 | 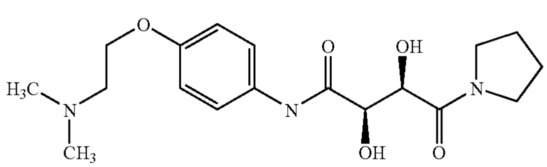 | C | C | C | C | C | C | B | C | B | C |
| 74 | 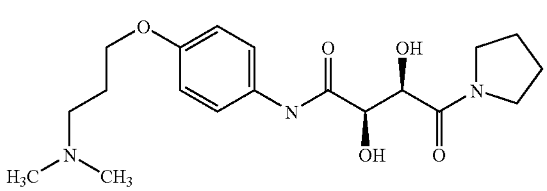 | C | C | C | C | B | B | C | C | C | B |
| 75 | 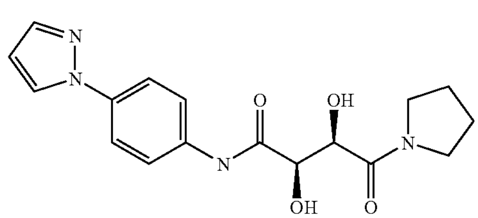 | B | C | C | B | B | C | B | C | C | C |

-continued

| S. No. | Structure | LpxC enzyme assay rating (% inhibition at indicated concentrations) | | | | | | | | | |
|---|---|---|---|---|---|---|---|---|---|---|---|
| | | 50 | 25 | 12.50 | 6.25 | 3.13 | 1.56 | 0.78 | 0.39 | 0.20 | 0.10 |
| 76 | 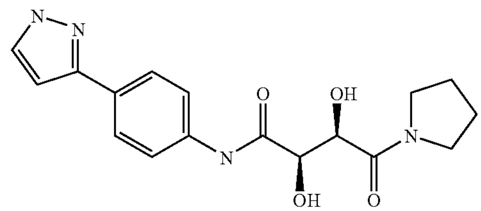 | C | C | C | B | C | B | C | C | C | C |
| 77 | 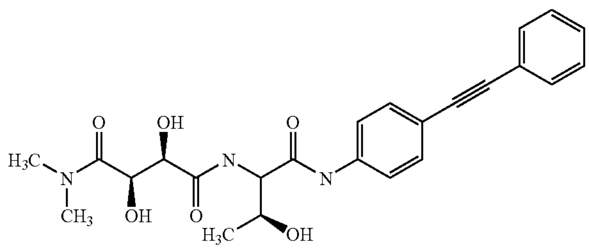 | A | B | C | C | C | C | C | C | C | |
| 78 | 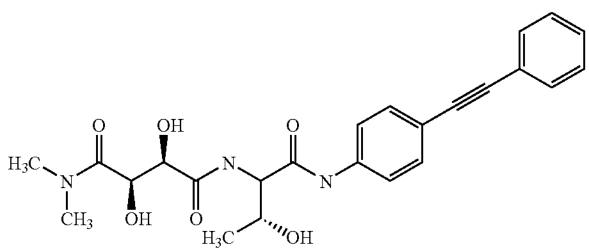 | A | B | B | B | C | C | B | C | C | |
| 79 | 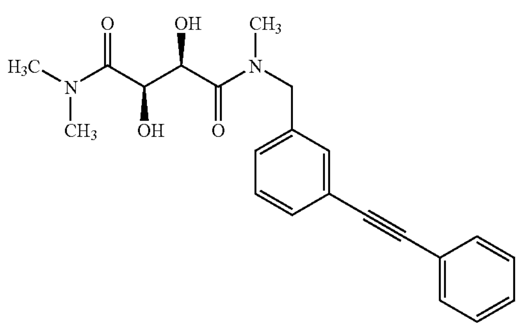 | A | B | B | C | C | C | C | C | C | |
| 103 | 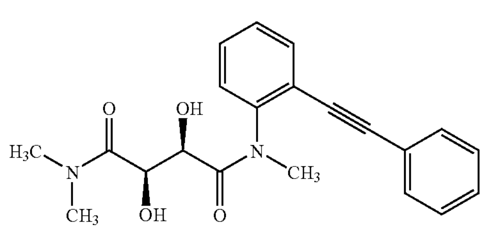 | C | B | C | B | B | B | B | C | C | |

-continued

| S. No. | Structure | LpxC enzyme assay rating (% inhibition at indicated concentrations) | | | | | | | | | |
|---|---|---|---|---|---|---|---|---|---|---|---|
| | | 50 | 25 | 12.50 | 6.25 | 3.13 | 1.56 | 0.78 | 0.39 | 0.20 | 0.10 |
| 80 | 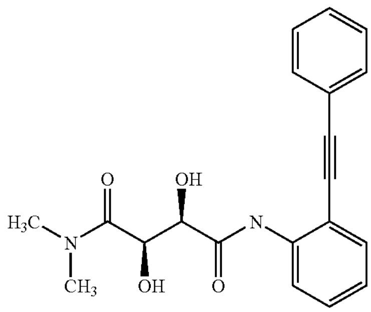 | C | B | C | C | C | C | C | C | C | |
| 81 | 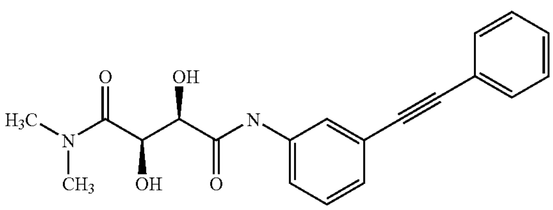 | C | C | C | C | C | C | C | C | C | |
| 104 | 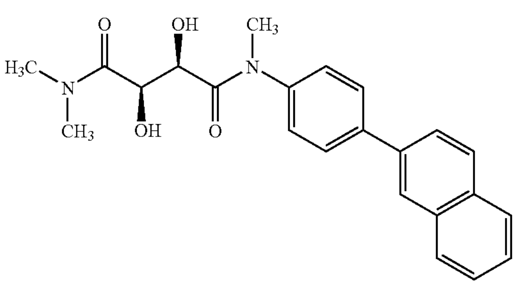 | B | C | C | C | C | C | C | C | C | |
| 82 | 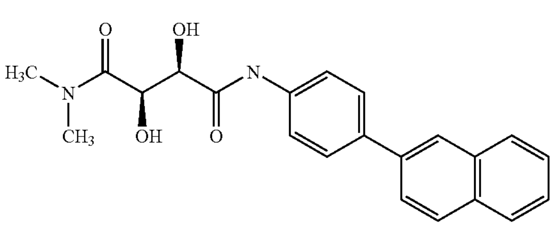 | A | A | B | B | C | C | C | B | C | |

ADMP inhibitory activities for representative compounds are shown in the table below. Compounds possessing $IC_{50}$ values greater than 5 µM (>5 µM) are designated as "D" class. Compounds possessing $IC_{50}$ values greater than 1 µM but up to 5 µM (>0.1 µM-5 µM) are designated as "C" class. $IC_{50}$ values between 0.25 µM to 1.0 µM (0.25 µM-1 µM) are designated as "B" class. $IC_{50}$ values less than 0.25 µM (<0.25 µM) are designated as "A" class.

| S. No. | Structure | $IC_{50}$ rating |
|---|---|---|
| 108 | 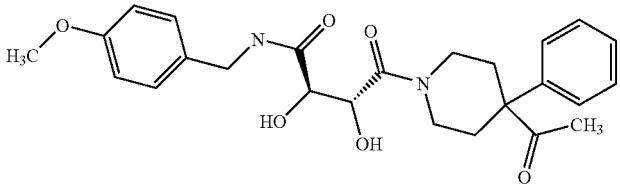 | B |
| 110 | 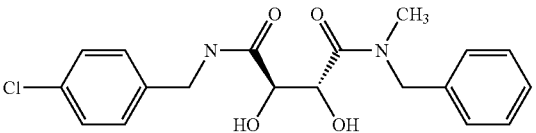 | B |
| 111 | 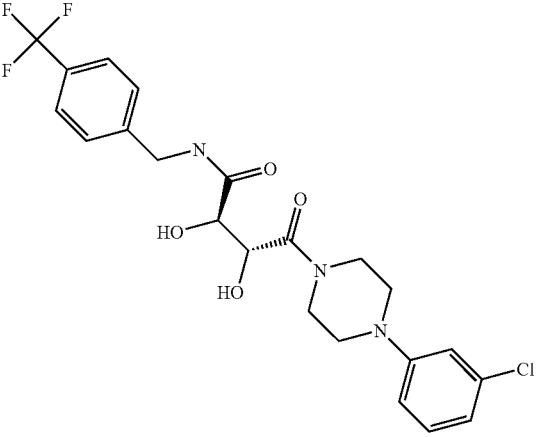 | B |
| 113 | 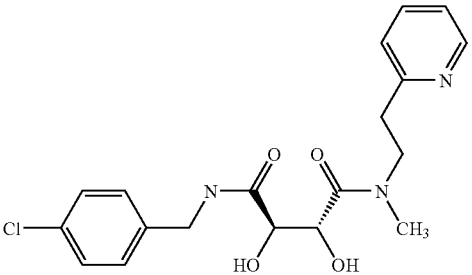 | B |
| 114 | 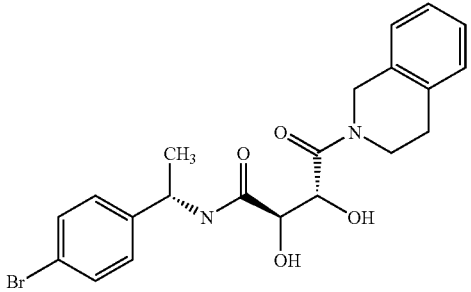 | A |

-continued

| S. No. | Structure | IC$_{50}$ rating |
|---|---|---|
| 118 | 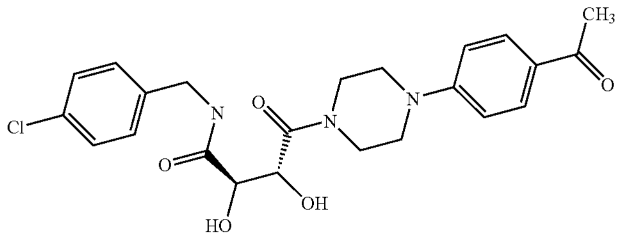 | D |
| 121 | 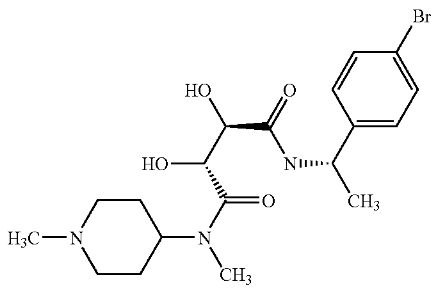 | C |
| 122 | 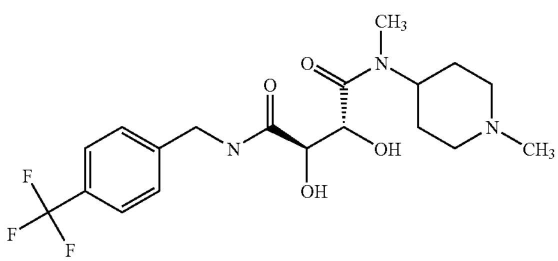 | B |
| 123 | 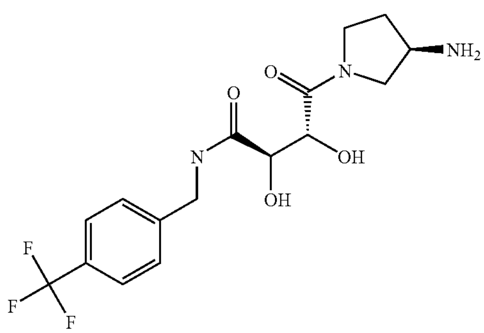 | C |
| 125 | 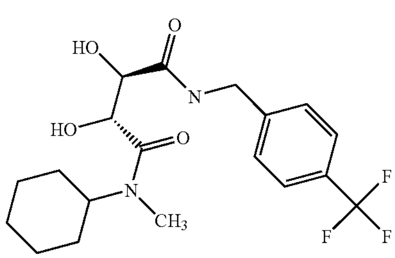 | B |

-continued

| S. No. | Structure | IC$_{50}$ rating |
|---|---|---|
| 126 | 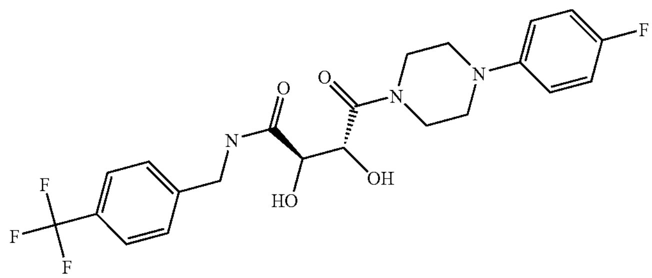 | B |
| 127 | 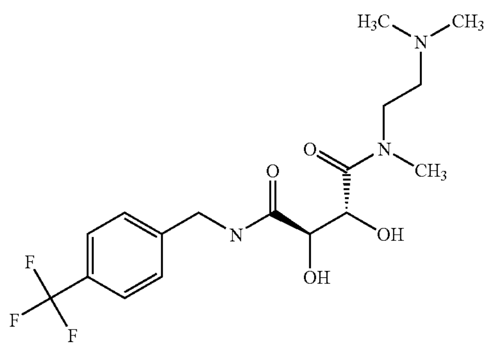 | D |
| 130 | 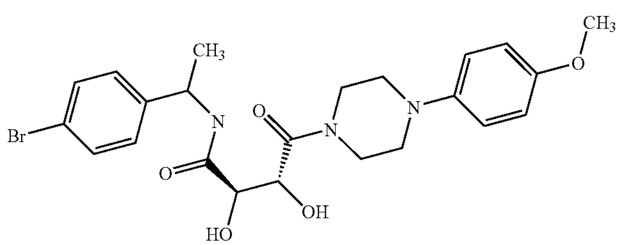 | A |
| 131 | 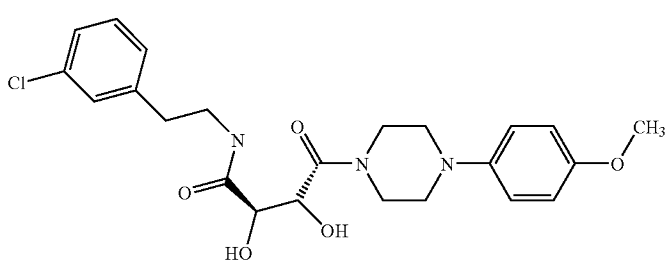 | B |

-continued
| S. No. | Structure | IC₅₀ rating |
|---|---|---|
| 132 | 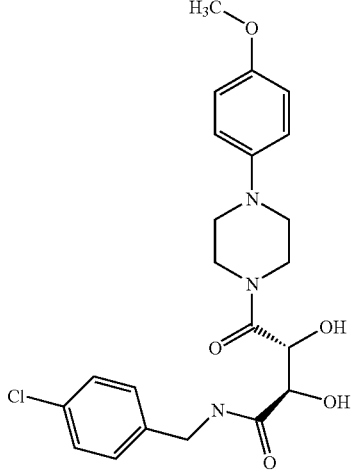 | B |
| 133 | 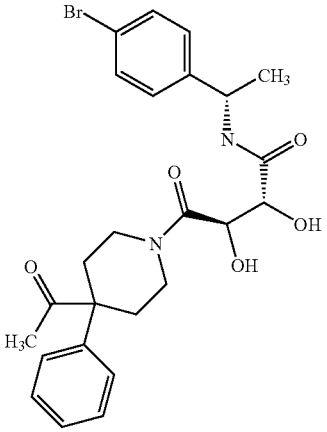 | A |
| 134 | 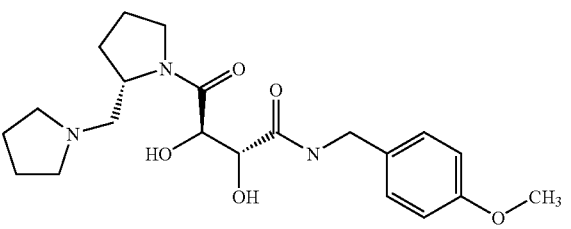 | B |
| 138 | 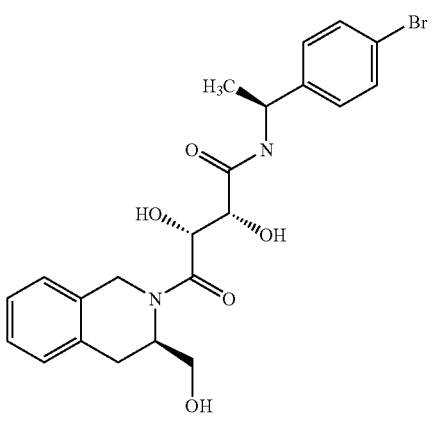 | A |

-continued
| S. No. | Structure | IC$_{50}$ rating |
|---|---|---|
| 139 | 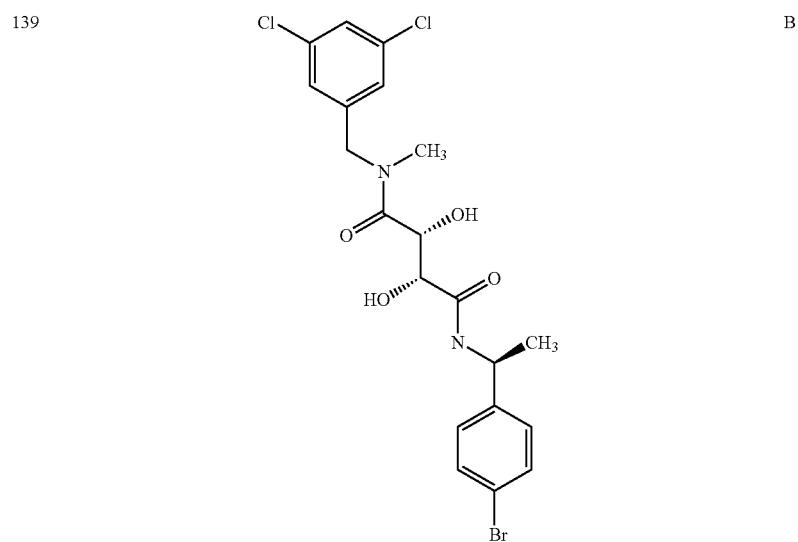 | B |
| 142 | 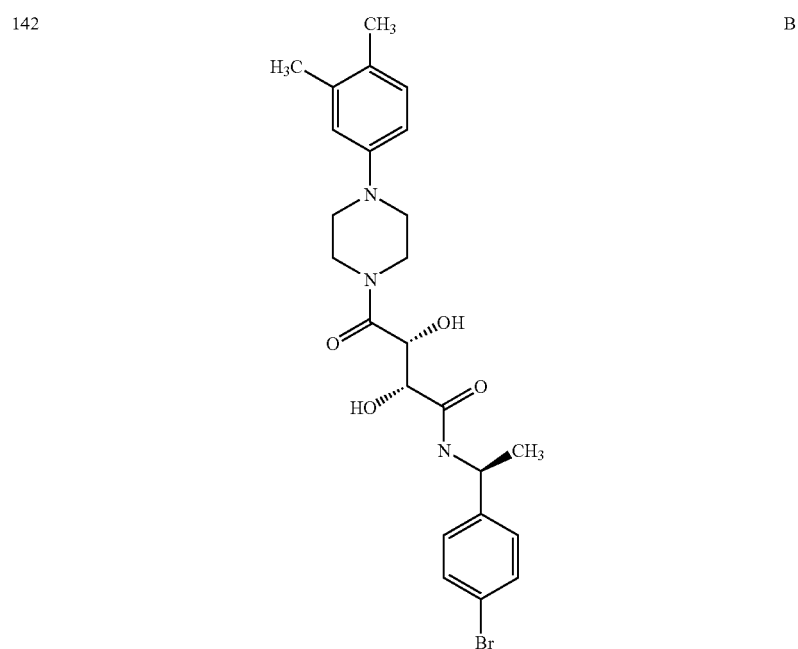 | B |

-continued
| S. No. | Structure | IC$_{50}$ rating |
|---|---|---|
| 143 | 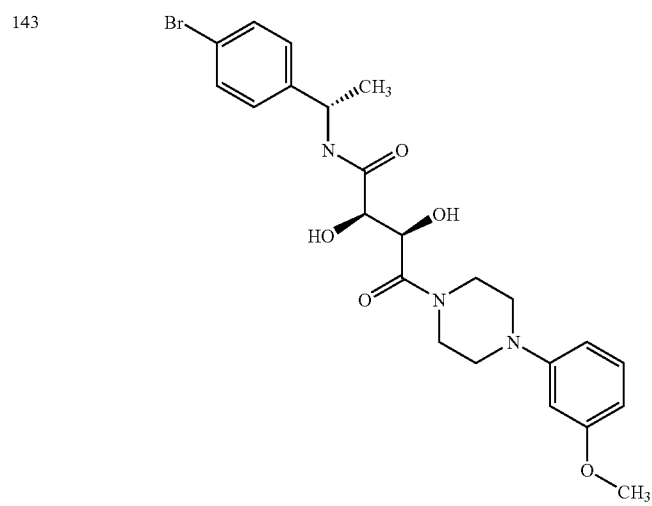 | A |
| 144 | 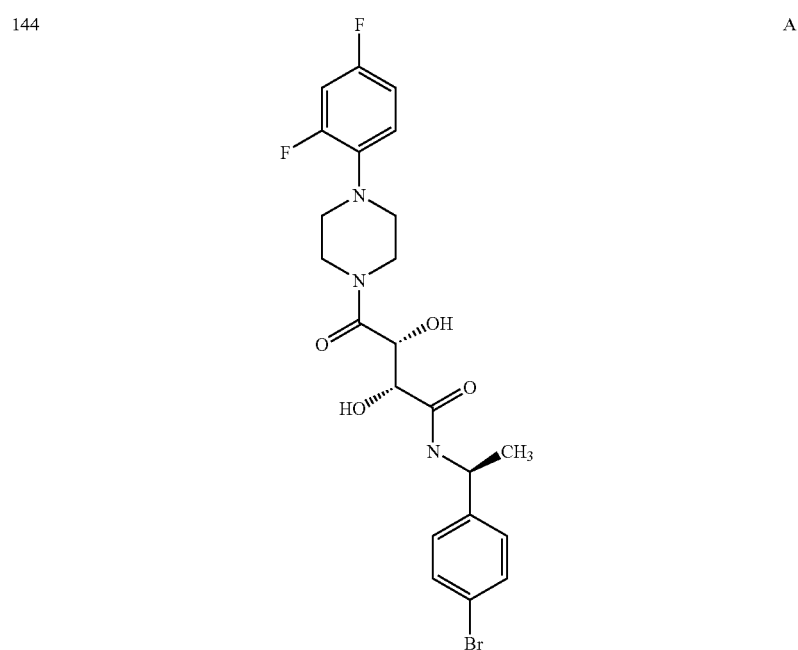 | A |

| S. No. | Structure | IC$_{50}$ rating |
|---|---|---|
| 148 | 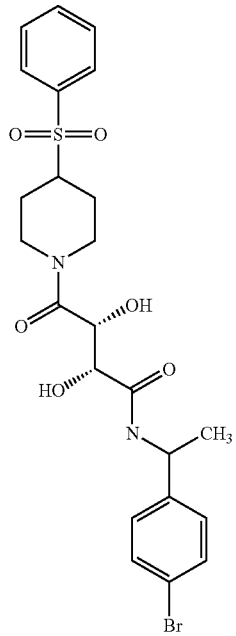 | A |
| 149 | 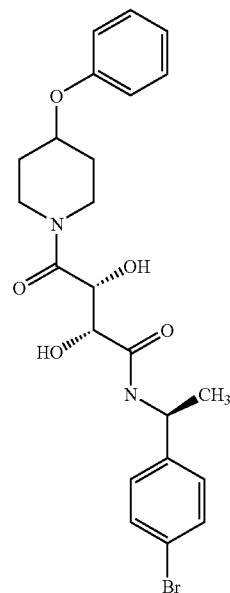 | A |

-continued
| S. No. | Structure | IC$_{50}$ rating |
|---|---|---|
| 150 | 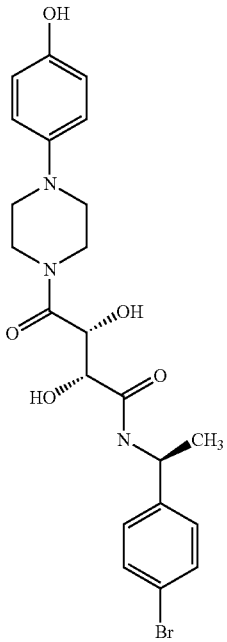 | C |
| 151 | 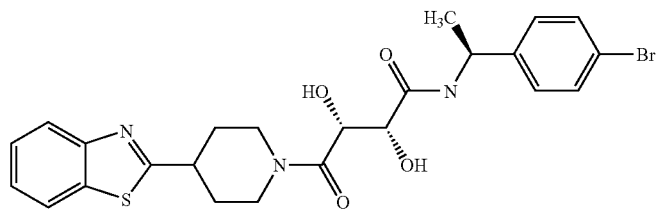 | A |
| 152 | 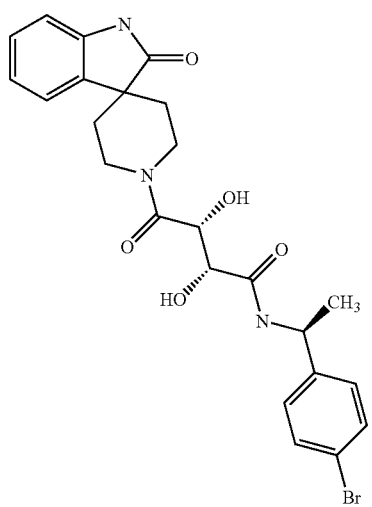 | C |

-continued

| S. No. | Structure | IC$_{50}$ rating |
|---|---|---|
| 158 | 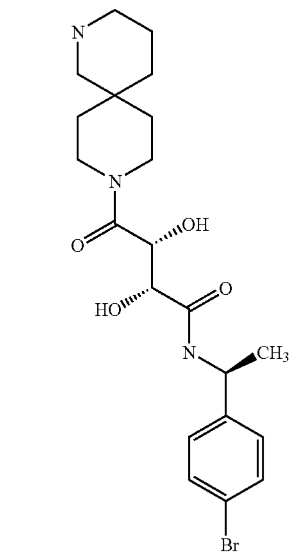 | D |
| 160 | 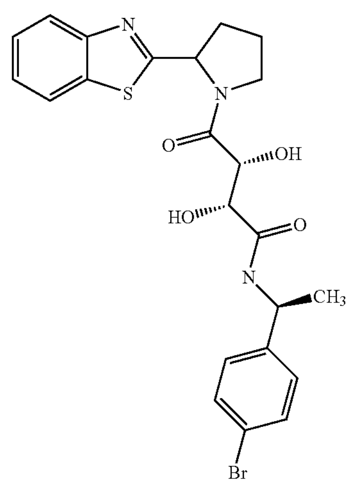 | A |
| 164 | 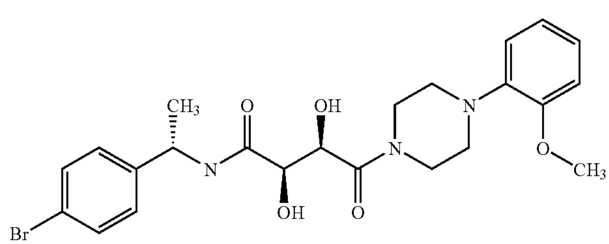 | B |

| S. No. | Structure | IC$_{50}$ rating |
|---|---|---|
| 165 | 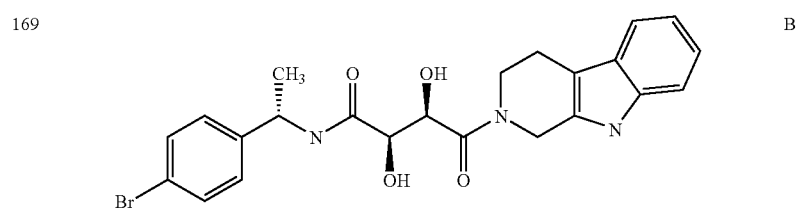 | C |
| 169 | 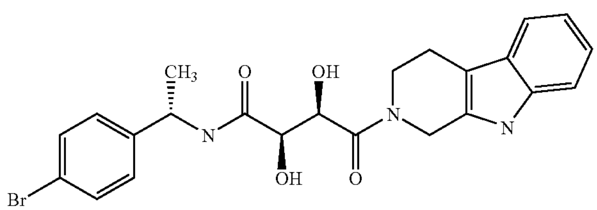 | B |
| 172 | 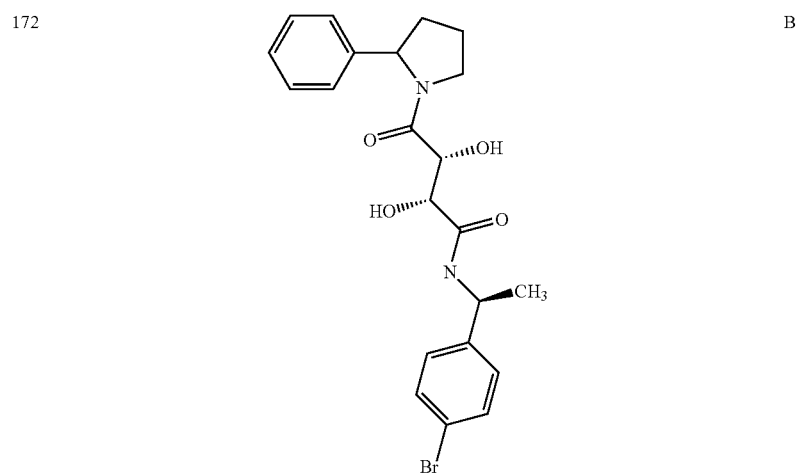 | B |

| S. No. | Structure | IC50 rating |
|---|---|---|
| 173 | 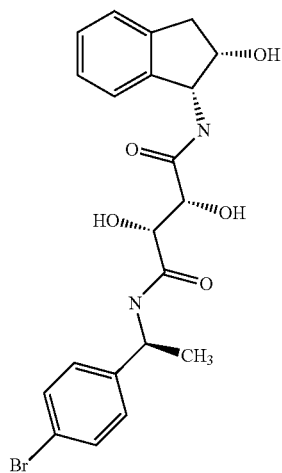 | D |
| 174 | 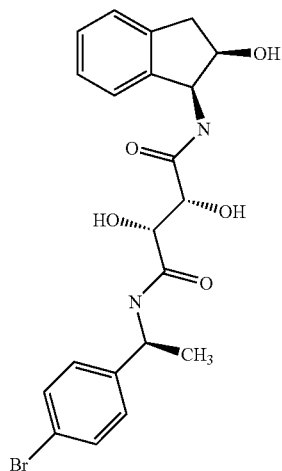 | D |
| 175 | 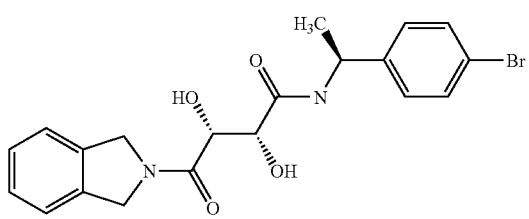 | B |

-continued
| S. No. | Structure | IC$_{50}$ rating |
|---|---|---|
| 176 | 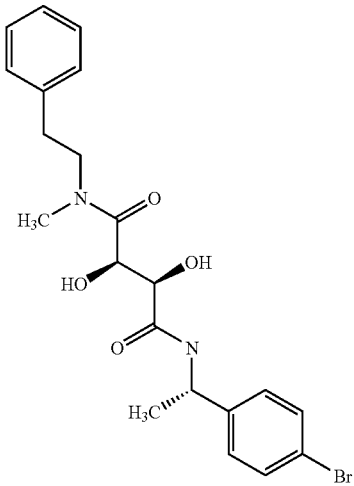 | B |
| 180 | 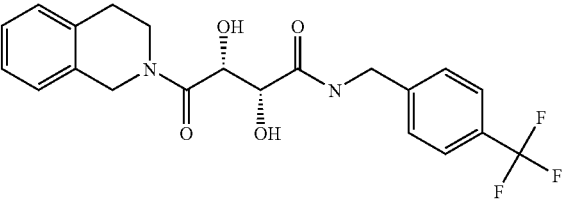 | B |
| 181 | 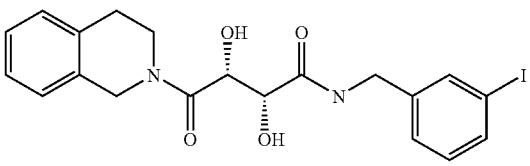 | D |
| 184 | 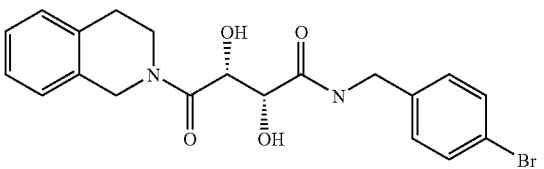 | B |
| 185 | 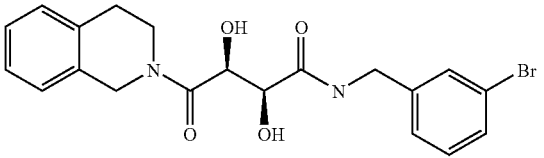 | D |
| 186 | 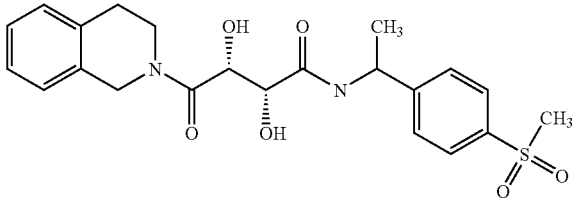 | D |

-continued

| S. No. | Structure | IC$_{50}$ rating |
|---|---|---|
| 187 | 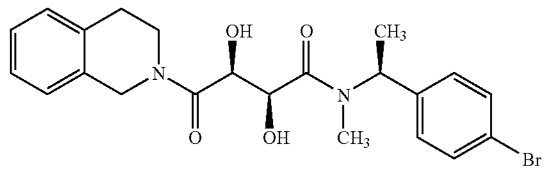 | D |
| 189 | 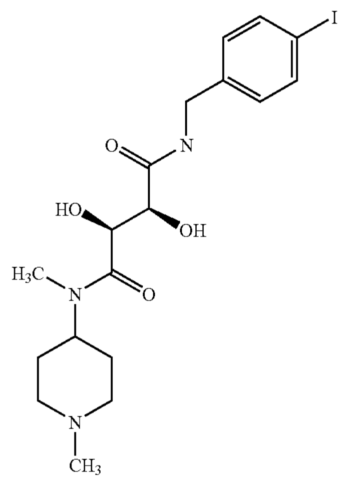 | D |
| 196 | 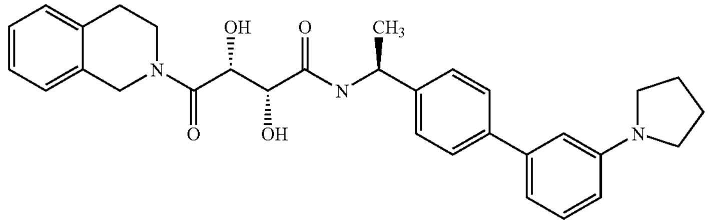 | A |
| 200 | 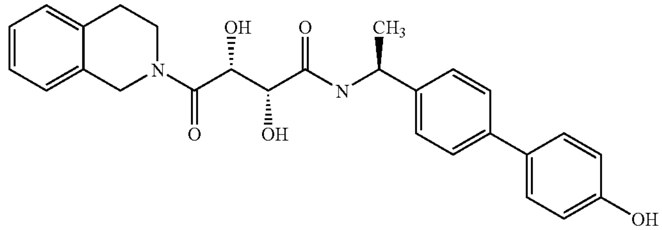 | A |
| 201 | 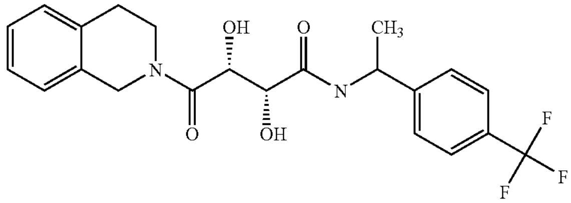 | B |
| 204 | 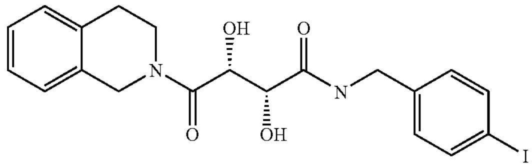 | A |

| S. No. | Structure | IC$_{50}$ rating |
|---|---|---|
| 206 | 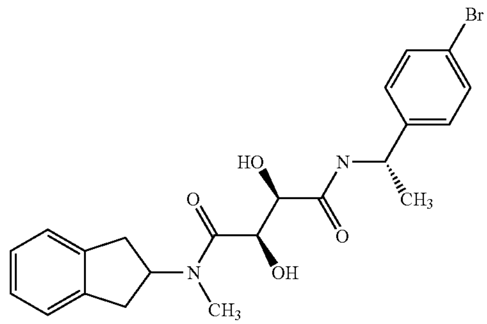 | B |
| 207 | 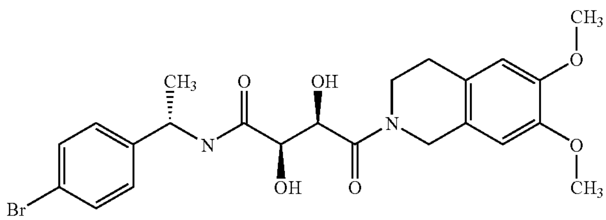 | A |
| 209 | 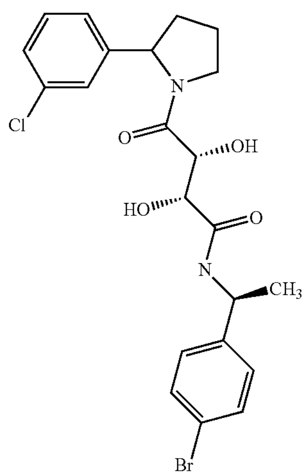 | A |
| 210 | 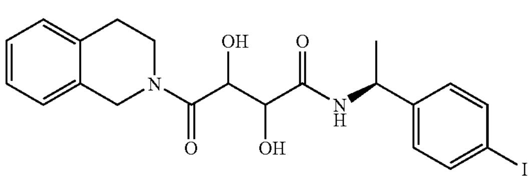 | B |
| 211 | 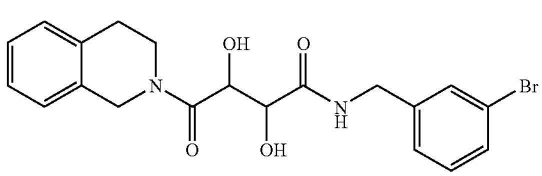 | D |
| 212 | 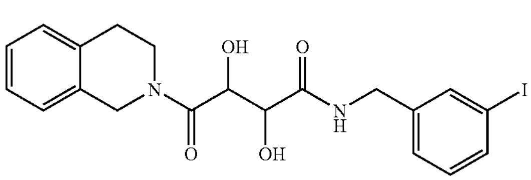 | D |

-continued

| S. No. | Structure | IC$_{50}$ rating |
|---|---|---|
| 215 | 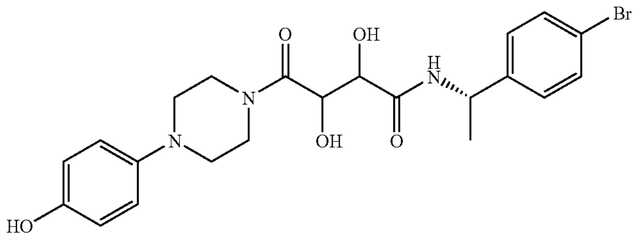 | C |
| 216 | 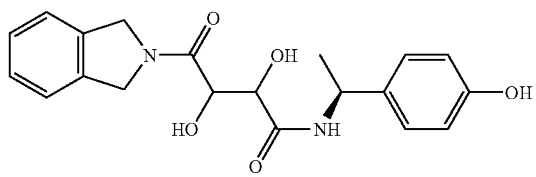 | A |
| 217 | 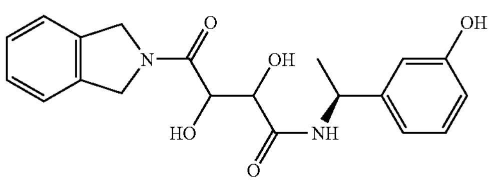 | C |
| 218 | 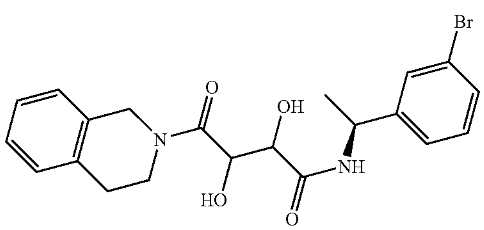 | D |
| 219 | 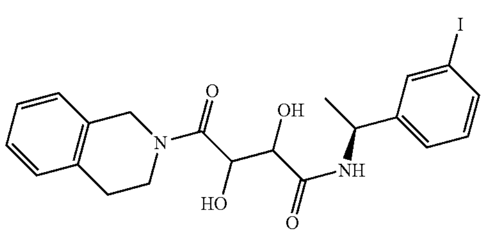 | C |
| 220 | 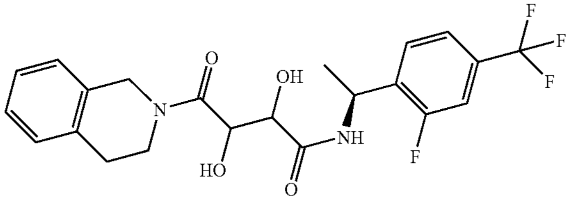 | D |

-continued
| S. No. | Structure | IC$_{50}$ rating |
|---|---|---|
| 221 | 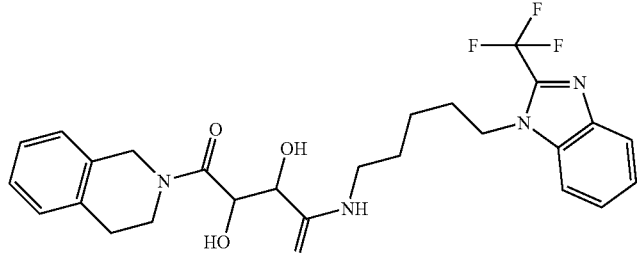 | D |
Representative examples of compounds of the invention with specific IC$_{50}$ values (ADMP inhibition) are listed in the table below:
| S. No. | Structure | IC$_{50}$ (μM) |
|---|---|---|
| 148 | 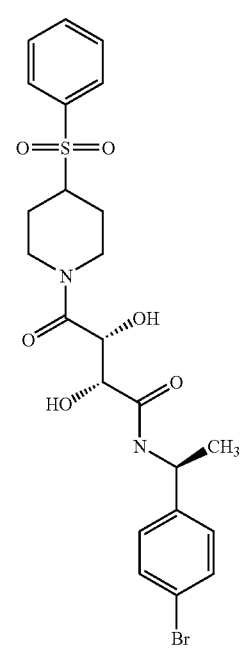 | 0.047 |

-continued
| S. No. | Structure | IC$_{50}$ (μM) |
|---|---|---|
| 143 | 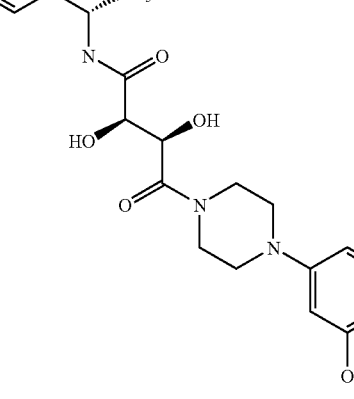 | 0.09 |
| 149 | 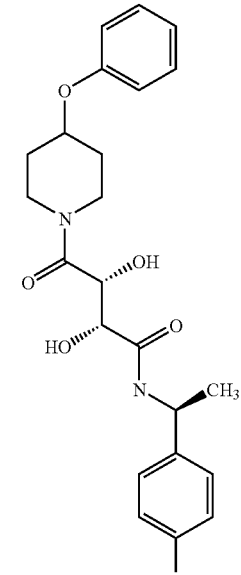 | 0.09 |
| 204 | 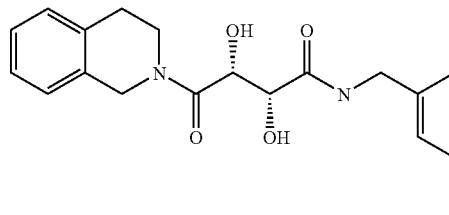 | 0.09 |
| 207 | 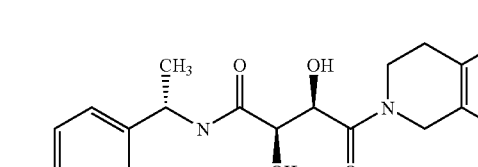 | 0.096 |

-continued

| S. No. | Structure | IC$_{50}$ (µM) |
|---|---|---|
| 160 | 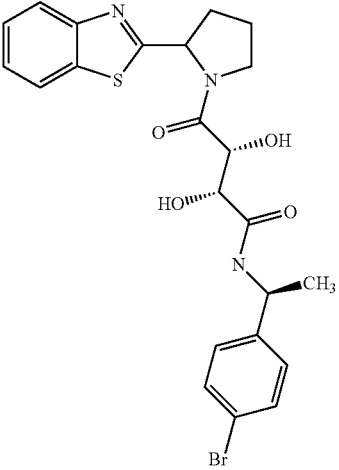 | 0.16 |
| 130 | 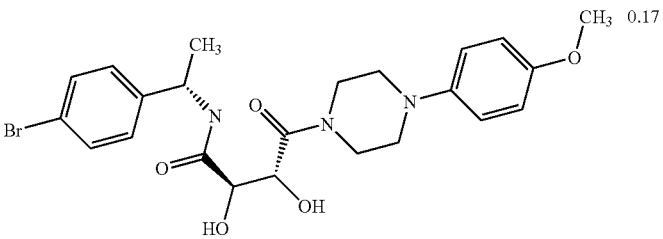 | 0.17 |
| 138 | 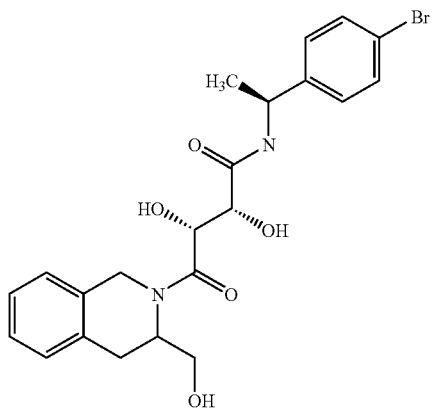 | 0.19 |

The pharmaceutical compositions containing the active ingredient may be in a form suitable for oral use, for example, as tablets, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for controlled release.

Formulations for oral use may also be presented as hard gelatin capsules wherein the active ingredients is mixed with an inert solid diluent, for example, calcium carbonate, calcium phosphate or kaolin, or a soft gelatin capsules where in the active ingredient is mixed with water or an oil medium, for example peanut oil, liquid paraffin or olive oil.

Aqueous suspensions contain the active material in admixture with excipients suitable for the manufacture of aqueous suspensions. Such excipients are suspending agents, for example, sodium carboxymethylcellulose, methylcellulose, hydroxypropylmethyl-cellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example, heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example, polyethylene sorbitan monooleate. The aqueous suspensions may also contain one or more preservatives, for example, ethyl or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example, arachis oil, olive oil, sesame oil or coconut oil, or in mineral oil such as liquid paraffin. The oily suspensions may contain a thickening agent, for example, beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, e.g., sweetening, flavoring and coloring agents, may also be present.

The pharmaceutical compositions of the invention may also be in the form of an oil-in-water emulsion. The oily phase may be a vegetable oil, e.g., olive oil or arachis oil, or a mineral oil, e.g., liquid paraffin or mixtures of these. Suitable emulsifying agents may be naturally-occurring phosphatides, e.g., soy beans, lecithin, and esters or partial esters derived from fatty acids and hexitol anhydrides, for example, sorbitan monooleate, and condensation products of the said partial esters with ethylene oxide, e.g., polyoxyethylene sorbitan monooleate. The emulsions may also contain sweetening and flavoring agents.

Syrups and elixirs may be formulated with sweetening agents, for example, glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, e.g., as a solution in 1,3-butane diol. Among the acceptable vehicles and solvents that may be employed are water, Ringer's solution and isotonic sodium chloride solution. In addition, sterile fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of the invention may also be administered in the form of suppositories for rectal administration of the drug. The compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compound of The invention are employed. (For purposes of this application, topical application shall include mouthwashes and gargles.)

The compounds for the present invention can be administered in the intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

The dosage regimen utilizing the compounds of the present invention is selected in accordance with a variety of factors including type, species, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter, arrest or reverse the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug. Preferably, doses of the compound of Formula I-IX useful in the method of the present invention range from 0.01 to 1000 mg per day. More preferably, dosages range from 0.1 to 1000 mg/day. Most preferably, dosages range from 0.1 to 500 mg/day. For oral administration, the compositions are preferably provided in the form of tablets containing 0.01 to 1000 milligrams of the active ingredient, particularly 0.01, 0.05, 0.1, 0.5, 1.0, 2.5, 5.0, 10.0, 15.0, 25.0, 50.0, 100 and 500 milligrams of the active ingredient for the symptomatic adjustment of the dosage to the patient to be treated. An effective amount of the drug is ordinarily supplied at a dosage level of from about 0.0002 mg/kg to about 50 mg/kg of body weight per day. The range is more particularly from about 0.001 mg/kg to 1 mg/kg of body weight per day.

Advantageously, the active agent of the present invention may be administered in a single daily dose, or the total daily dosage may be administered in dividend doses of two, three or four time daily.

The amount of active ingredient that may be combined with the carrier materials to produce single dosage form will vary depending upon the host treated and the particular mode of administration.

It will be understood, however, that the specific dose level for any particular patient will depend upon a variety of factors including the age, body weight, general health, sex, diet, time of administration, route or administration, rate of excretion, drug combination and the severity of the particular disease undergoing therapy.

The compounds of the invention may be produced by processes known to those skilled in the art and as shown in the following reaction schemes and in the preparations and examples described below.

EXAMPLES

The following abbreviations are used in the procedures and schemes:

| ACN | Acetonitrile |
|---|---|
| AcOH | Acetic acid |
| ADDP | 1,1¹-(Azodicarbonyl)dipiperidine |
| Anh. | Anhydrous |
| Aq | Aqueous |
| BOC | tert-Butoxycarbonyl |
| ° C. | degrees Celsius |
| CBZCl | Benzyl chloroformate |
| CDI | Carbodiimide |
| DBU | 1,8-Diazabicyclo[5.4.0]undec-7-ene |
| DCC | Dicyclohexylcarbodiimide |
| DCM | Dichloromethane |
| DEAD | Diethyl azodicarboxylate |
| (DHQ)2PHAL | Hydroquinine 1,4-phthalazinediyl diether |
| DIAD | Diisopropylazodicarboxylate |
| DIEA | Diisopropylethylamine |
| DMA | N,N-Dimethylacetamide |
| DMAP | 4-Dimethylaminopyridine |
| DME | Dimethoxyethane |
| DMF | Dimethylformamide |
| DMFDMA | N,N-Dimethylformamide dimethylacetal |
| DMPU | 1,3-Dimethyl-3,4,5,6-tetrahydro-2(1h)-pyrimidinone |
| DMSO | Dimethyl sulfoxide |
| EDC | 1-(3-Dimethylaminopropyl)-3-ethylcarbodiimide hydrochloride |
| EI | Electron ionization |
| Eq | Equivalents |
| EtOAc | Ethyl acetate |
| EtOH | Ethanol |
| g | grams |
| h. | hours |
| ¹H | proton |
| HATU | N,N,N',N'-Tetramethyl-O-(7-Azabenzotriazol-1-yl) Uronium hexafluorophosphate |
| Hex | hexanes |
| HOBt | 1-Hydroxybenzotriazole |
| HPLC | High pressure liquid chromatography |
| LAH | Lithium aluminum hydride |
| LDA | Lithium diisopropylamide |
| M | Molar |
| mCPBA | meta-Chloroperoxybenzoic acid |
| Me | Methyl |
| MeCN | Acetonitrile |
| MeOH | Methanol |
| min | Minutes |
| mg | Milligrams |
| MHz | Megahertz |
| ml | Milliliter |
| MS | Mass Spectroscopy |
| NMM | N-Methylmorpholine |
| NMP | 1-methyl-2-pyrrolidone |
| ON | Overnight |
| Pd(ᵗBu₃P)₂ | Bis-(tri-tert-butylophosphine)palladium |
| Pd(TPP)₄ | Tetrakis-(triphenylphosphine)palladium |
| Pd(Oac)₂ | Palladium(II) acetate |
| PdCl₂(TPP)₂ | Bis-(triphenylphosphine)palladium(II) chloride |
| PdCl₂(ddppf) | Dichloro[1,1'-bis(diphenylphosphino)ferrocene]palladium(ii) dichloride |
| Pd₂(dba)₃ | Tris(dibenzylideneacetone)dipalladium(0) |
| PyBrOP | Bromo-tris-pyrrolidino-phosphonium hexafluorophosphate |

-continued

| Pyr | Pyridine |
|---|---|
| RT | Room temperature |
| SiO₂ | Silica gel 60 chromatography |
| sgc | Silica gel 60 chromatography |
| tBOC | tert-Butoxycarbonyl |
| TACE | TNF-alpha converting enzyme |
| TEA | Triethylamine |
| TEA | Trifluoroacetic acid |
| THF | Tetrahydrofuran |
| TLC | Thin layer chromatography |
| TPP | Triphenylphosphine |
| $t_R$ | Retention time |

NMR spectra were acquired on a Mercuryplus 400 MHz NMR Spectrometer (Varian), using CDCl3 or DMSO-d6 as solvents. LC-MS data was obtained using an Agilent 1100 Series LC/MSD (quadrupole, API-ES (Atmospheric Pressure Interface Electrospray)) with a capillary voltage set to 3500 V and running in positive mode. Reported analytical HPLC (LC/MS) retention times were obtained using a C18 (150×4.6 mm) reverse-phase column eluting with a 5 or 10 minute gradient of 0.1% trifluoroacetic acid in water to 95:5 acetonitrile:water at a flow rate of 3 mL/min.

Purification via reverse phase chromatography was accomplished using a C18 reverse phase column with a gradient of 0.1% trifluoroacetic acid in water to 95:5 acetonitrile:water at a flow rate of 20 mL/min. Samples were collected using a UV (Gilson, 254 nm) or mass spectra (Agilent 1100 Series LC/MSD model SL) signal.

Normal phase silica gel chromatography on a Biotage instrument was accomplished using a Quad UV System (P/N 07052) utilizing KP-SIL 32-63 um columns, 60 Å with flash cartridges 12+M or 25+M.

The compounds of formula (I)-(IX) may be produced by processes known to those skilled in the art and as shown in the following reaction schemes and in the preparations and examples described below. These preparations and examples should not be construed to limit the scope of the disclosure. Alternate mechanistic pathways and analogous structures may be apparent to those skilled in the art. All kinds of isomeric forms of the compounds are considered to be within the scope of this invention.

EXAMPLES

Example 1

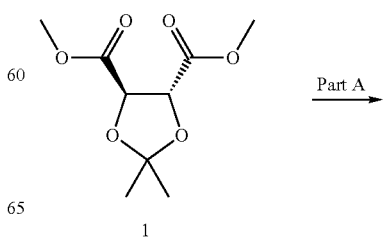

1

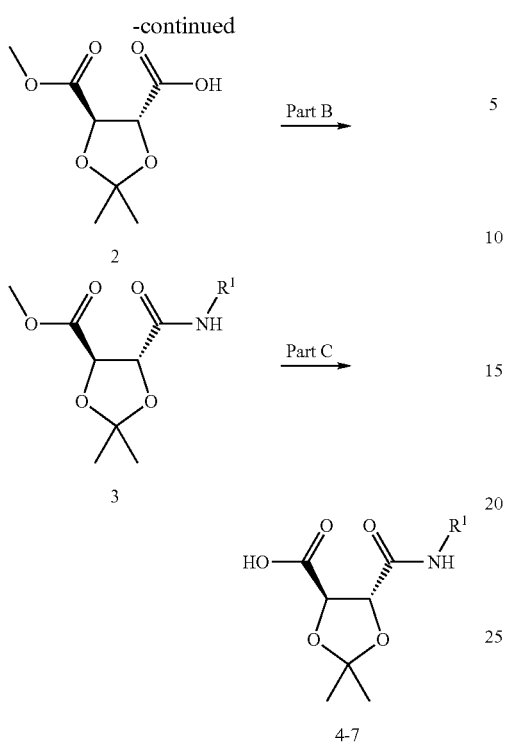

Part A:

To a stirred solution of L-tartrate dimethylester (1) (29.8 g, 136 mmol) in methanol (60 mL) at 0° C. (ice-bath) was added a solution of potassium hydroxide (6.9 g, 123 mmol) in water (20 mL) over 30 minutes. The reaction mixture was stirred at room temperature for 3 hours. The volatiles were removed in vacuo, water (40 mL) was added and the basic solution washed with diethyl ether (30 mL×3). The basic solution was acidified to pH 2.0 with 6N HCl, saturated with solid sodium chloride and the product extracted into diethyl ether (40 mL×4). Drying over magnesium sulfate and concentration afforded compound 2 (22.2 g, 79% yield) as a colorless oil.

Part B:

To a mixture of compound 2 (1.13 g, 5.53 mmol) and O-(7-Azabenzotriazol-1-yl)-N,N,N',N'-tetramethyluronium hexafluorophosphate (HATU) (3.2 g, 8.3 mmol) in DMF (20 mL) was added amine building block (1.2 equivalents) and diisopropylethylamine (2.89 mL, 16.59 mmol). The reaction mixture was stirred at room temperature for 3 hours. LC-MS analysis of the reaction indicated that the reaction was complete. The volatiles were removed in vacuo, ethyl acetate was added, and the organic solution washed successively with saturated NaHCO₃ (×1), water (×1), brine (×1), dried over magnesium sulfate and concentrated. Purification by flash column chromatography (SiO₂, 20% ethyl acetate in hexanes) afforded compound 3 (60-80% yield).

Part C:

A Mixture of compound 3 (850 mg, 3.9 mmol) and LiOH (1M, 5.85 mL, 5.85 mmol) in THF (30 mL) and water (10 mL) was stirred at room temperature for 5 hours. LC-MS analysis of the reaction indicated that the reaction was complete. The volatiles were removed in vacuo, water was added and the aqueous acidified to pH 4.0 with 1N HCl. The acidic solution was saturated with solid sodium chloride, the product extracted into ethyl acetate (×2), dried over magnesium sulfate and concentrated to afford compound 4-7 (60-70% yield).

The following scaffolds were synthesized using this procedure:

| Serial # | Structure | Exact mass | MS m/z (M⁺ + H) | Ret. Time (min) |
|---|---|---|---|---|
| 4 | 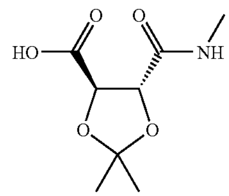 | 203.1 | 204.1 | 0.58 |
| 5 | 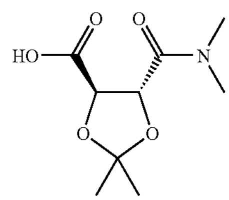 | 217.1 | 218.1 | 0.84 |
| 6 | 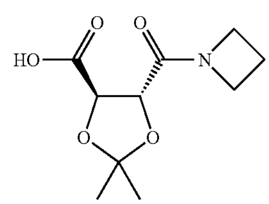 | 229.1 | 230.1 | 0.85 |
| 7 | 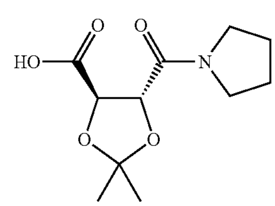 | 243.1 | 244.1 | 1.01 |

Example 2

Example 2A

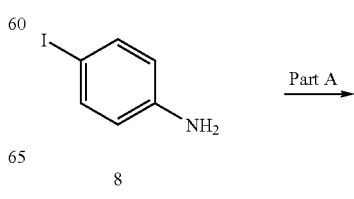

-continued

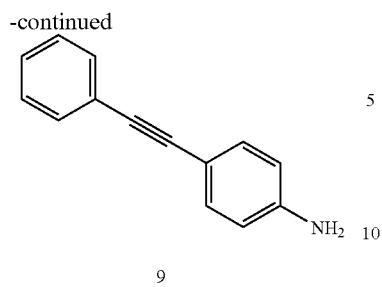

9

Part A:

To a mixture of 4-iodoaniline (8) (440 mg, 2 mmol), copper iodide (7.6 mg, 0.04 mmol) and dichlorobis(triphenylphosphine)palladium (II) (14 mg, 0.02 mmol) in THF (5 mL) was added phenylacetylene (244.8 mg, 2.4 mmol) and triethylamine (556 uL, 4 mmol). The reaction vessel was flushed with argon, and the reaction mixture stirred at room temperature for 16 hours. LC-MS analysis of the reaction indicated that the reaction was complete. Ethyl acetate (5 mL) was added, and the precipitates removed by passing through a plug of celite. The filtrate was concentrated, and the crude purified by flash column chromatography (SiO$_2$, 6% ethyl acetate in hexanes) to afford compound 9 as a brown solid (321 mg, 82% yield). HPLC-MS $t_R$=1.88 min (UV$_{254\ nm}$); mass calculated for formula C14H11N 193.1, observed LCMS m/z 194.1 (M+H).

Example 2B

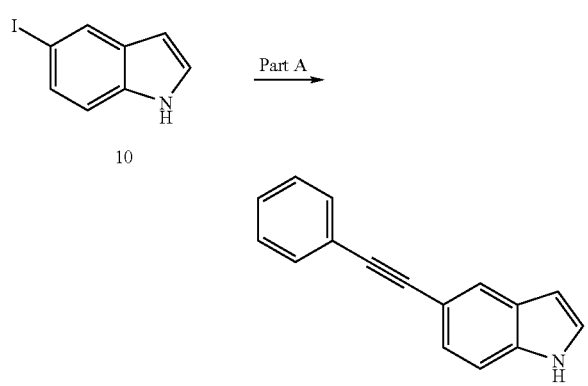

Part A:

Compound 11 was prepared from 5-iodoindole (10) using the Sonogashira Coupling conditions described in Example 2A, Part A. HPLC-MS $t_R$=2.06 min (UV$_{254\ nm}$); mass calculated for formula C16H11N 217.1, observed LCMS m/z 218.1 (M+H).

Example 2C

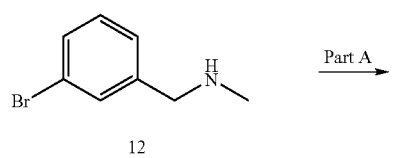

12

-continued

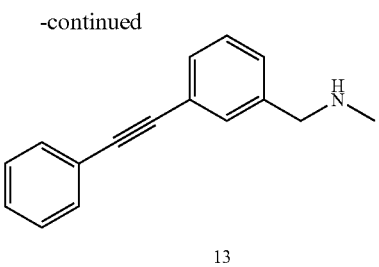

13

Part A:

To a mixture of 3-bromo-N-methylbenzylamine (12) (400 mg, 2 mmol), copper iodide (15.2 mg, 0.08 mmol) and dichlorobis(triphenylphosphine)palladium (II) (28 mg, 0.04 mmol) in DMF (3 mL) was added phenylacetylene (244.8 mg, 2.4 mmol) and triethylamine (556 uL, 4 mmol). The reaction vessel was flushed with argon, and the reaction mixture heated in the microwave for 5 minutes at 110° C. The volatiles were removed in vacuo, ethyl acetate was added, and the organic solution washed successively with saturated NaHCO$_3$ (×1), water (×1), brine (×1) and then extracted with 1N HCl. The acidic solution was basified to pH 9.0 with 1M NaOH, and then re-extracted with ethyl acetate, dried over magnesium sulfate and concentrated. Compound 13 was used without further purification. HPLC-MS $t_R$=1.24 min (UV$_{254\ nm}$); mass calculated for formula C16H15N 221.1, observed LCMS m/z 222.1 (M+H).

Example 2D

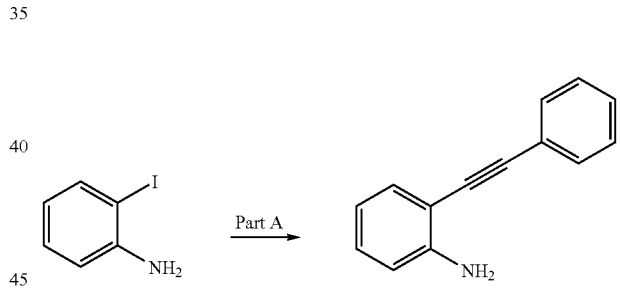

Part A:

Compound 15 was prepared from 2-iodoaniline (14) using the Sonogashira Coupling conditions described in Example 2A, Part A. HPLC-MS $t_R$=2.01 min (UV$_{254\ nm}$); mass calculated for formula C14H11N 193.1, observed LCMS m/z 194.1 (M+H).

Example 2E

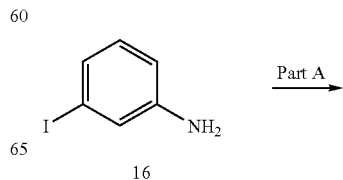

16

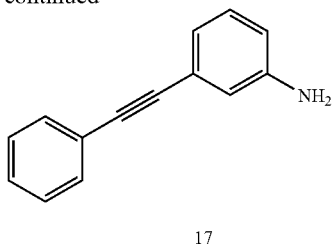

17

Part A:

Compound 17 was prepared from 3-iodoaniline (16) using the Sonogashira Coupling conditions described in Example 2A, Part A. HPLC-MS $t_R$=1.94 min (UV$_{254\ nm}$); mass calculated for formula C14H11N 193.1, observed LCMS m/z 194.1 (M+H).

Example 2F lamine (209 uL, 1.2 mmol). The reaction mixture was heated at 55° C. for 16 hours. Ethyl acetate (5 mL) was added, and the organic solution washed successively with saturated NaHCO$_3$ (×1), brine (×1), 0.5N HCl (×1), dried over magnesium sulfate and concentrated. Purification by flash column chromatography (SiO$_2$, 20% ethyl acetate in hexanes) afforded compound 19 as a white solid. HPLC-MS $t_R$=2.52 min (UV$_{254\ nm}$); mass calculated for formula C27H34N2O4 450.3, observed LCMS m/z 339.1 (M-(2×t-Bu)+H).

Part B:

To a solution of compound 19 (0.1 mmol) in dioxane (1 mL) at 0° C. (ice-bath) was added 4 N HCl in dioxane (2 mL) and water (0.2 mL). The reaction mixture was stirred at room temperature for 3 hours. LC-MS analysis of the reaction indicated that the reaction was complete. The volatiles were removed in vacuo, acetonitrile was added, concentrated and dried to afford compound 20 (100% yield) as a white solid. HPLC-MS $t_R$=1.32 min (UV$_{254\ nm}$); mass calculated for formula C18H18N2O2 294.1, observed LCMS m/z 295.1 (M+H).

Example 2G

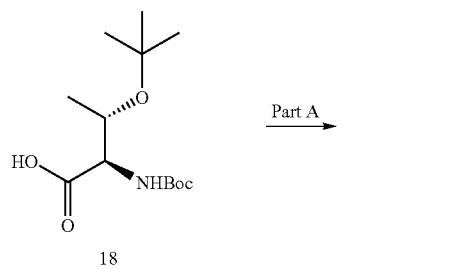

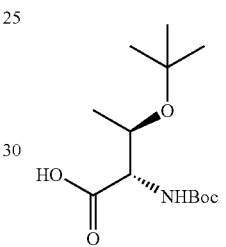

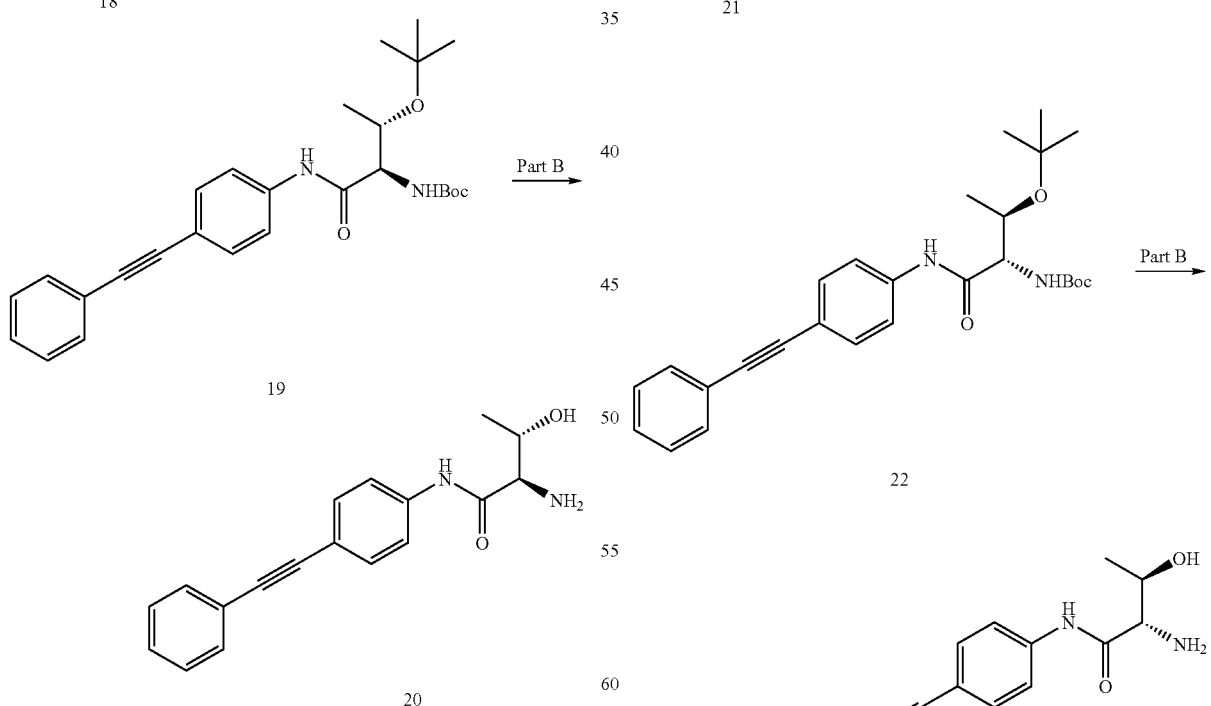

Part A:

To a mixture of Boc-D-Thr(t-Bu)-OH (100 mg, 0.36 mmol) and HATU (207 mg, 0.54 mmol) in NMP (2 mL) was added compound 9 (77 mg, 0.4 mmol) and diisopropylethy- Part A:

Compound 22 was prepared from Boc-L-Thr(t-Bu)-OH (21) and compound 9 using the coupling conditions described in Example 2F, Part A. HPLC-MS $t_R$=2.62 min (UV$_{254\ nm}$); mass calculated for formula C27H34N2O4 450.3, observed LCMS m/z 339.1 (M-(2×t-Bu)+H).

Part B:

Compound 23 was prepared from compound 22 using the hydrolysis conditions described in Example 2F, Part B. HPLC-MS $t_R$=1.35 min (UV$_{254\ nm}$); mass calculated for formula C18H18N2O2 294.1, observed LCMS m/z 295.1 (M+H).

Example 3

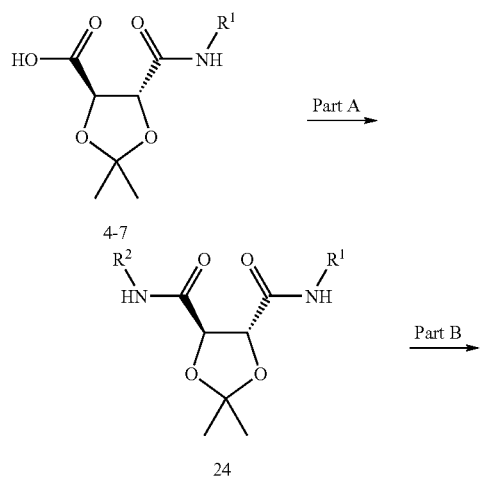

-continued

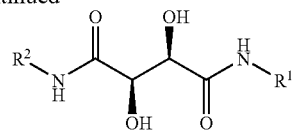

25-101

Part A:

To a mixture of monoacid (4-7) (25 mg, 0.12 mmol) and HATU (68 mg, 0.18 mmol) in NMP (2 mL) was added amine building block (1.2 equivalents) and diisopropylethylamine (69 uL, 0.40 mmol). The reaction mixture was heated at 55° C. for 16 hours. LC-MS analysis of the reaction indicated that the reaction was complete. The volatiles were removed in vacuo, ethyl acetate was added, and the organic solution washed successively with saturated NaHCO$_3$ (×1), water (×1), brine (×1), dried over magnesium sulfate and concentrated. Purification by Prep.LC afforded compounds 24 (80-90% yield).

Part B:

To a solution of compound 24 (0.1 mmol) in dioxane (1 mL) at 0° C. (ice-bath) was added 4 N HCl in dioxane (2 mL) and water (0.2 mL). The reaction mixture was stirred at room temperature for 3 hours. LC-MS analysis of the reaction indicated that the reaction was complete. The volatiles were removed in vacuo, acetonitrile was added, concentrated and dried to afford compounds 25-101 (100% yield). Purification by Prep-LC and conversion to a hydrochloric salt afforded compounds 25-101 as white solids.

The following ligands were synthesized using this procedure:

| Serial # | Structure | Exact mass | MS m/z (M⁺ + H) | Ret. Time (min) |
|---|---|---|---|---|
| 25 | 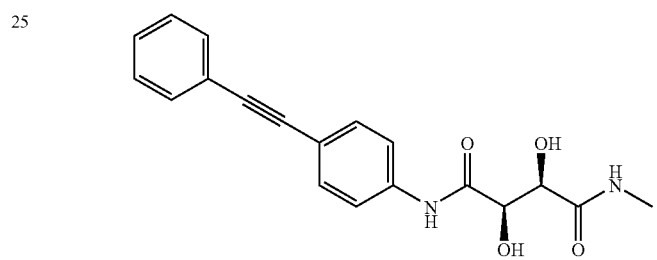 | 338.1 | 339.1 | 4.17 |
| 26 | 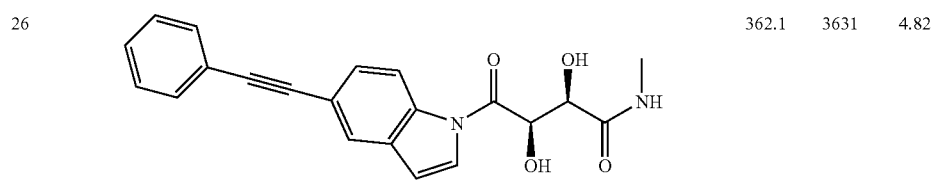 | 362.1 | 3631 | 4.82 |

-continued
| Serial # | Structure | Exact mass | MS m/z (M+ + H) | Ret. Time (min) |
|---|---|---|---|---|
| 27 | 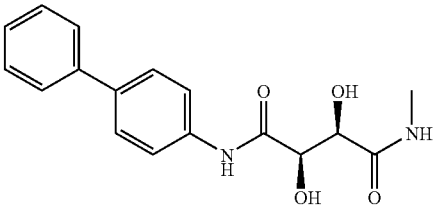 | 314.1 | 315.1 | 1.35 |
| 28 | 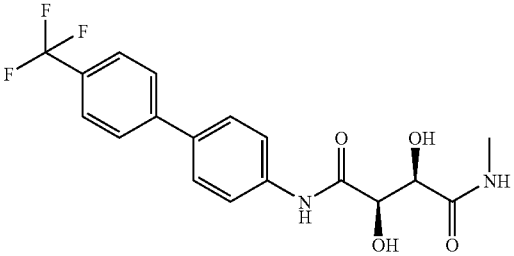 | 382.1 | 383.1 | 1.63 |
| 29 | 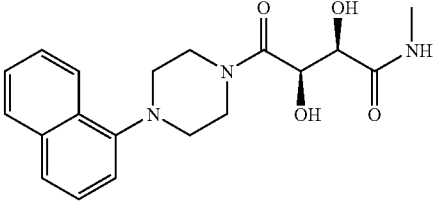 | 357.2 | 358.2 | 1.42 |
| 30 | 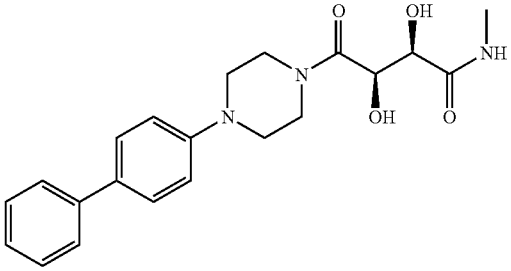 | 383.2 | 384.2 | 1.53 |
| 31 | 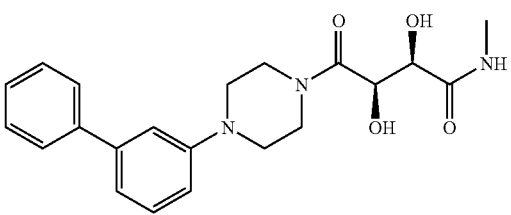 | 383.2 | 384.2 | 1.52 |
| 32 | 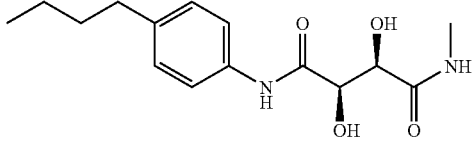 | 294.2 | 295.1 | 1.49 |
| 33 | 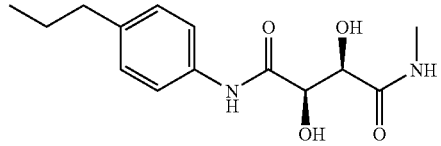 | 280.1 | 281.2 | 1.32 |

-continued

| Serial # | Structure | Exact mass | MS m/z (M⁺ + H) | Ret. Time (min) |
|---|---|---|---|---|
| 34 | 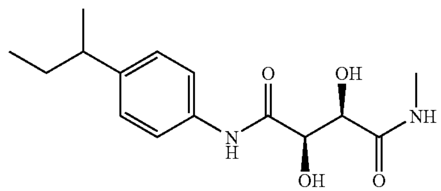 | 294.2 | 295.1 | 1.45 |
| 35 | 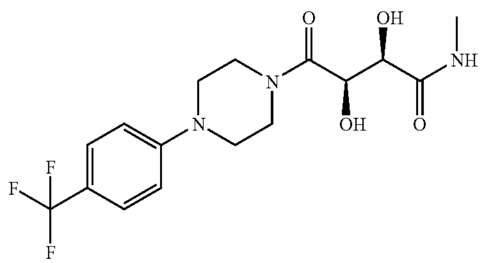 | 374.1 | 375.1 | 4.04 |
| 36 | 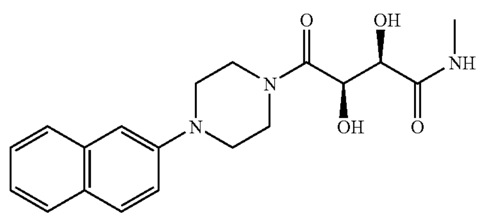 | 356.2 | 357.2 | 1.49 |
| 37 | 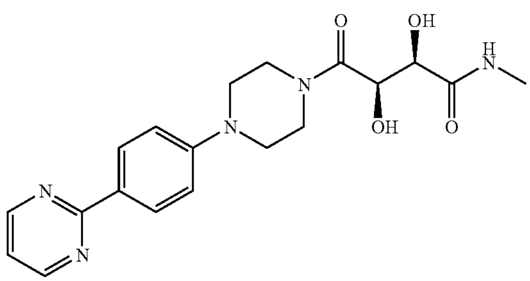 | 385.2 | 386.2 | 2.42 |
| 38 | 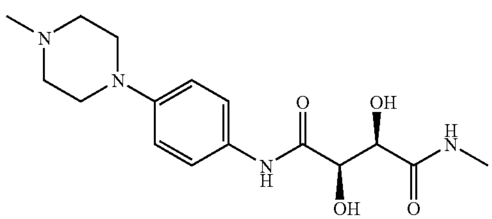 | 336.2 | 337.1 | 0.21 |
| 39 | 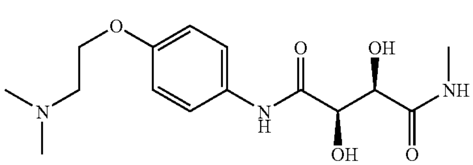 | 325.2 | 326.2 | 0.22 |
| 40 | 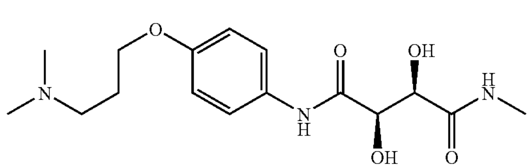 | 339.2 | 340.1 | 0.22 |

| Serial # | Structure | Exact mass | MS m/z (M+ + H) | Ret. Time (min) |
|---|---|---|---|---|
| 41 | 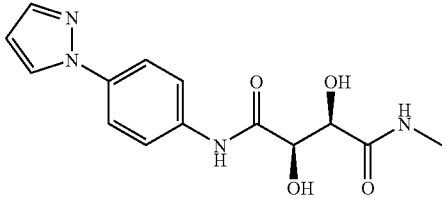 | 304.1 | 305.2 | 0.87 |
| 42 | 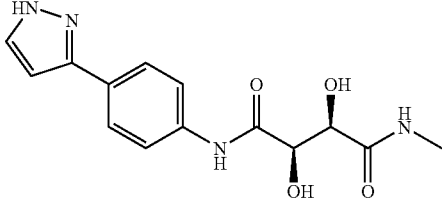 | 304.1 | 305.2 | 0.72 |
| 43 | 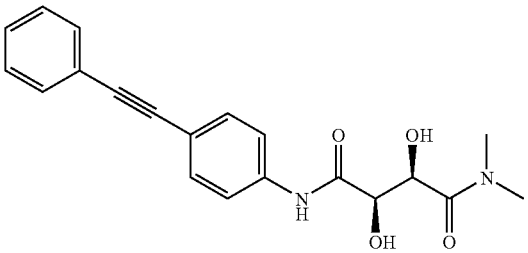 | 352.1 | 353.2 | 1.69 |
| 44 | 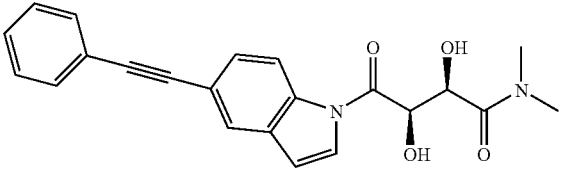 | 376.1 | 377.2 | 1.88 |
| 45 | 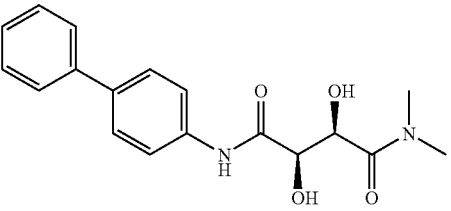 | 328.1 | 329.2 | 1.48 |
| 46 | 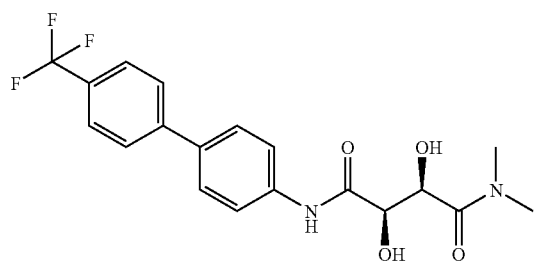 | 396.1 | 397.1 | 1.75 |

-continued

| Serial # | Structure | Exact mass | MS m/z (M+ + H) | Ret. Time (min) |
|---|---|---|---|---|
| 47 | 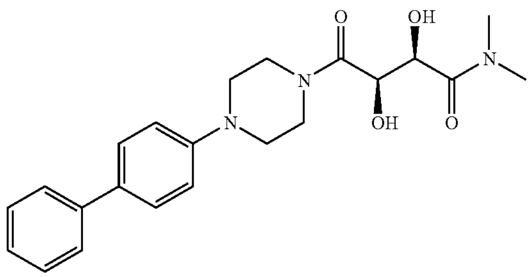 | 397.2 | 398.1 | 3.88 |
| 48 | 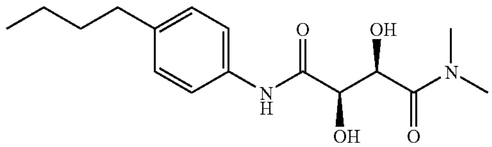 | 308.2 | 309.2 | 1.62 |
| 49 | 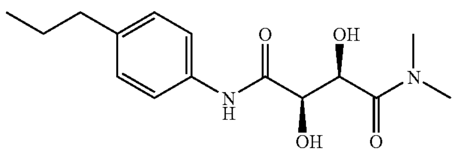 | 294.2 | 295.1 | 1.45 |
| 50 | 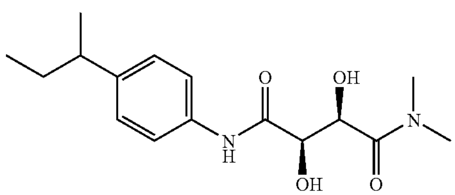 | 308.2 | 309.2 | 1.58 |
| 51 | 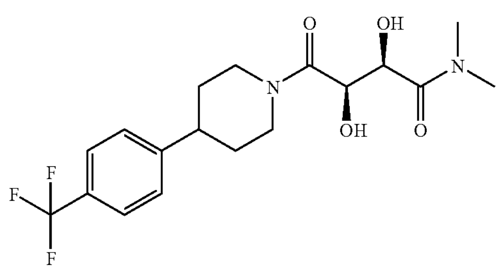 | 388.2 | 389.2 | 1.56 |
| 52 | 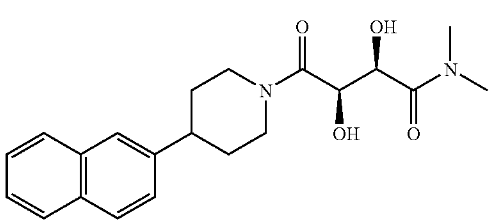 | 370.2 | 371.2 | 1.56 |
| 53 | 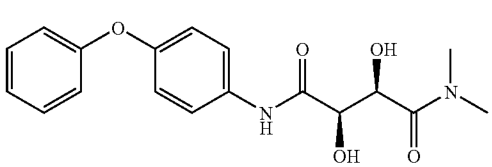 | 344.1 | 345.1 | 1.47 |

-continued

| Serial # | Structure | Exact mass | MS m/z (M+ + H) | Ret. Time (min) |
|---|---|---|---|---|
| 54 | 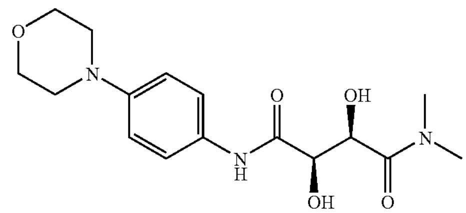 | 337.2 | 338.2 | 0.77 |
| 55 | 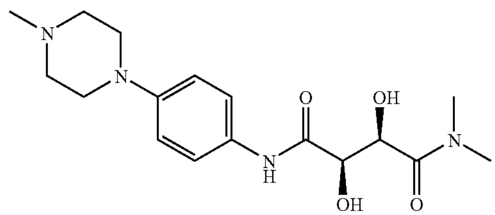 | 350.2 | 351.2 | 0.23 |
| 56 | 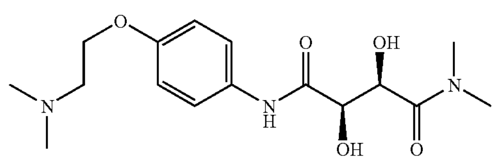 | 339.2 | 340.1 | 0.24 |
| 57 | 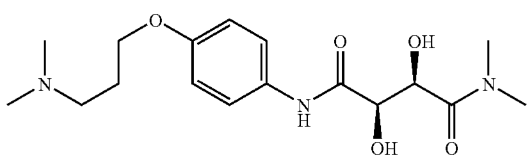 | 353.2 | 354.2 | 0.24 |
| 58 | 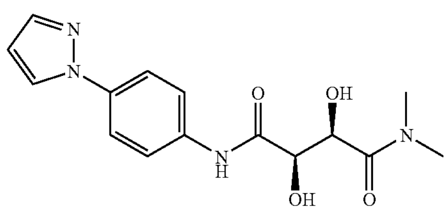 | 318.1 | 319.1 | 0.99 |
| 59 | 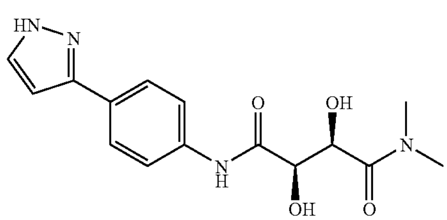 | 318.1 | 319.1 | 0.80 |
| 60 | 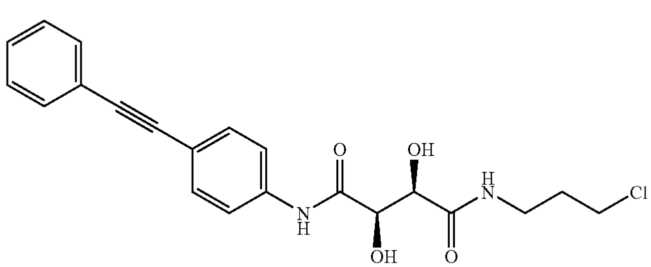 | 400.1 | 401.1 | 4.76 |

-continued

| Serial # | Structure | Exact mass | MS m/z (M⁺ + H) | Ret. Time (min) |
|---|---|---|---|---|
| 61 | 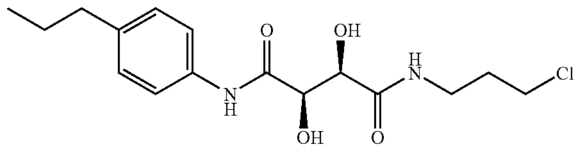 | 342.1 | 343.1 | 4.16 |
| 62 | 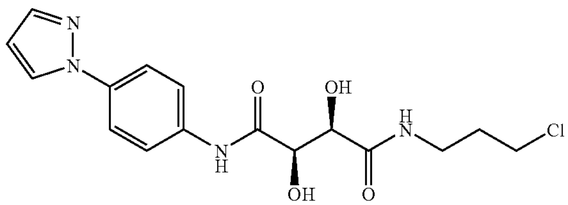 | 366.1 | 367.1 | 2.90 |
| 63 | 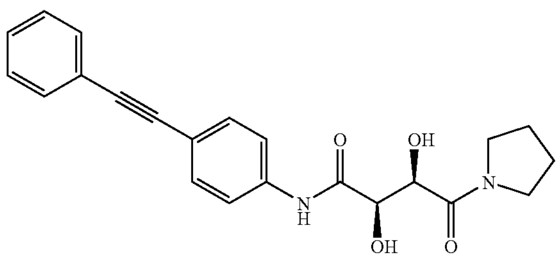 | 378.2 | 379.1 | 1.75 |
| 64 | 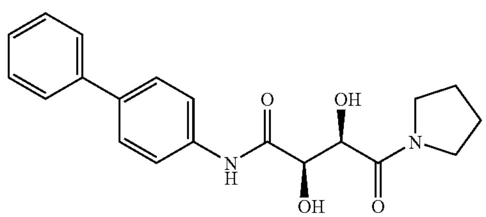 | 354.2 | 355.1 | 1.55 |
| 65 | 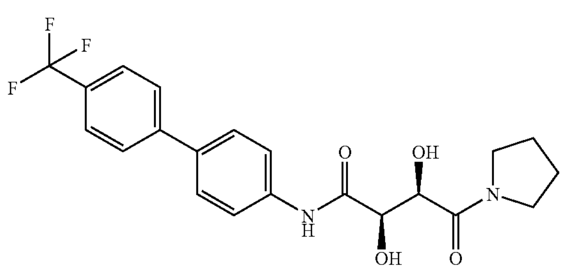 | 422.1 | 423.1 | 1.81 |
| 66 | 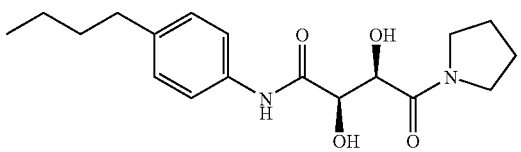 | 334.2 | 335.2 | 1.69 |
| 67 | 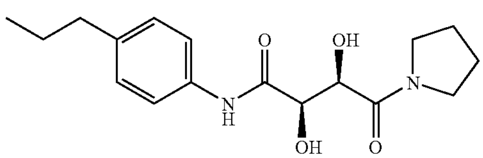 | 320.2 | 321.2 | 1.54 |

| Serial # | Structure | Exact mass | MS m/z (M⁺ + H) | Ret. Time (min) |
|---|---|---|---|---|
| 68 | 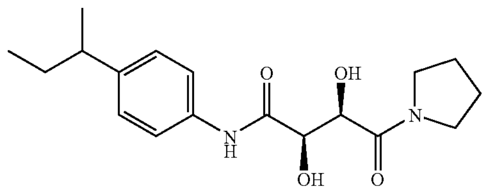 | 334.2 | 335.2 | 1.66 |
| 69 | 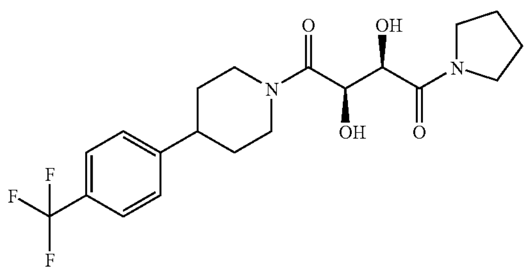 | 414.2 | 415.1 | 1.64 |
| 70 | 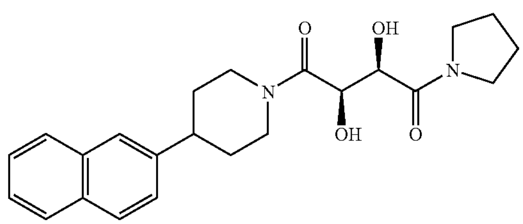 | 396.2 | 396.1 | 1.69 |
| 71 | 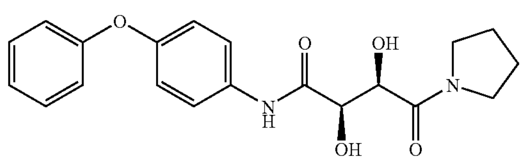 | 370.2 | 371.2 | 1.56 |
| 72 | 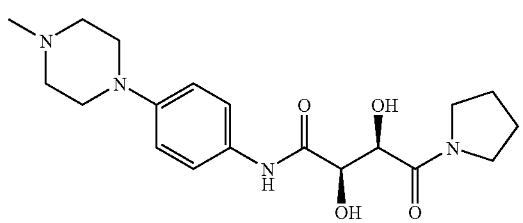 | 376.2 | 377.2 | 0.32 |
| 73 | 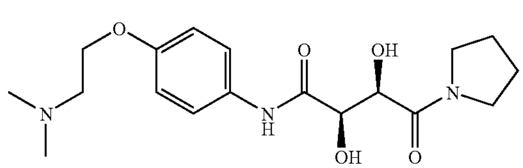 | 365.2 | 366.3 | 0.32 |
| 74 | 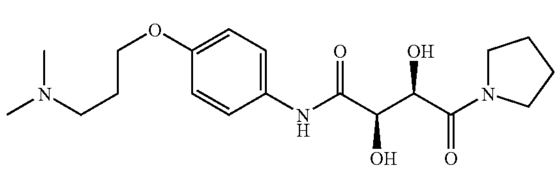 | 379.2 | 380.2 | 1.81 |

-continued
| Serial # | Structure | Exact mass | MS m/z (M⁺ + H) | Ret. Time (min) |
|---|---|---|---|---|
| 75 | 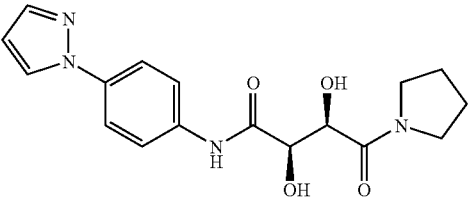 | 344.1 | 345.1 | 1.10 |
| 76 | 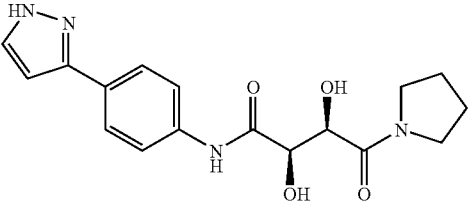 | 344.1 | 345.2 | 0.98 |
| 77 | 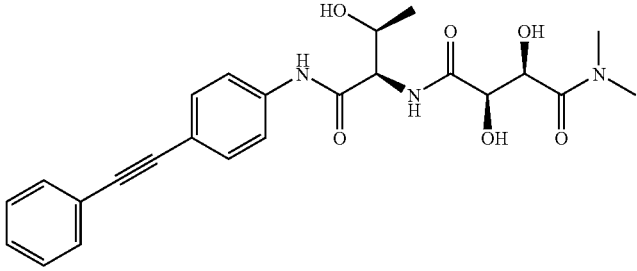 | 453.2 | 454.2 | 4.31 |
| 78 | 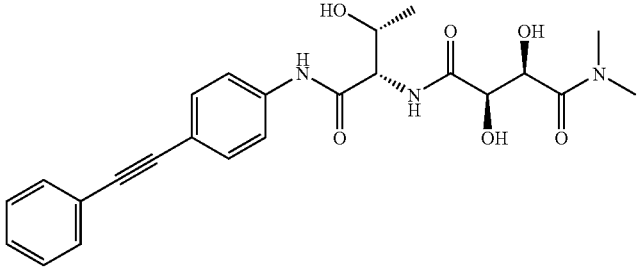 | 453.2 | 454.2 | 4.35 |
| 79 | 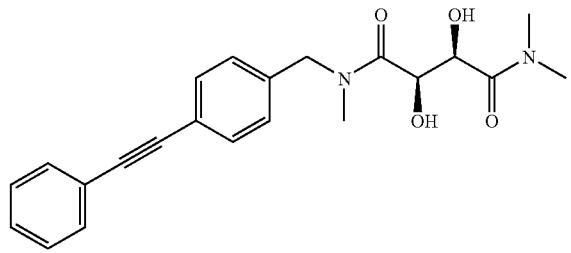 | 380.2 | 381.2 | 4.51 |
| 80 | 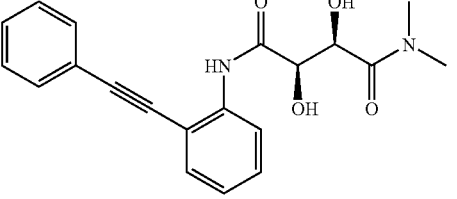 | 352.1 | 353.1 | 4.59 |

-continued

| Serial # | Structure | Exact mass | MS m/z (M⁺ + H) | Ret. Time (min) |
|---|---|---|---|---|
| 81 | 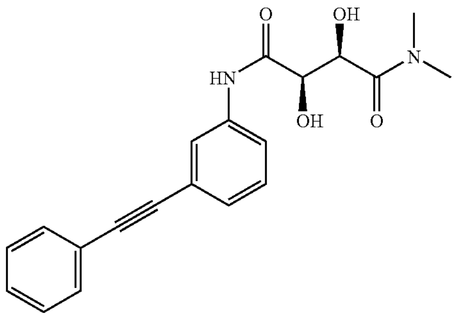 | 352.1 | 353.1 | 4.44 |
| 82 | 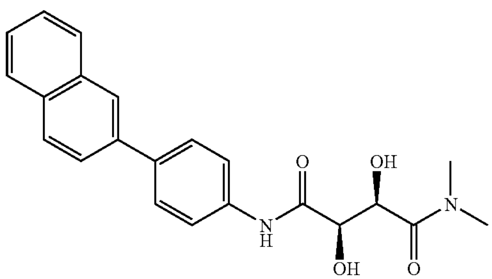 | 378.2 | 379.2 | 4.63 |
| 83 | 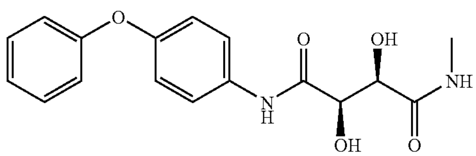 | 330.1 | 331.1 | 1.35 |
| 84 | 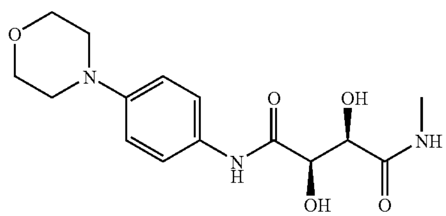 | 323.1 | 324.2 | 0.23 |
| 85 | 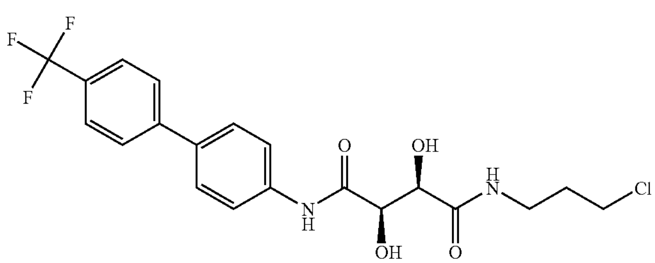 | 444.1 | 445.1 | 4.93 |
| 86 | 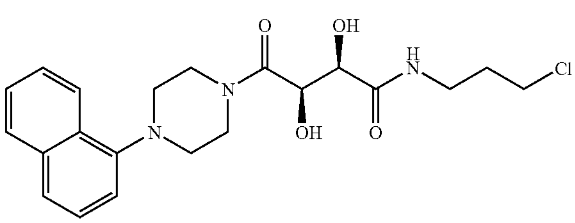 | 419.2 | 420.2 | 4.47 |

-continued

| Serial # | Structure | Exact mass | MS m/z (M+ + H) | Ret. Time (min) |
|---|---|---|---|---|
| 87 | 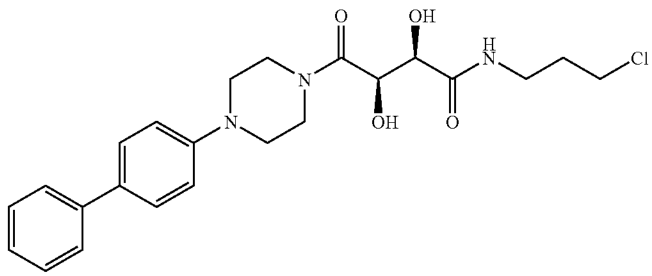 | 445.2 | 446.2 | 4.59 |
| 88 | 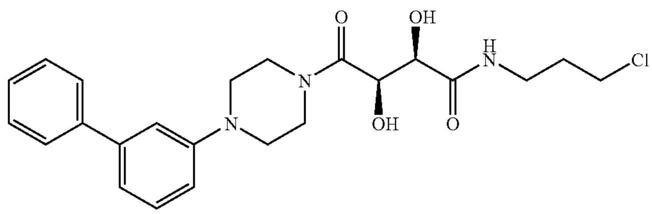 | 445.2 | 446.2 | 4.58 |
| 89 | 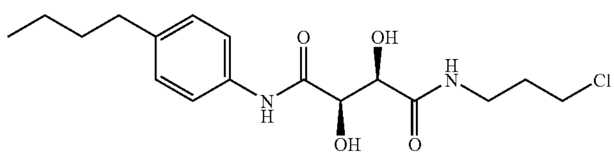 | 356.2 | 357.2 | 4.61 |
| 90 | 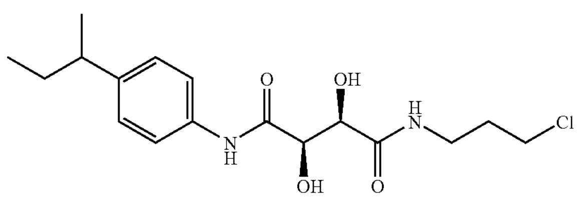 | 356.2 | 357.2 | 4.49 |
| 91 | 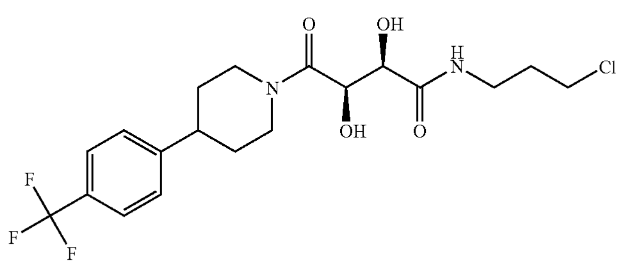 | 436.1 | 437.1 | 4.69 |
| 92 | 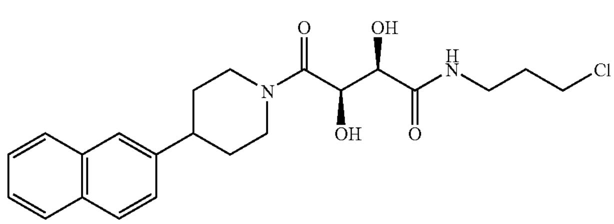 | 418.2 | 419.2 | 4.68 |
| 93 | 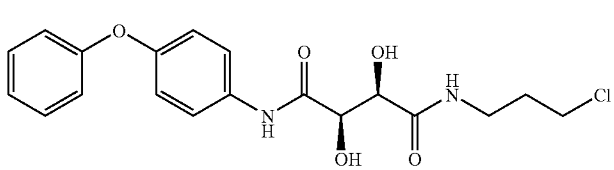 | 392.1 | 393.1 | 4.19 |

-continued

| Serial # | Structure | Exact mass | MS m/z (M⁺ + H) | Ret. Time (min) |
|---|---|---|---|---|
| 94 | 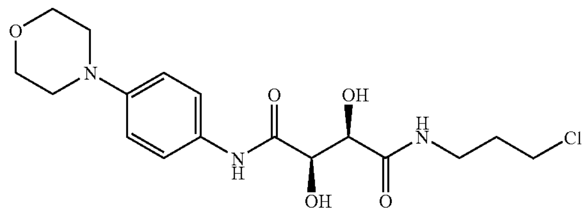 | 385.1 | 386.1 | 2.06 |
| 95 | 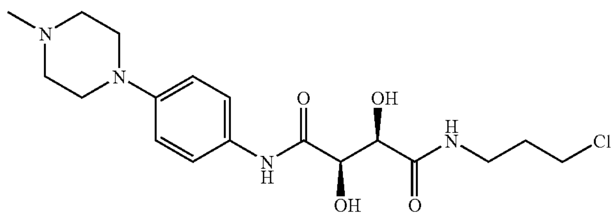 | 398.2 | 399.2 | 1.73 |
| 96 | 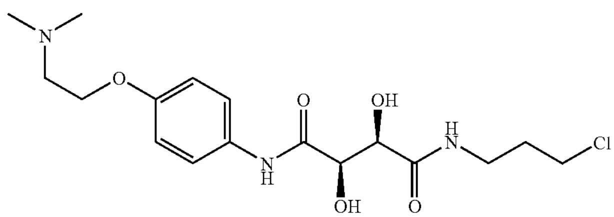 | 387.2 | 388.2 | 1.75 |
| 97 | 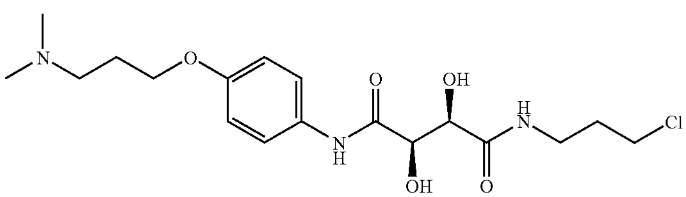 | 401.2 | 402.2 | 1.93 |
| 98 | 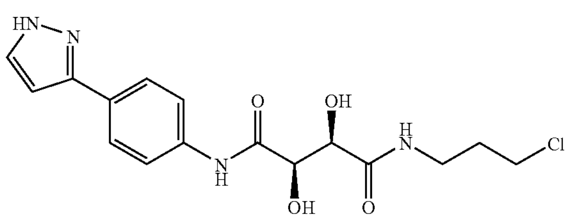 | 366.1 | 367.1 | 2.43 |
| 99 | 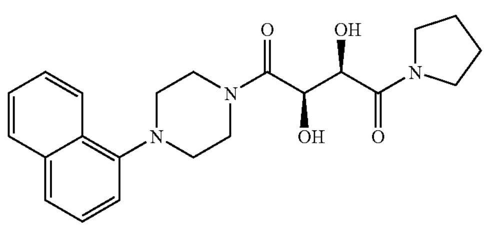 | 397.2 | 398.2 | 4.21 |
| 100 | 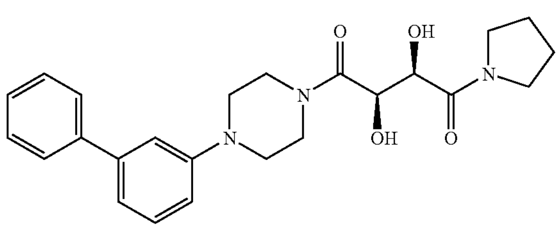 | 423.2 | 424.2 | 4.28 |

-continued

| Serial # | Structure | Exact mass | MS m/z (M⁺ + H) | Ret. Time (min) |
|---|---|---|---|---|
| 101 | 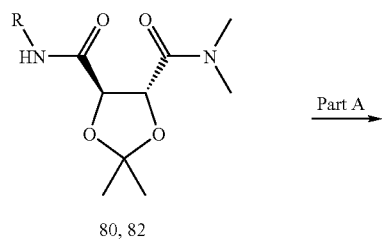 | 363.2 | 364.2 | 1.96 |

Example 4

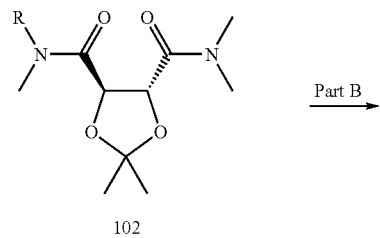

80, 82

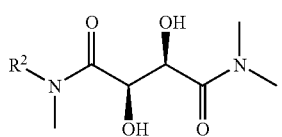

102

Part A:

To a mixture of compound 80 (28 mg, 0.071 mmol) and iodomethane (13.4 uL, 0.21 mmol) in THF (2 mL) was added sodium hydride (60% dispersion in oil, 3.1 mg, 0.079 mmol). The reaction mixture was stirred at room temperature for 3 hours. LC-MS analysis of the reaction indicated that the reaction was complete. Ethyl acetate was added, and the organic solution washed successively with saturated NaHCO₃ (×1), water (×1), brine (×1), dried over magnesium sulfate and concentrated. Compound 102 was used without further purification.

Part B:

Compounds 103 and 104 were prepared using the procedure described in Example 3, Part B.

The following ligands were synthesized using this procedure:

| Serial # | Structure | Exact mass | MS m/z (M⁺ + H) | Ret. Time (min) |
|---|---|---|---|---|
| 103 | (structure shown) | 366.2 | 367.2 | 4.31 |

-continued

| Serial # | Structure | Exact mass | MS m/z (M⁺ + H) | Ret. Time (min) |
|---|---|---|---|---|
| 104 | 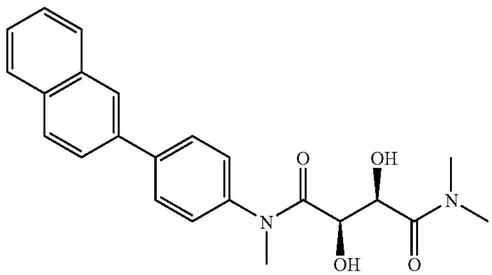 | 392.2 | 393.2 | 4.63 |

The following compounds in the table-2 can be prepared essentially following the procedures explained in Example 1, part A, B, C and Example 3 part A and B.

TABLE 2

| S. No. | Structure | MWt | MS m/z (M + H) | Retention time (min) |
|---|---|---|---|---|
| 105 | 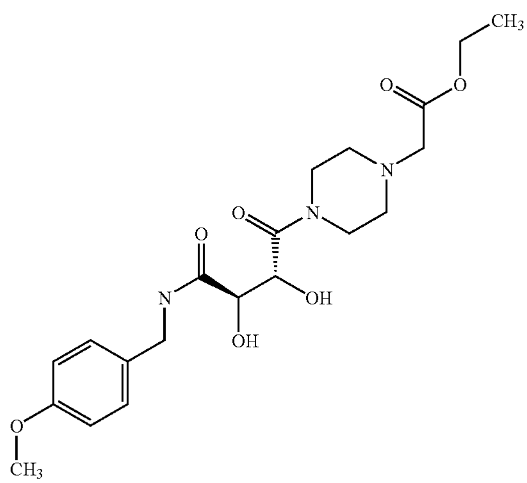 | 423.46 | 424.1 | 2.20 |
| 106 | 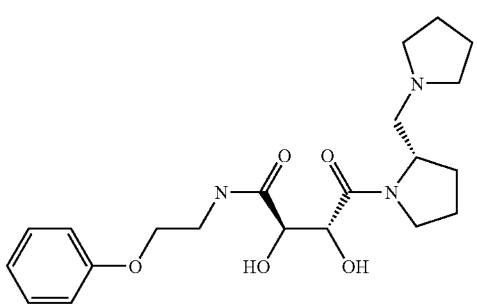 | 405.49 | 406.1 | 2.27 |

TABLE 2-continued

| S. No. | Structure | MWt | MS m/z (M + H) | Retention time (min) |
|---|---|---|---|---|
| 107 | 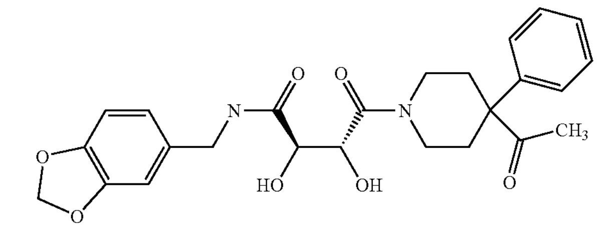 | 468.50 | 469.1 | 3.95 |
| 108 | 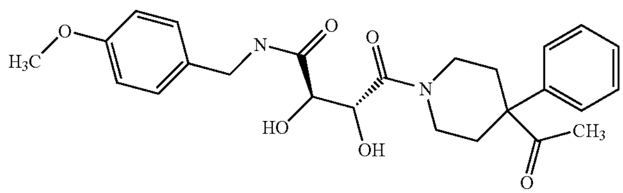 | 454.52 | 455.2 | 3.98 |
| 109 | 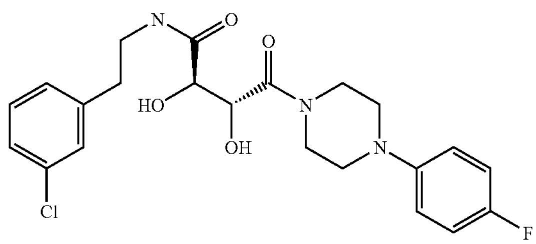 | 449.90 | 450.1 | 4.20 |
| 110 | 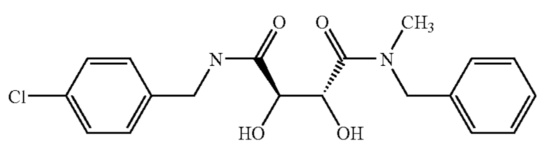 | 376.83 | 377.2 | 4.10 |
| 111 | 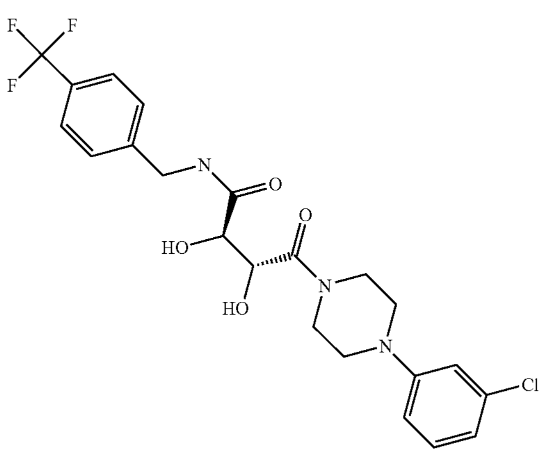 | 485.88 | 486.10 | 4.95 |

TABLE 2-continued

| S. No. | Structure | MWt | MS m/z (M + H) | Retention time (min) |
|---|---|---|---|---|
| 112 | 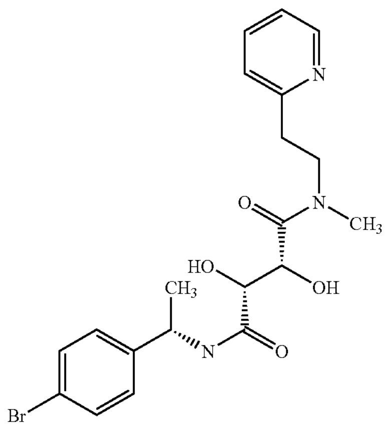 | 450.33 | 451.1 | 2.50 |
| 113 | 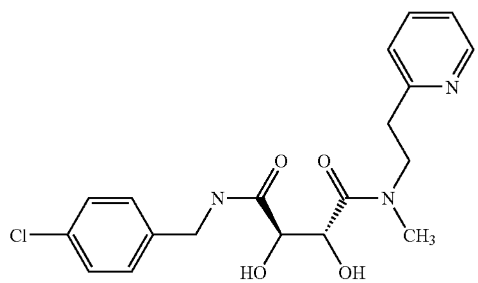 | 391.80 | 392.00 | 2.60 |
| 114 | 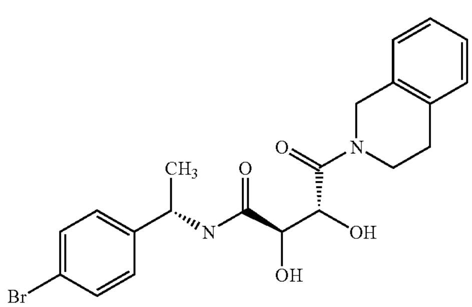 | 447.32 | 448.00 | 4.25 |
| 115 | 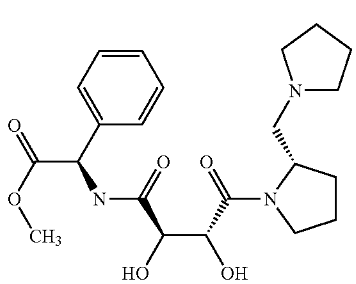 | 433.50 | 434.20 | 2.26 |

TABLE 2-continued

| S. No. | Structure | MWt | MS m/z (M + H) | Retention time (min) |
|---|---|---|---|---|
| 116 | 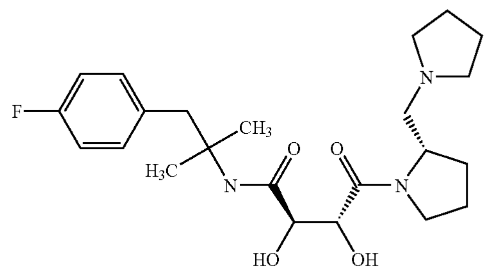 | 435.53 | 436.30 | 3.40 |
| 117 | 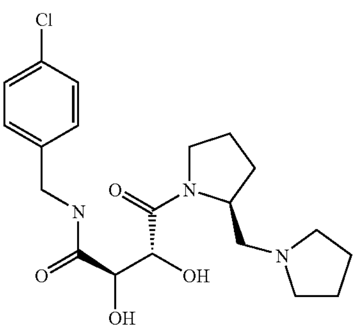 | 409.91 | 410.20 | 2.80 |
| 118 | 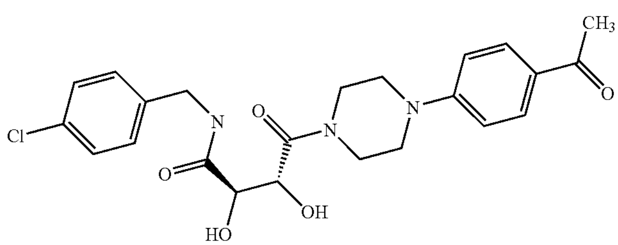 | 459.92 | 460.10 | 3.8 |
| 119 | 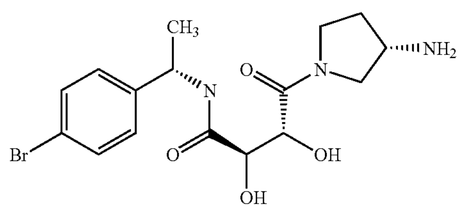 | 400.27 | 401.10 | 2.70 |
| 120 | 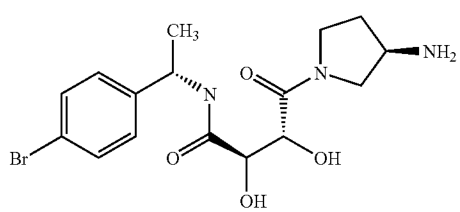 | 400.27 | 401.10 | 2.70 |

TABLE 2-continued

| S. No. | Structure | MWt | MS m/z (M + H) | Retention time (min) |
|---|---|---|---|---|
| 121 | 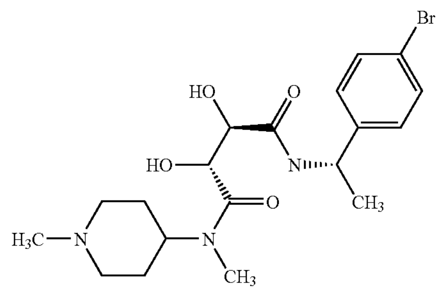 | 442.35 | 443.10 | 2.90 |
| 122 | 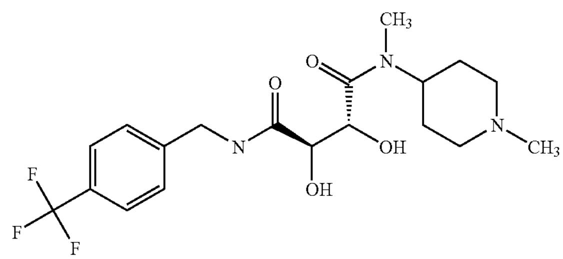 | 417.42 | 418.10 | 2.85 |
| 123 | 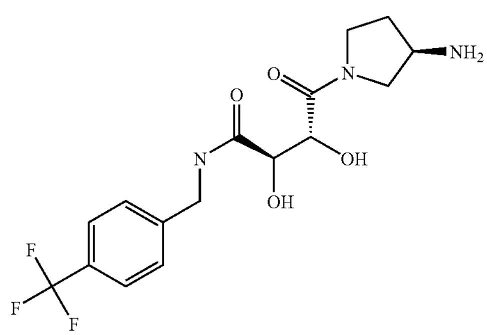 | 375.34 | 376.10 | 2.65 |
| 124 | 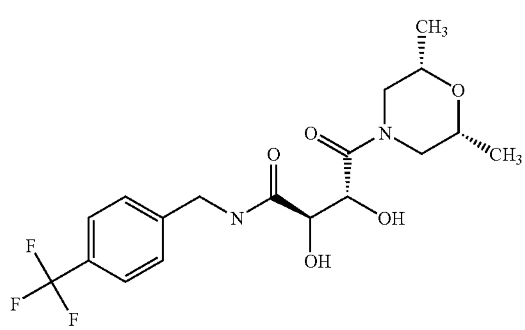 | 404.38 | 405.10 | 3.81 |
| 125 | 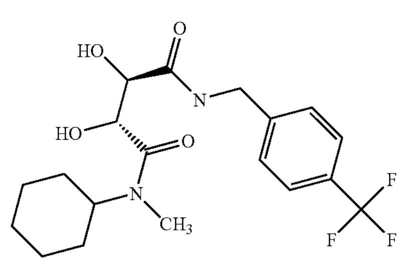 | 402.41 | 403.10 | 4.45 |

TABLE 2-continued

| S. No. | Structure | MWt | MS m/z (M + H) | Retention time (min) |
|---|---|---|---|---|
| 126 | 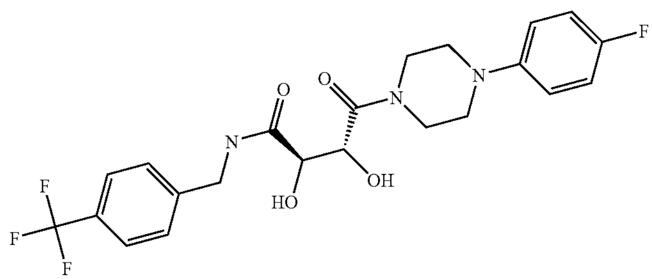 | 469.43 | 470.10 | 4.40 |
| 127 | 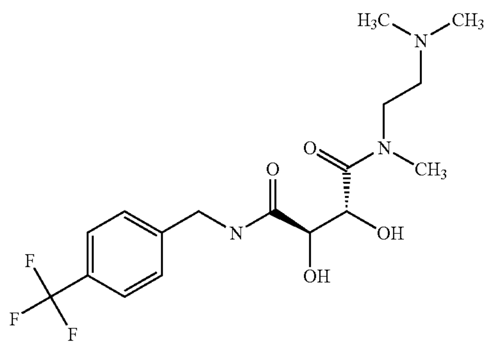 | 391.38 | 392.20 | 2.85 |
| 128 | 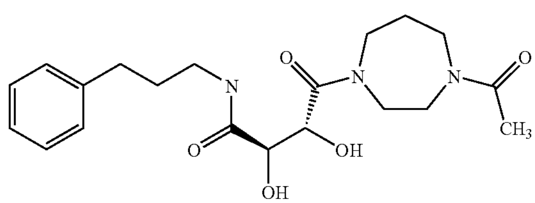 | 391.46 | 392.20 | 2.95 |
| 129 | 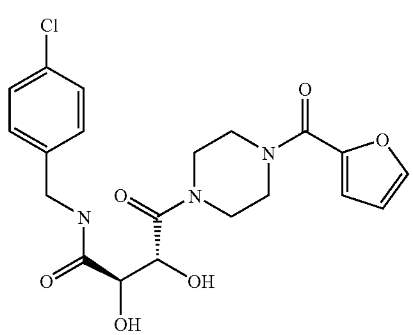 | 435.86 | 436.10 | 3.25 |
| 130 | 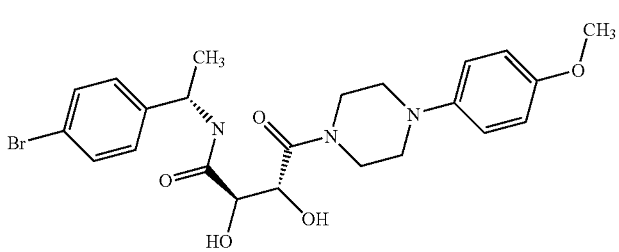 | 506.39 | 507.10 | 3.75 |

TABLE 2-continued

| S. No. | Structure | MWt | MS m/z (M + H) | Retention time (min) |
|---|---|---|---|---|
| 131 | 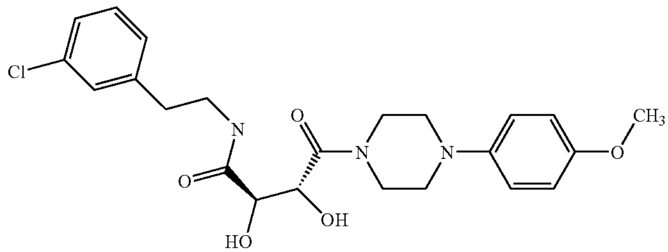 | 461.34 | 462.10 | 3.65 |
| 132 | 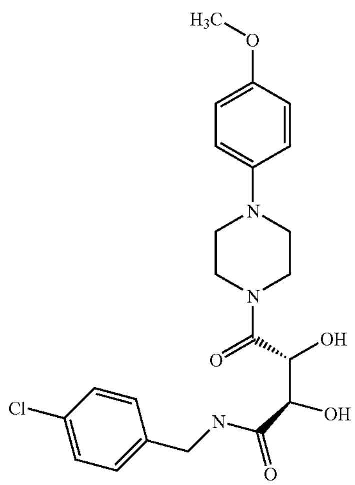 | 447.31 | 448.10 | 3.45 |
| 133 | 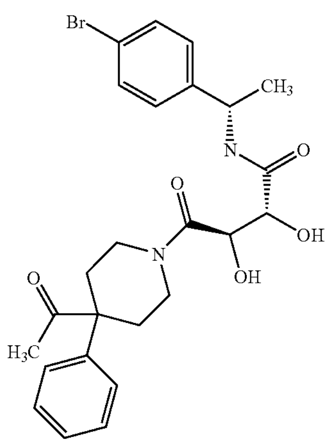 | 517.14 | 519.00 | 4.65 |
| 134 | 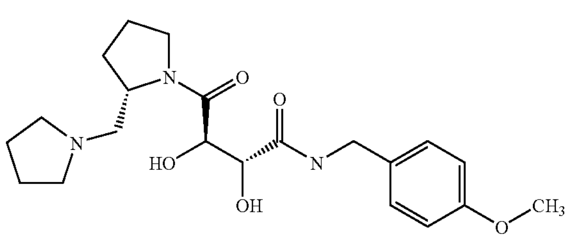 | 405.49 | 406.20 | 2.30 |

TABLE 2-continued

| S. No. | Structure | MWt | MS m/z (M + H) | Retention time (min) |
|---|---|---|---|---|
| 135 | 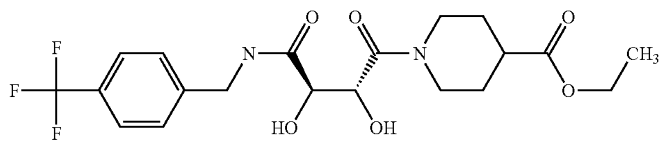 | 446.41 | 447.10 | 4.10 |
| 136 | 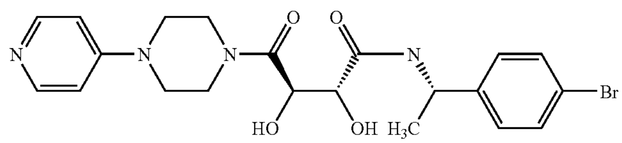 | 477.35 | 478.10 | 2.95 |
| 137 | 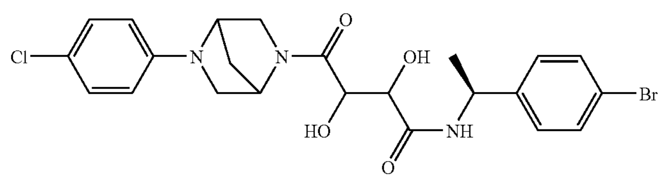 | 22.21 | 523.10 | 4.90 |
| 138 | 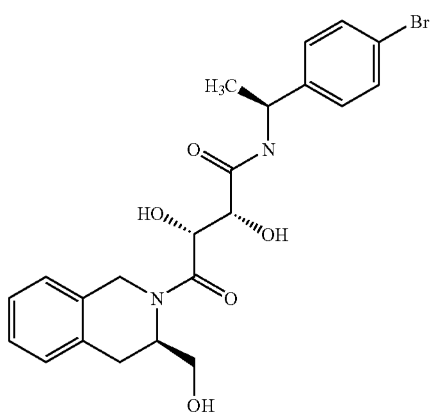 | 477.35 | 478.00 | 3.35 |
| 139 | 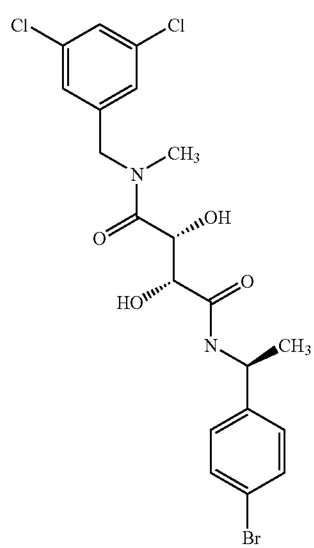 | 504.20 | 505.10 | 5.15 |

TABLE 2-continued

| S. No. | Structure | MWt | MS m/z (M + H) | Retention time (min) |
|---|---|---|---|---|
| 140 | 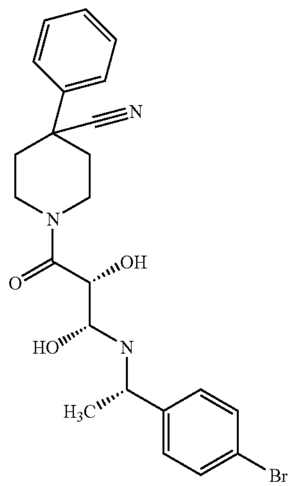 | 472.35 | 473.10 | 4.50 |
| 141 | 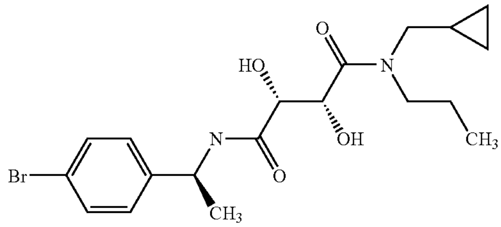 | 427.33 | 428.00 | 4.55 |
| 142 | 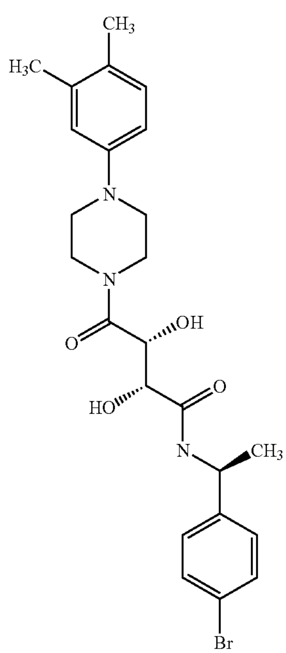 | 504.42 | 505.00 | 4.25 |

TABLE 2-continued

| S. No. | Structure | MWt | MS m/z (M + H) | Retention time (min) |
|---|---|---|---|---|
| 143 | 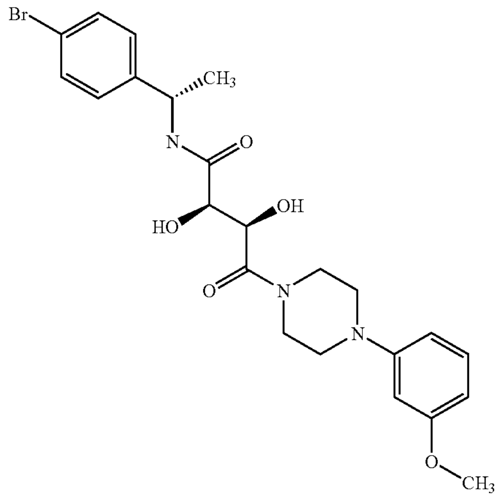 | 506.39 | 507.10 | 4.28 |
| 144 | 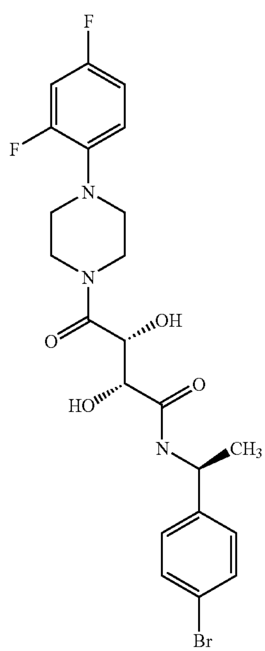 | 512.34 | 513.10 | 4.75 |

TABLE 2-continued
| S. No. | Structure | MWt | MS m/z (M + H) | Retention time (min) |
|---|---|---|---|---|
| 145 | 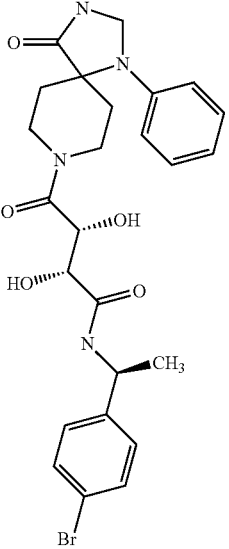 | 545.43 | 546.10 | 4.20 |
| 146 | 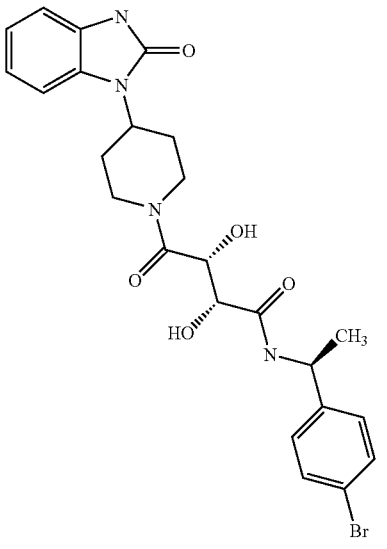 | 531.40 | 532.00 | 3.85 |

TABLE 2-continued
| S. No. | Structure | MWt | MS m/z (M + H) | Retention time (min) |
|---|---|---|---|---|
| 147 | 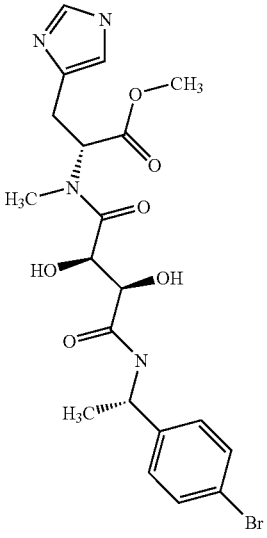 | 497.34 | 498.10 | 4.00 |
| 148 | 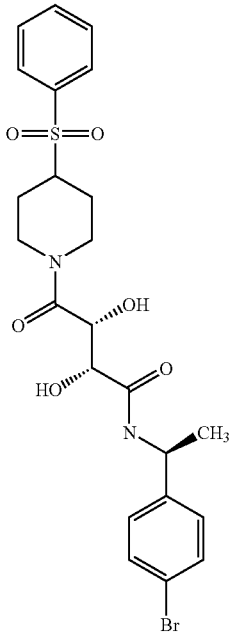 | 539.44 | 540.10 | 4.05 |

TABLE 2-continued

| S. No. | Structure | MWt | MS m/z (M + H) | Retention time (min) |
|---|---|---|---|---|
| 149 | 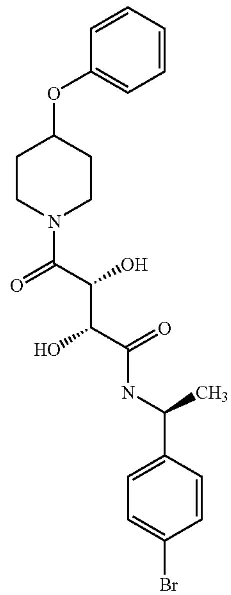 | 491.37 | 492.10 | 4.75 |
| 150 | 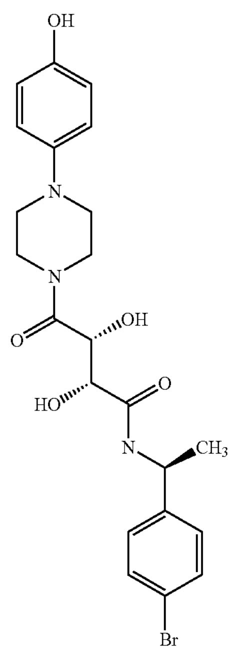 | 492.36 | 493.10 | 3.00 |
| 151 | 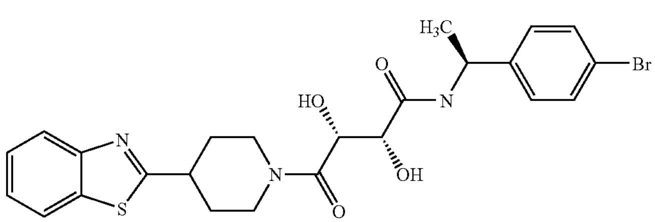 | 532.45 | 533.10 | 4.60 |

TABLE 2-continued

| S. No. | Structure | MWt | MS m/z (M + H) | Retention time (min) |
|---|---|---|---|---|
| 152 | 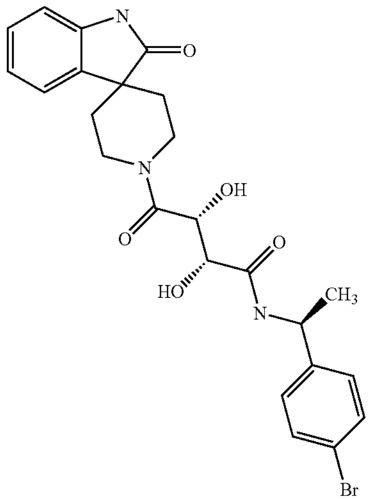 | 516.38 | 517.10 | 3.95 |
| 153 | 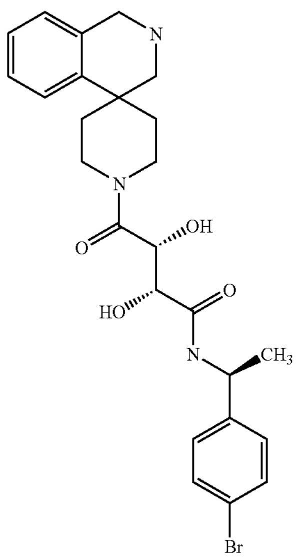 | 516.43 | 517.10 | 3.25 |
| 154 | 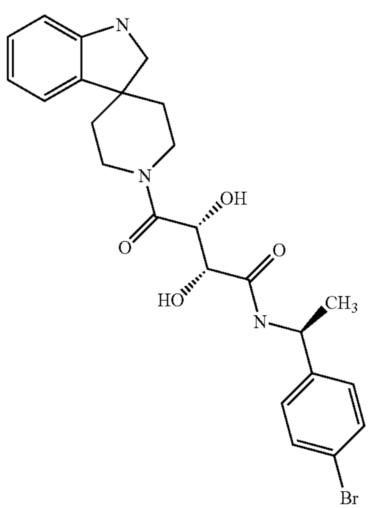 | 502.40 | 503.10 | 3.25 |

TABLE 2-continued
| S. No. | Structure | MWt | MS m/z (M + H) | Retention time (min) |
|---|---|---|---|---|
| 155 | 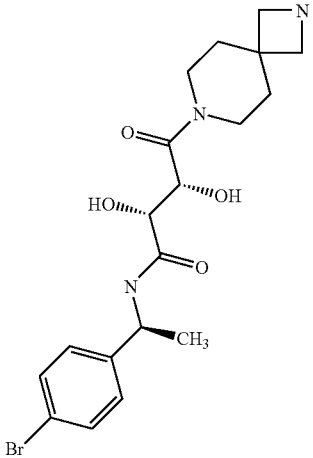 | 440.33 | 441.20 | 2.80 |
| 156 | 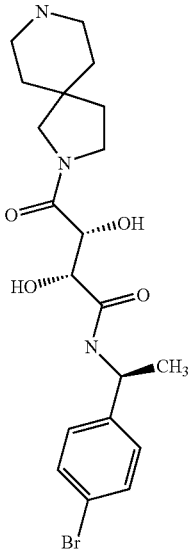 | 454.36 | 455.10 | 2.75 |

TABLE 2-continued
| S. No. | Structure | MWt | MS m/z (M + H) | Retention time (min) |
|---|---|---|---|---|
| 157 | 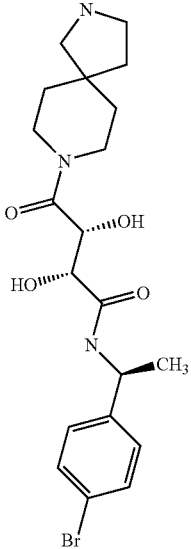 | 454.36 | 455.00 | 2.85 |
| 158 | 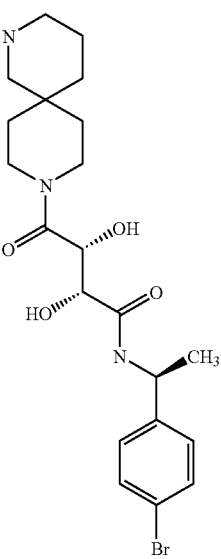 | 468.38 | 469.10 | 2.95 |

TABLE 2-continued
| S. No. | Structure | MWt | MS m/z (M + H) | Retention time (min) |
|---|---|---|---|---|
| 159 | 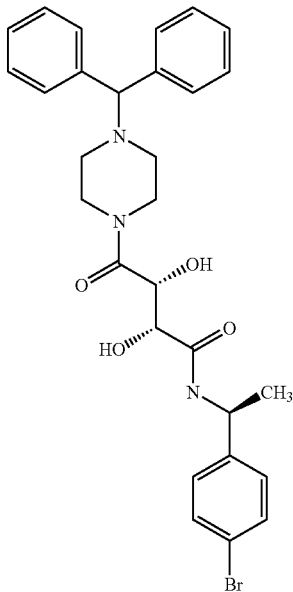 | 566.49 | 567.10 | 4.00 |
| 160 | 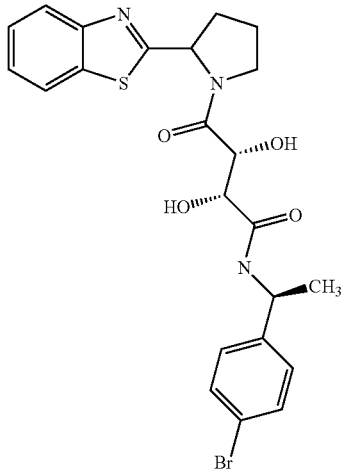 | 518.43 | 519.10 | 4.50 |
| 161 | 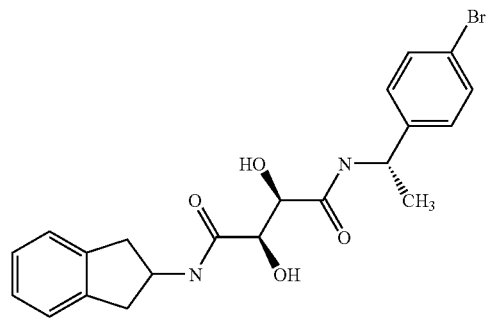 | 447.32 | 449.10 | 4.20 |

TABLE 2-continued

| S. No. | Structure | MWt | MS m/z (M + H) | Retention time (min) |
|---|---|---|---|---|
| 162 | 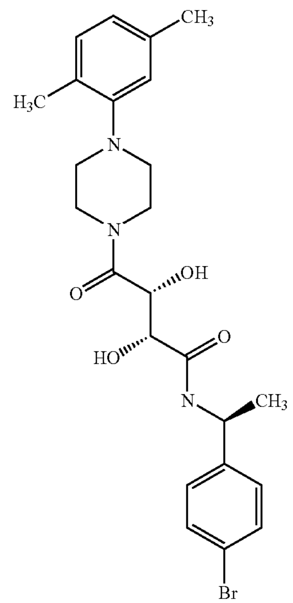 | 504.40 | 505.10 | 5.00 |
| 163 | 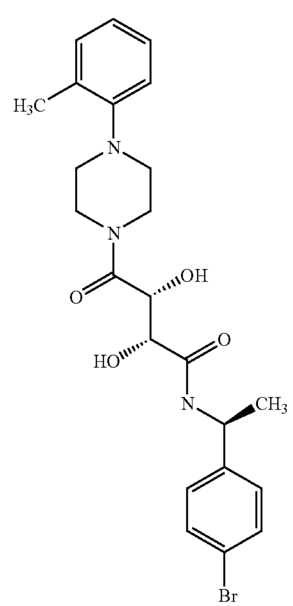 | 490.39 | 491.10 | 4.7 |
| 164 | 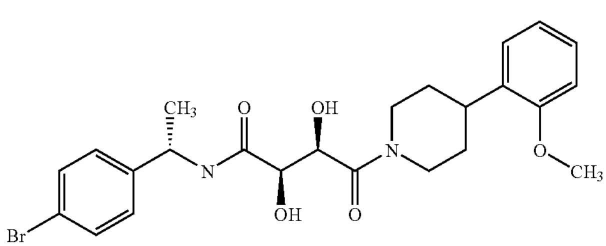 | 506.39 | 507.10 | 3.75 |

TABLE 2-continued
| S. No. | Structure | MWt | MS m/z (M + H) | Retention time (min) |
|---|---|---|---|---|
| 165 | 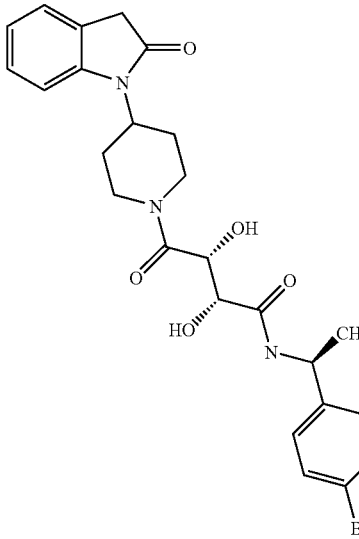 | 530.41 | 531.10 | 4.15 |
| 166 | 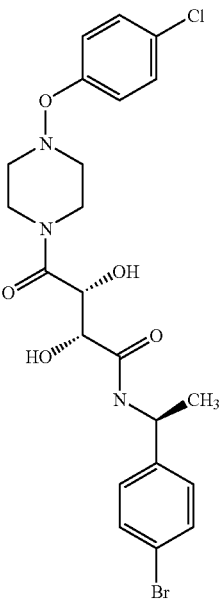 | 525.42 | 526.10 | 5.00 |
| 167 | 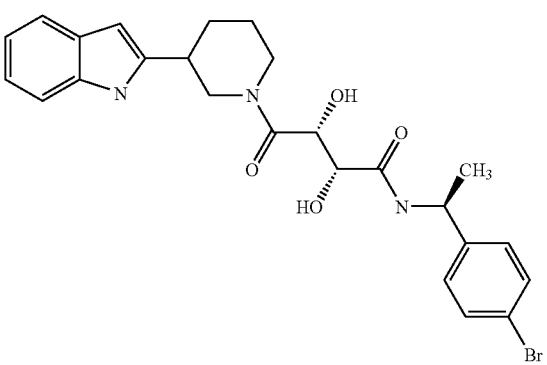 | 514.41 | 515.10 | 4.30 |

TABLE 2-continued

| S. No. | Structure | MWt | MS m/z (M + H) | Retention time (min) |
|---|---|---|---|---|
| 168 | 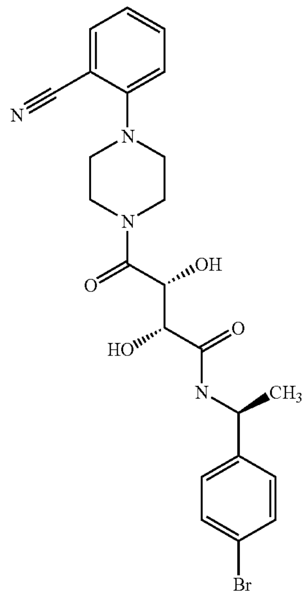 | 501.37 | 502.10 | 4.20 |
| 169 | 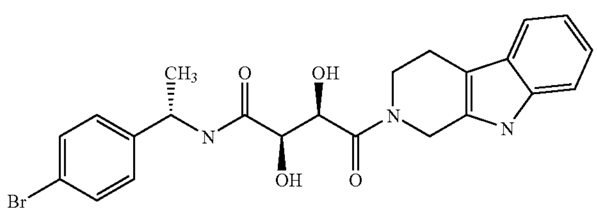 | 486.36 | 487.10 | 4.25 |
| 170 | 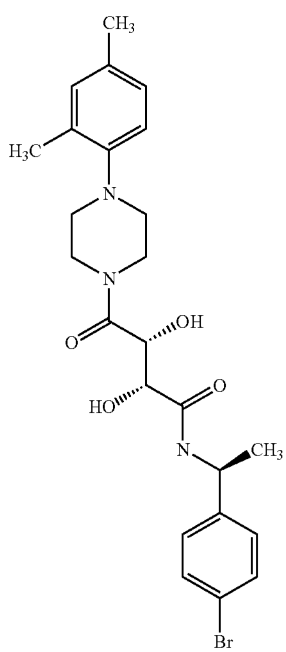 | 504.42 | 505.10 | 4.40 |

TABLE 2-continued

| S. No. | Structure | MWt | MS m/z (M + H) | Retention time (min) |
|---|---|---|---|---|
| 171 | 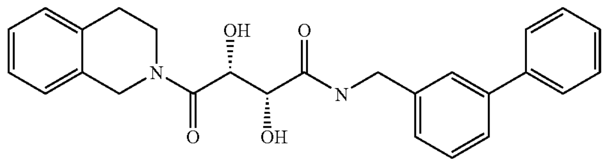 | 430.50 | 431.20 | 4.30 |
| 172 | 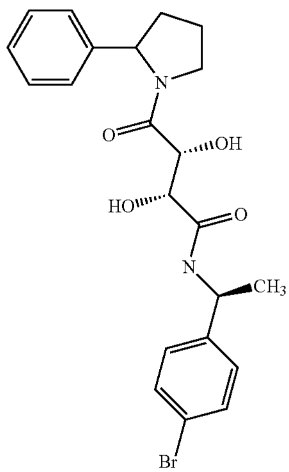 | 461.35 | 462.10 | 1.80 |
| 173 | 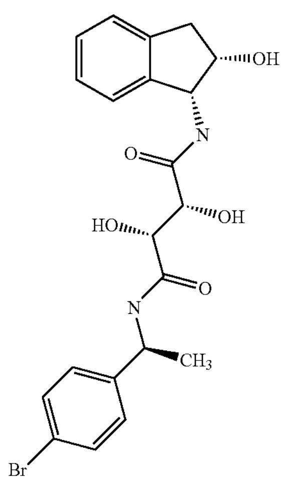 | 463.32 | 464.10 | 1.50 |

TABLE 2-continued

| S. No. | Structure | MWt | MS m/z (M + H) | Retention time (min) |
|---|---|---|---|---|
| 174 | 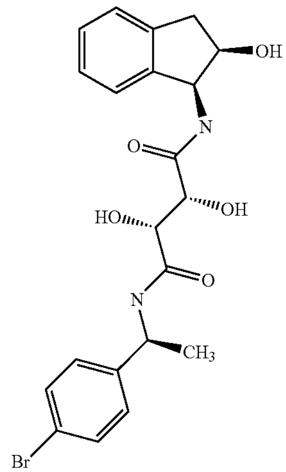 | 463.32 | 464.10 | 1.50 |
| 175 | 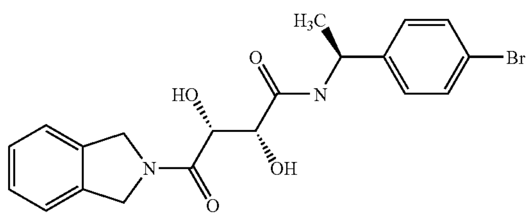 | 433.30 | 434.10 | 1.75 |
| 176 | 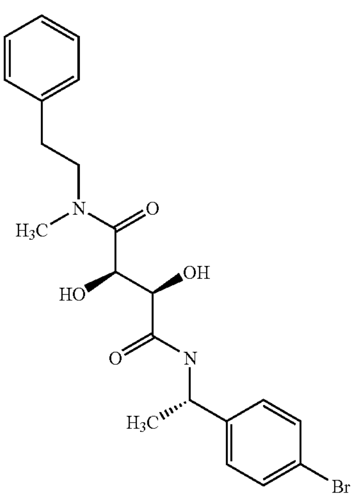 | 449.34 | 450.10 | 1.80 |
| 177 | 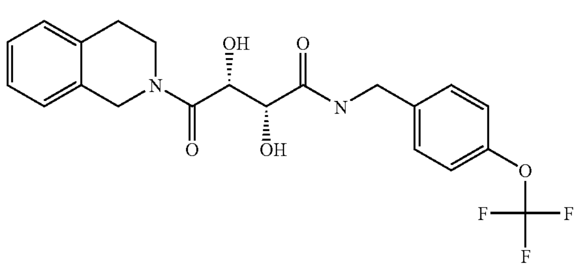 | 438.40 | 439.10 | 1.75 |

TABLE 2-continued

| S. No. | Structure | MWt | MS m/z (M + H) | Retention time (min) |
|---|---|---|---|---|
| 178 | 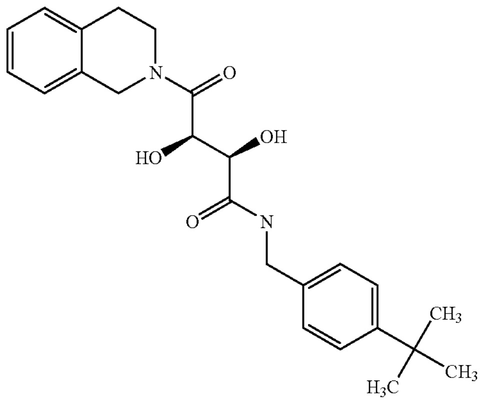 | 410.51 | 411.20 | 1.90 |
| 179 | 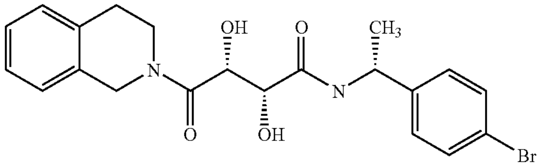 | 447.32 | 448.10 | 1.75 |
| 180 | 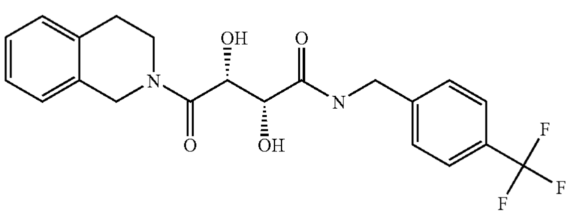 | 422.40 | 423.10 | 1.70 |
| 181 | 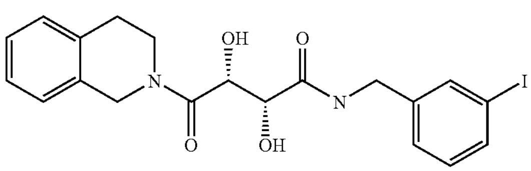 | 480.29 | 481.10 | 4.15 |
| 182 | 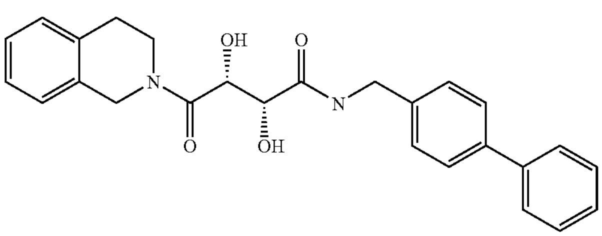 | 430.50 | 431.20 | 1.80 |
| 183 | 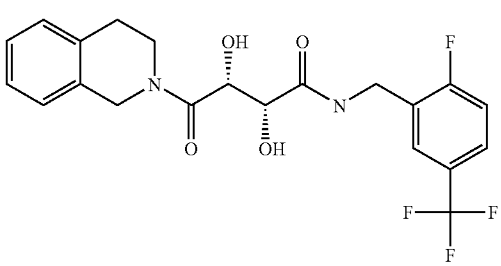 | 440.39 | 441.20 | 4.50 |

TABLE 2-continued

| S. No. | Structure | MWt | MS m/z (M + H) | Retention time (min) |
|---|---|---|---|---|
| 184 | 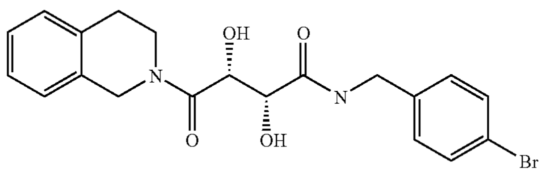 | 433.30 | 434.10 | 1.60 |
| 185 | 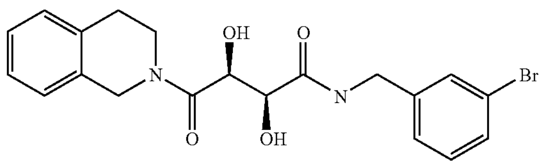 | 433.30 | 434.10 | 4.20 |
| 186 | 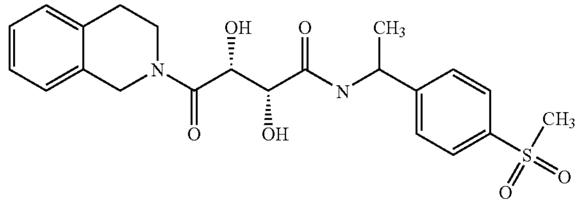 | 446.40 | 447.10 | 1.25 |
| 187 | 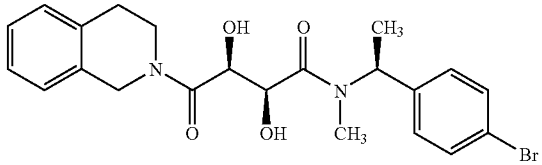 | 461.35 | 462.10 | 4.00 |
| 188 | 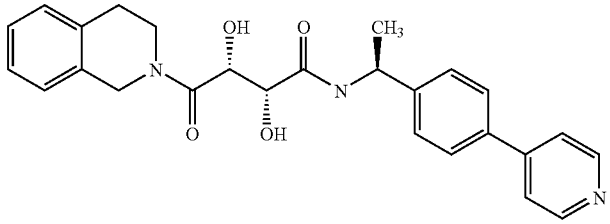 | 445.31 | 446.10 | 1.52 |
| 189 | 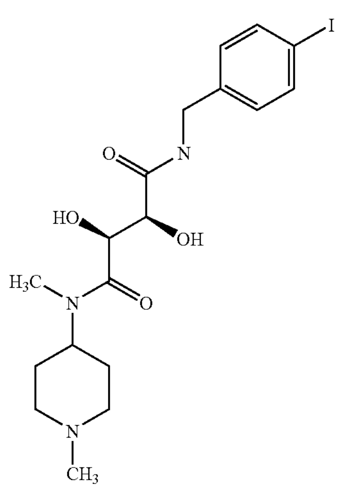 | 475.32 | 476.20 | 1.20 |

TABLE 2-continued

| S. No. | Structure | MWt | MS m/z (M + H) | Retention time (min) |
|---|---|---|---|---|
| 190 | 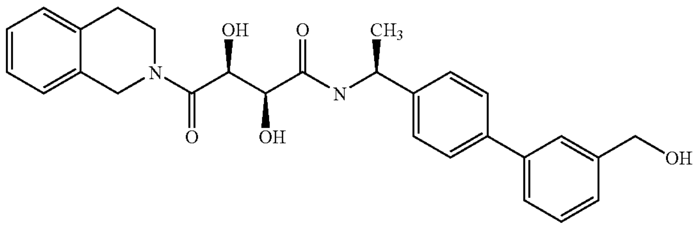 | 474.55 | 475.10 | 1.70 |
| 191 | 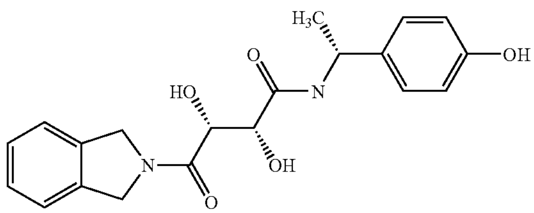 | 370.40 | 371.20 | 2.90 |
| 192 | 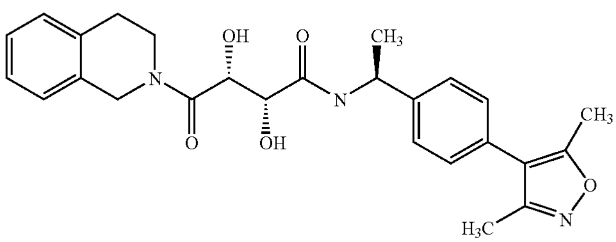 | 463.53 | 464.20 | 1.60 |
| 193 | 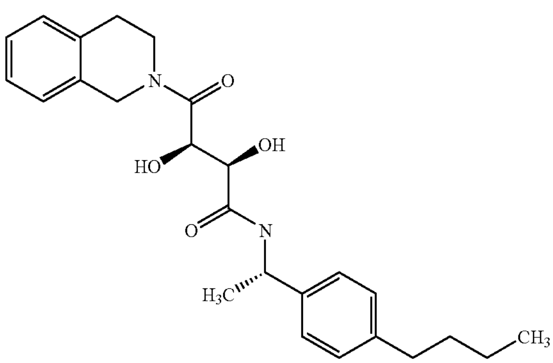 | 424.53 | 425.20 | 2.00 |
| 194 | 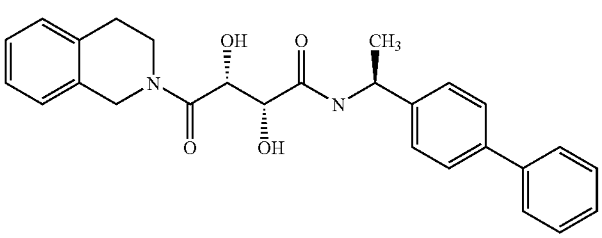 | 444.52 | 445.10 | 1.90 |
| 195 | 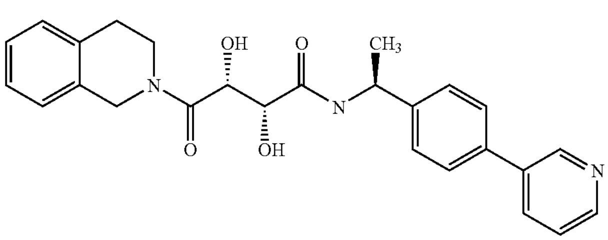 | 445.51 | 446.10 | 1.25 |

TABLE 2-continued

| S. No. | Structure | MWt | MS m/z (M + H) | Retention time (min) |
|---|---|---|---|---|
| 196 | 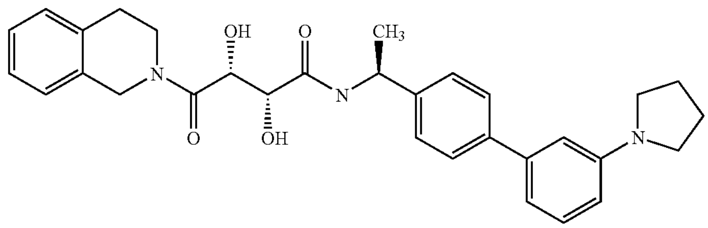 | 513.36 | 514.10 | 2.15 |
| 197 | 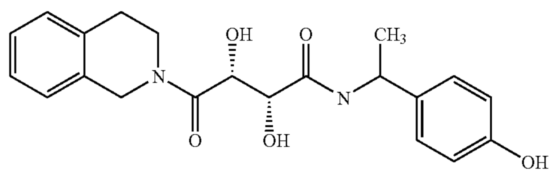 | 384.43 | 385.10 | 1.20 |
| 198 | 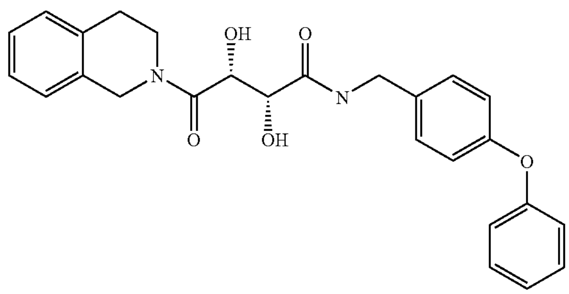 | 446.50 | 447.10 | 1.80 |
| 199 | 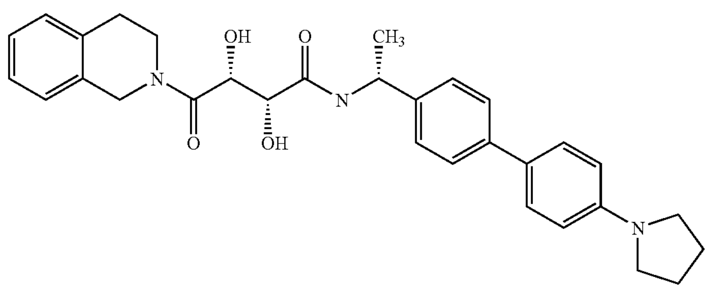 | 513.36 | 514.10 | 1.80 |
| 200 | 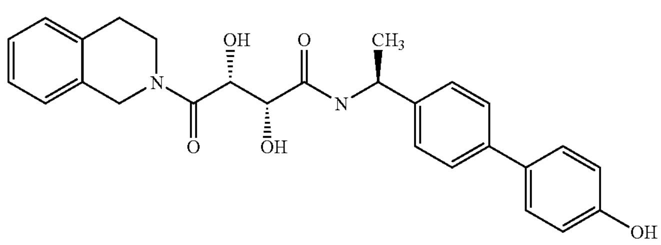 | 460.52 | 461.10 | 1.50 |
| 201 | 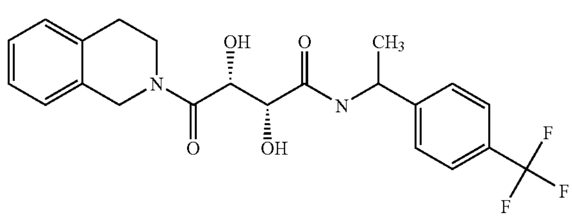 | 436.42 | 437.10 | 1.85 |

TABLE 2-continued

| S. No. | Structure | MWt | MS m/z (M + H) | Retention time (min) |
|---|---|---|---|---|
| 202 | 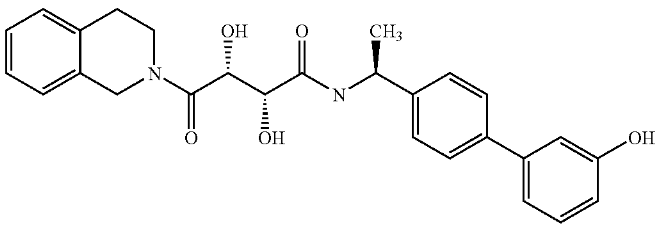 | 460.52 | 461.20 | 1.65 |
| 203 | 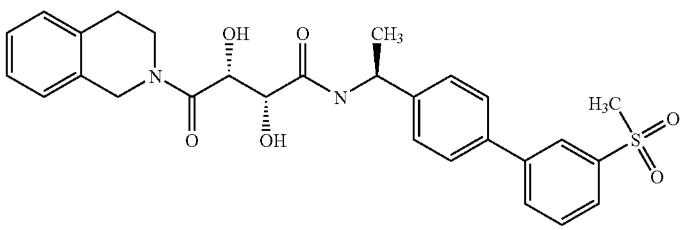 | 522.46 | 523.20 | 1.50 |
| 204 | 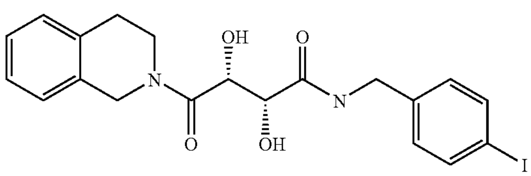 | 480.29 | 481.10 | 1.75 |
| 205 | 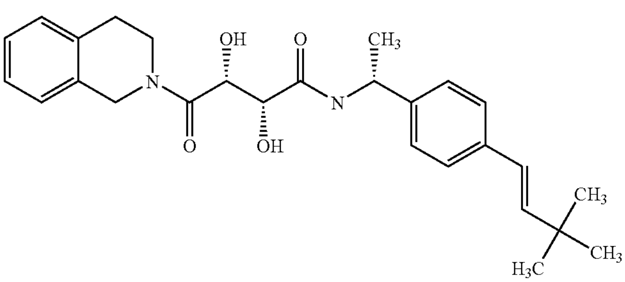 | 450.57 | 451.20 | 2.25 |
| 206 | 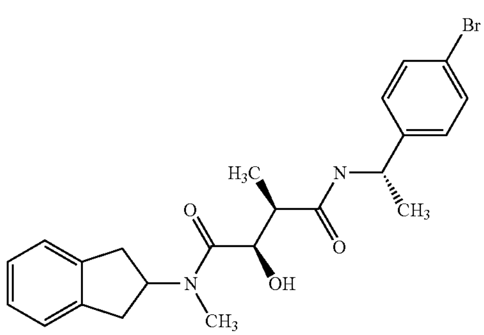 | 461.35 | 462.10 | 1.90 |
| 207 | 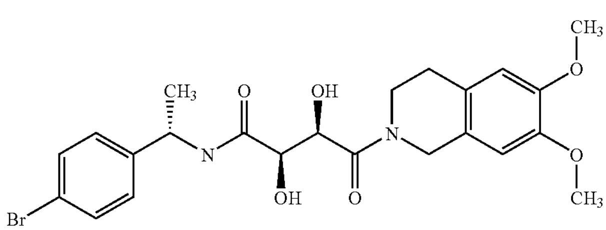 | 507.37 | 508.10 | 1.65 |

TABLE 2-continued

| S. No. | Structure | MWt | MS m/z (M + H) | Retention time (min) |
|---|---|---|---|---|
| 208 | 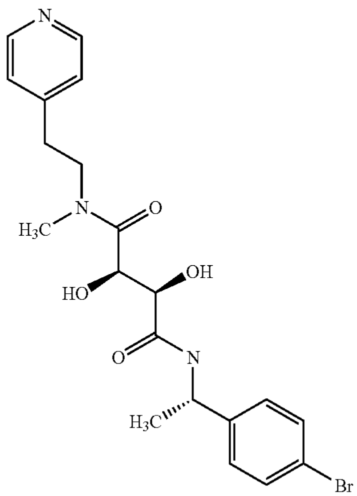 | 450.33 | 451.10 | 1.05 |
| 209 | 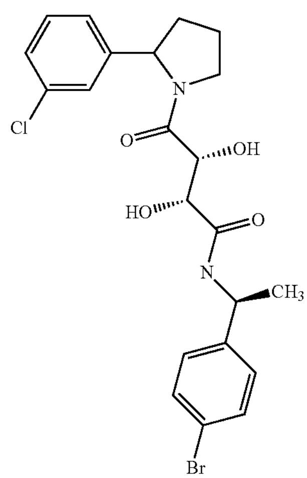 | 495.60 | 496.10 | 2.00 |
| 210 | 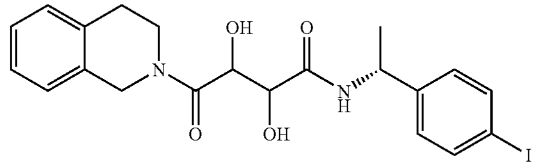 | 494.29 | 495.10 | 4.50 |
| 211 | 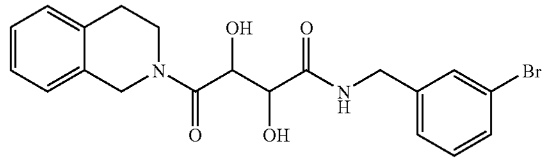 | 432.21 | 433.10 | 4.20 |
| 212 | 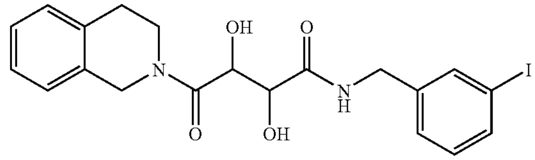 | 480.29 | 481.10 | 4.15 |

TABLE 2-continued

| S. No. | Structure | MWt | MS m/z (M + H) | Retention time (min) |
|---|---|---|---|---|
| 213 | 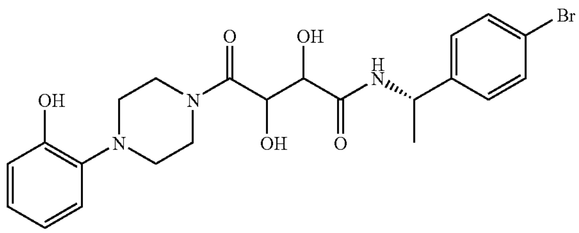 | 491.25 | 492.10 | 1.50 |
| 214 | 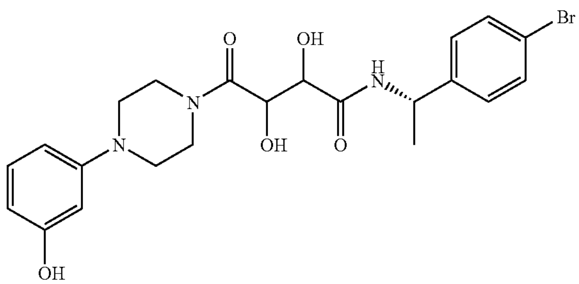 | 491.25 | 492.10 | 1.50 |
| 215 | 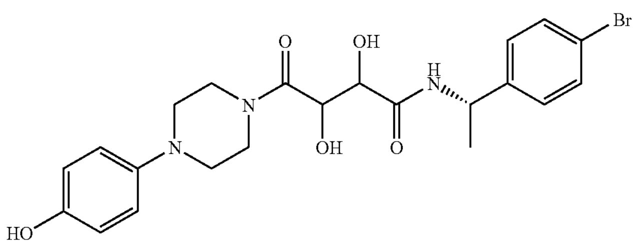 | 491.25 | 492.10 | 1.50 |
| 216 | 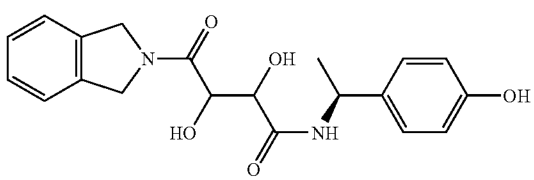 | 370.15 | 371.00 | 2.15 |
| 217 | 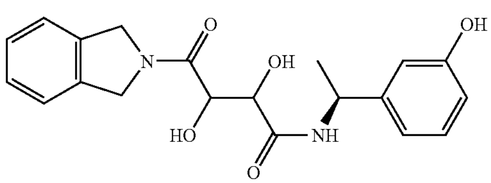 | 370.15 | 371.00 | 2.15 |
| 218 | 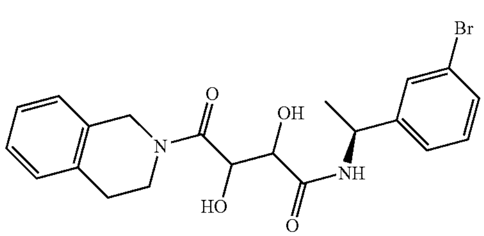 | 447.32 | 448.10 | 4.50 |

TABLE 2-continued
| S. No. | Structure | MWt | MS m/z (M + H) | Retention time (min) |
|---|---|---|---|---|
| 219 | 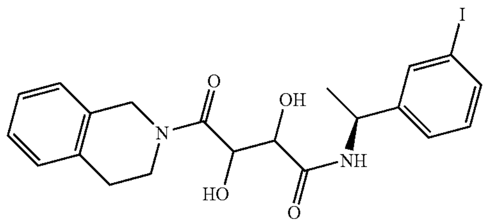 | 494.32 | 495.10 | 4.60 |
| 220 | 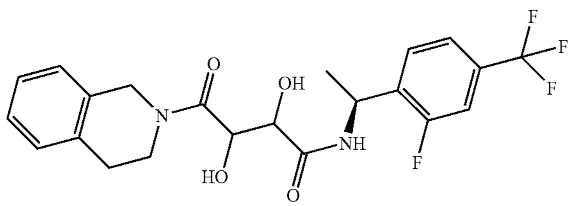 | 454.25 | 455.10 | 4.20 |
| 221 | 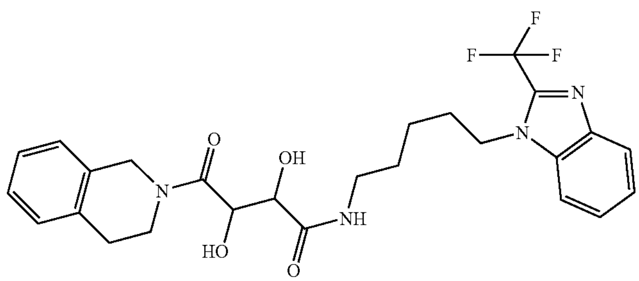 | 518.25 | 519.00 | 4.50 |
Example-5
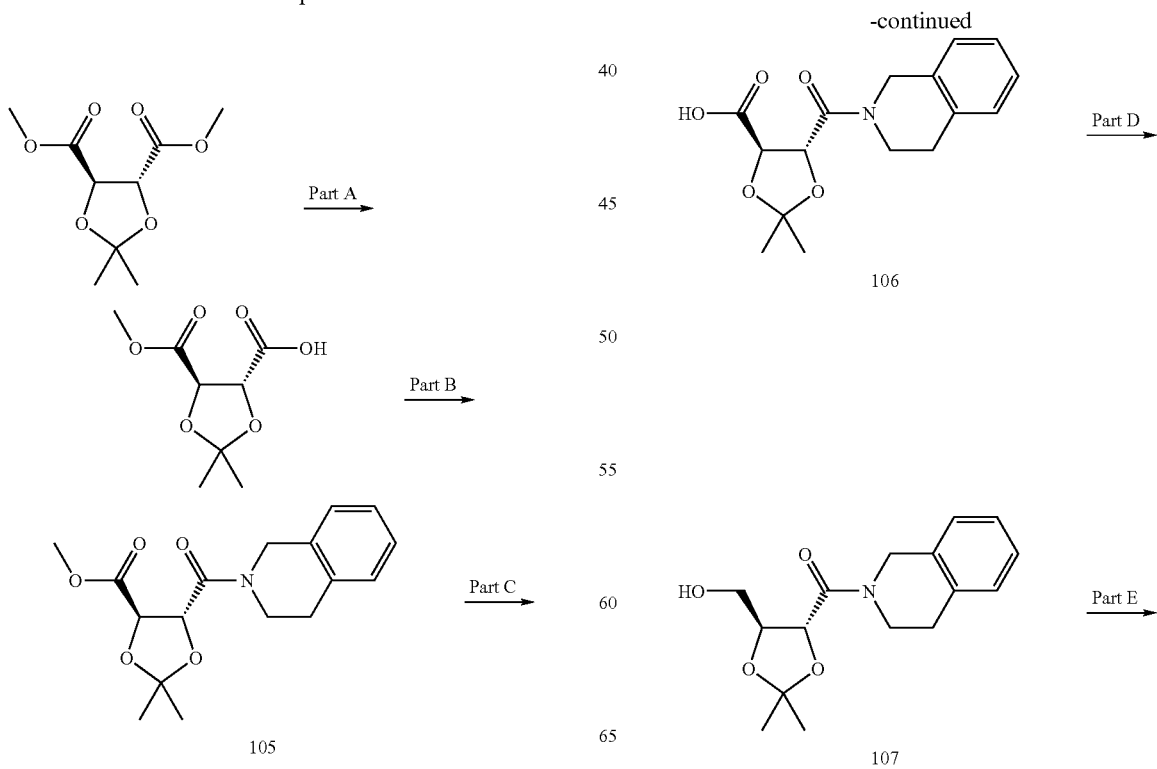

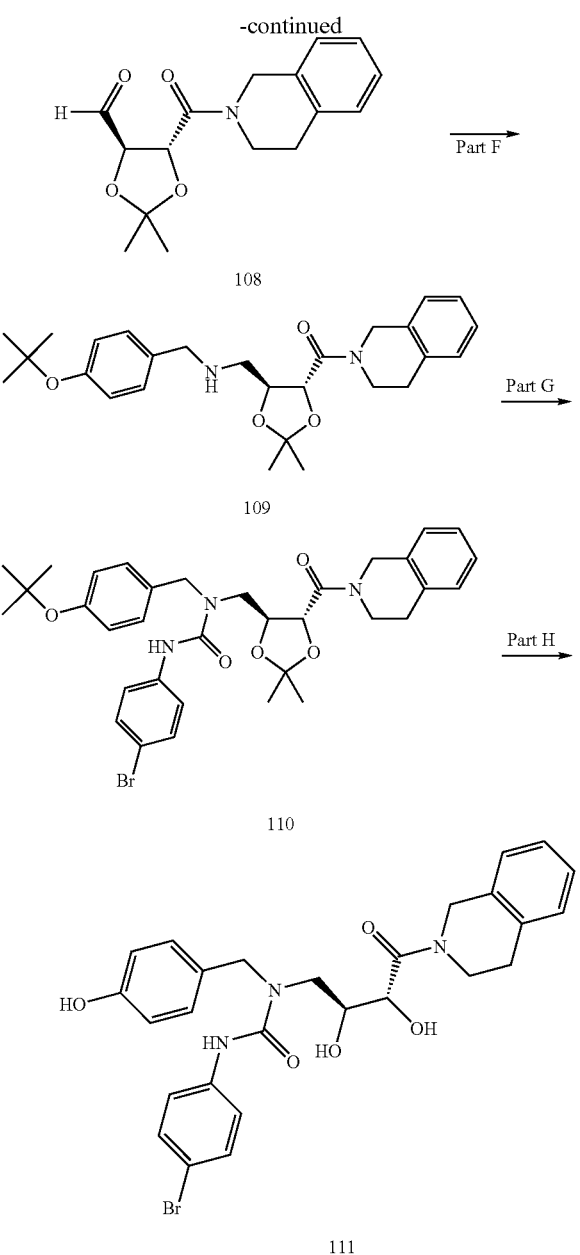

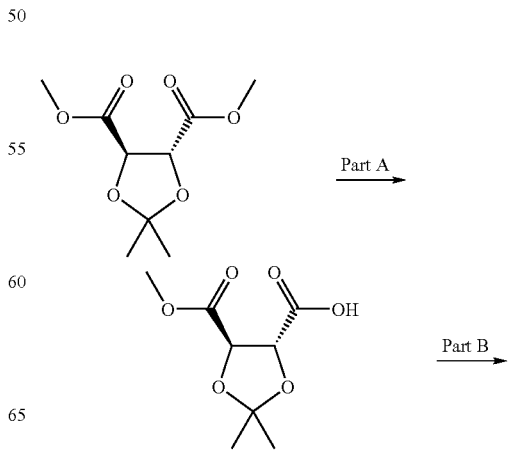

Part A, B (compound 105), and C (compound 106) are performed as described in Example 1.

Part D:

Compound 106 (1.0 gm) dissolved in dry THF and cooled to −40° C. and kept under nitrogen atmosphere. Two equivalents of BH$_3$ in THF(2.0 M) solution was added to it drop wise and the solution stirred at −40° C. for one hour followed by allowing the reaction mixture to warm to room temperature and continued stirring for overnight.

The solvent evaporated and extracted with ethyl acetate (200 m). The organic layer washed with water, brine, and dried over anhydrous MgSO$_4$. Filtered and concentrated to dryness to provide the product 107. Purified on silica column using eluants Hexane and Ethyl acetate (8:2)

Part E:

The compound 107 (250 mg) dissolved in dichloromethane and large excess (10 equivalents) of TEMPO resin was added to it. The reaction mixture stirred at room temperature for overnight. The LCMS analysis showed the completion. The mixture was filtered and the organic layer evaporated under vacuum. Compound 108 was used without further purification. HPLC-MS $t_R$=1.50 min (UV$_{254\ nm}$); mass calculated for formula C$_{16}$H$_{19}$NO$_4$, 289.33, observed LCMS m/z 290.1 (M+H).

Part F:

Compound 108 (145 mg, 0.5 mmol) and 4-ter-butoxy benzyl amine (0.6 mmol, 98 mg, 1.1 equivalents) were dissolved in dichloromethane and the solution was added with 100 uL of acetic acid, followed by addition of sodium triacetoxy borohydride (3 equivalents) and the solution was stirred at room temperature for overnight. The analysis showed the completion of the reaction. The reaction mixture was added with 200 mL of dichloromethane and washed with water, brine and DCM layer was dried over anhydrous MgSO$_4$, filtered and evaporated under vacuum to provide compound 109, which was purified on silica gel column using the eluants hexane-ethyl acetate. HPLC-MS $t_R$=2.75 min (UV$_{254\ nm}$); mass calculated for formula C$_{27}$H$_{36}$N$_2$O$_4$, 452.27, observed LCMS m/z 453.1 (M+H).

Part G:

Compound 109 (110 mg, 0.25 mmol) and 4-bromo isocyanate (0.3 mmol, 60 mg, 1.2 equivalents) were dissolved in dichloromethane and the solution was stirred at room temperature for overnight. The analysis showed the completion of the reaction. The reaction mixture was added with 100 mL of dichloromethane and washed with water, brine and DCM layer was dried over anhydrous MgSO$_4$, filtered and evaporated under vacuum to provide compound 110, which was purified on silica gel column using the eluants hexane-ethyl acetate. HPLC-MS $t_R$=3.25 min (UV$_{254\ nm}$); mass calculated for formula C$_{34}$H$_{40}$N$_3$O$_5$Br, 649.22, observed LCMS m/z 650.0 (M+H).

Part H:

Compound 110 (25 mg) was dissolved in dichloromethane(2 mL) and added 90% aqueous Trifluoroacetic acid and stirred at room temperature for 45 minutes. The solvent evaporated under vacuum and the resulting material purified on Prep HPLC to give the product 111. HPLC-MS $t_R$=1.80 min (UV$_{254\ nm}$); mass calculated for formula C$_{27}$H$_{28}$N$_3$O$_5$Br, 553.12, observed LCMS m/z 554.1 (M+H).

Example 6

-continued

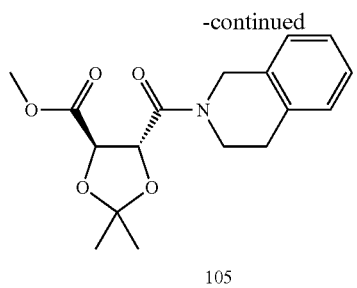

105

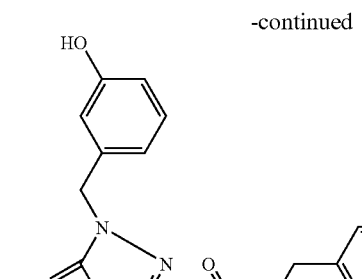

115

Part C →

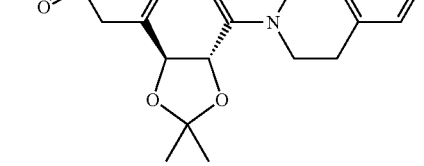

106

Part D →

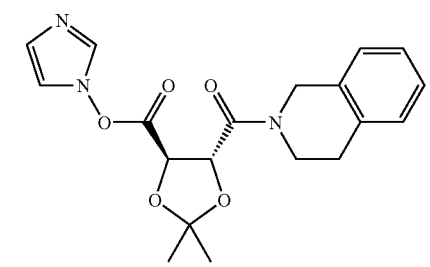

112

+

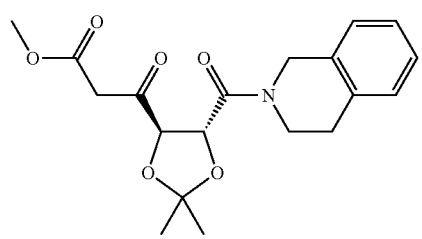

116

Part A, B, C can be prepared as described in Example 1 (parts a, b, c)

Part D:
Compound 106 (2 mmol, 610 mg) was dissolved in THF (50 mL) and cooled to 0° C. and kept under nitrogen atmosphere. To the above solution while stirring, a solution of N,N' carbonyldiimidazole (2.2 mmol, 356 mg) in THf was added and stirring continued for overnight. The removal of solvent provided the activated ester in quantitative yield and is used in the next step with out purification.
HPLC-MS $t_R$=3.25 min (UV$_{254\ nm}$); mass calculated for formula $C_{19}H_{21}N_3O_5$, 371.15, observed LCMS m/z 372.10 (M+H).

Part E:
Compound 113 generated in situ, [addition of dibutyl magnesium to ethyl hydrogen malonate in THF at −78° C. stirred at −78° C. for 1 hr] was added to a solution containing the compound 112 in THF and stirred at room temperature for 24 hrs. The solvent was evaporated and ethyl acetate (100 mL) added. Organic layer washed with water, brine, dried over anhydrous MgSO4, filtered and evaporated to give a gummy material, purified on silica gel column to afford compound 114. HPLC-MS $t_R$=1.95 min (UV$_{254\ nm}$); mass calculated for formula $C_{20}H_{25}NO_6$, 375.17, observed LCMS m/z 376.10 (M+H).

Part F:
Compound 114 (0.2 mmol, 75 mg) in ethanol (5 mL) was added with 3-hydroxybenzylhydrazide dihydrochloride (0.22 mmol, 50 mg) and triethyl amine (140 uL, 1 mmol, 5 equivalents) and refluxed overnight. The LCMS analysis showed the product formation. The ethanol was evaporated and compound was purified by Preparatory HPLC to afford the product 115. HPLC-MS $t_R$=1.50 min (UV$_{254\ nm}$); mass calculated for formula $C_{25}H_{27}N3O_5$, 449.17, observed LCMS m/z 450.10 (M+H).

Part G:

Compound 116 was prepared using the procedure described in Example 3 part B. HPLC-MS $t_R$=1.40 min (UV$_{254\ nm}$); mass calculated for formula $C_{25}H_{27}N3O_5$, 409.16, observed LCMS m/z 410.10 (M+H).

Example 7

Compound 117

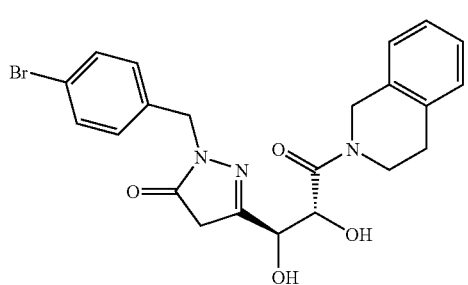

Compound 117 was synthesized similar to the procedure described in the synthesis of compound 116, Example 6 (Part A-F)

HPLC-MS $t_R$=1.40 min (UV$_{254\ nm}$); mass calculated for formula $C_{22}H_{22}BrN_3O_4$, 471.08, observed LCMS m/z 472.00 (M+H).

Example 8

Compound 119:

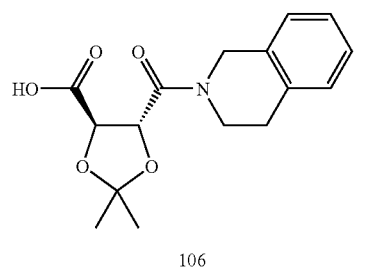

106

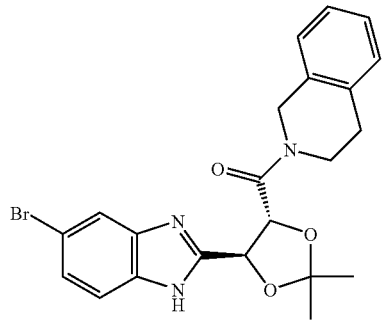

118

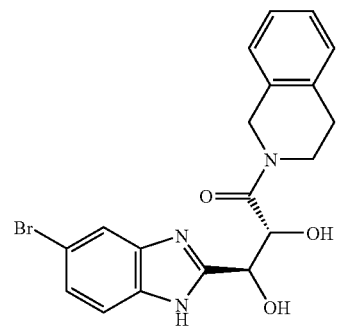

119

Part A:

Compound 106 made as described in example 6, Compound 106 (305 mg. 1 mmol) was dissolved in dimethylformamide and HATU (408 mg, 1.1 mmol), diisopropylethylamine amine (525 uL, 3 mmol) were added and stirred at room temperature. After ten minutes, 4-bromo o-phenylene diamine was added to the reaction mixture and stirring continued for overnight. LCMS analysis showed the completion of the reaction. Reaction mixtured diluted.

Example 9

Compound 121

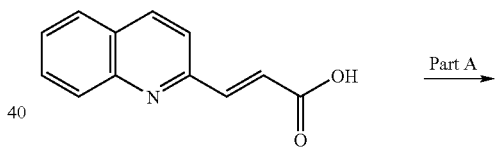

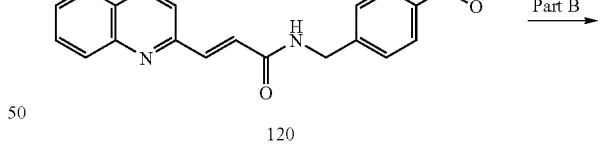

120

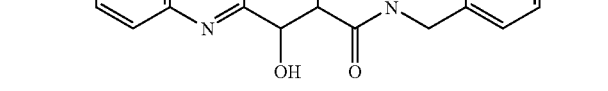

121 compound 120:

3-Quinolin-2-yl-acrylic acid (400 mg, 2 mmol) is dissolved in dimethylformamide and HATU (800 mg, 2.2 mmol) and diisopropylethylamine(1.2 ml, 6 mmol), was added to it and stirred at room temperature. To this solution, 4-methyl sulfonyl benzyl amine hydrochloride is added and stirring continued for 4 hrs. The reaction mixture diluted with ethyl acetate and washed with water, brine and dried over anhydrous MgSO$_4$, Filtered and evaporation of the organic solvent provide the product 120.

Compound 121:

Compound 120 (185 mg, 0.5 mmol) was dissolved in dichloromethane and osmium tetroxide (254 mg, 1 mmol) is added to it and stirred the mixture for overnight. LC analysis indicate the product formation. Evaporation of sovent and purification of the product by passing through the silica gel column followed by preprative HPLC result in the product 121.

Example 10

The compound listed in the table below can be prepared from the procedures described in experimental 2A or 2C utilizing Sonogashira coupling followed by coupling with compound 5 or 7 with HATU and hydrolysis as described in example 3 A and B.

| S. NO. | Structure | MWt | MS m/z (M + H) |
|---|---|---|---|
| 122 | 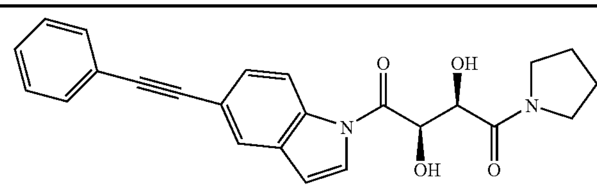 | 402.16 | 403.10 |
| 123 | 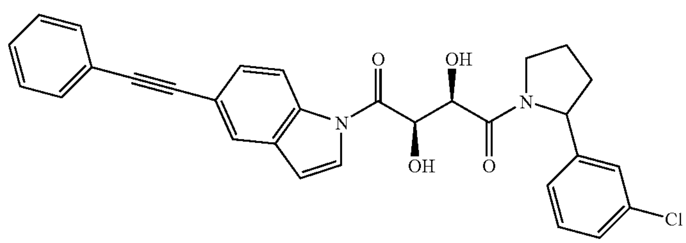 | 512.15 | 513.10 |
| 124 | 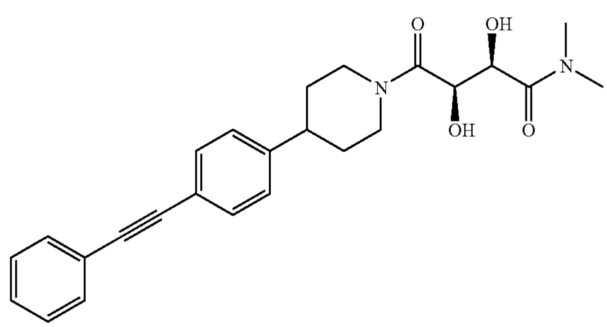 | 420.20 | 421.10 |
| 125 | 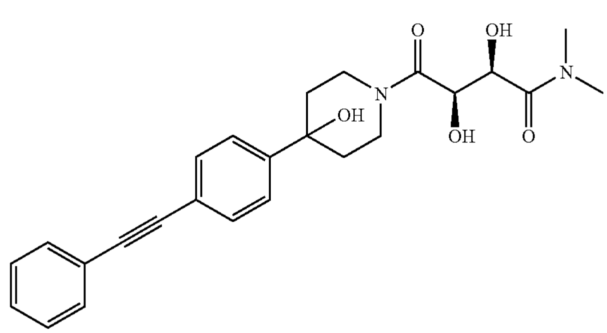 | 436.20 | 437.10 |

-continued
| S. NO. | Structure | MWt | MS m/z (M + H) |
|---|---|---|---|
| 126 | 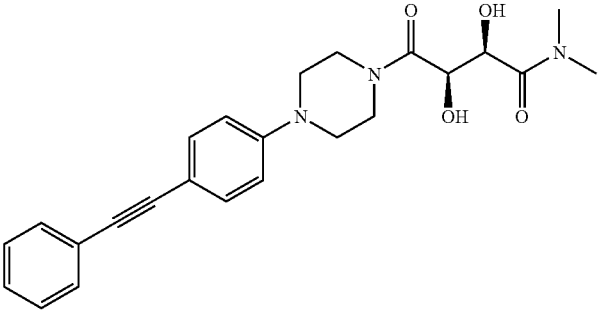 | 421.20 | 422.10 |
| 127 | 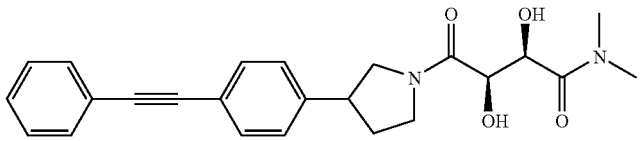 | 406.19 | 407.20 |
| 128 | 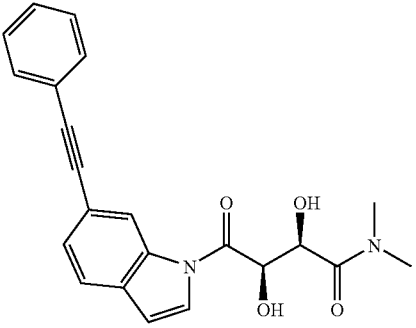 | 376.14 | 377.10 |
| 129 | 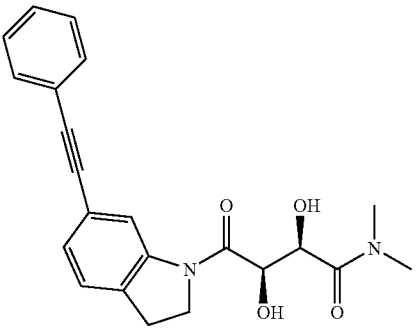 | 378.16 | 379.10 |
| 130 | 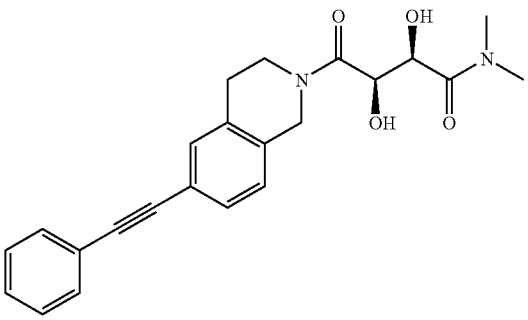 | 392.17 | 393.10 |

| S. NO. | Structure | MWt | MS m/z (M + H) |
|---|---|---|---|
| 131 | 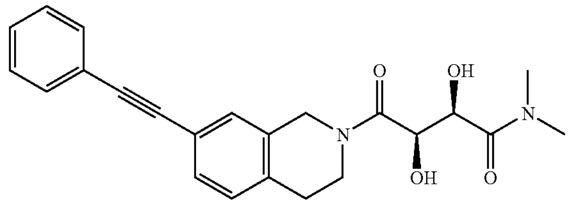 | 392.17 | 393.10 |
| | and | | |
| 132 | 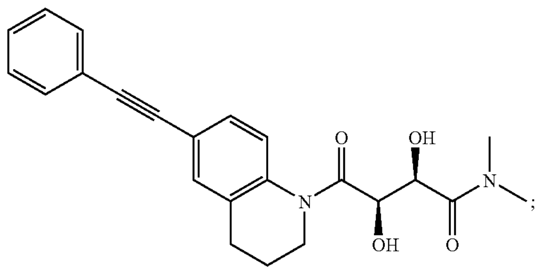 | 392.17 | 393.10 |

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

Each and every document referred to in this patent application is incorporated herein by reference in its entirety for all purposes.

What is claimed is:

1. A compound of formula (I)

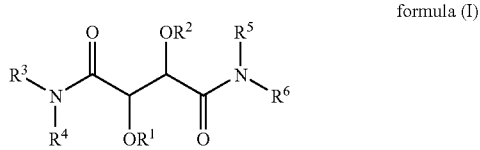

or a pharmaceutically acceptable salt thereof, wherein:
(i) each of $R^1$ and $R^2$ independently is hydrogen or alkyl;
(ii) $R^3$ and $R^4$ taken together with the nitrogen to which they shown attached is benzopyrrolyl;
   wherein said benzopyrrolyl is substituted with one or two substituents, each substituent being independently selected from the group consisting of aryl and alkynyl;
   wherein said aryl substituent is unsubstituted or is optionally substituted with one or two moieties selected independently from the group consisting of perhaloalkyl, halo, alkyl, alkoxy, cyano, perhaloalkoxy, and alkynyl moiety, wherein said alkynyl moiety is substituted with an aryl radical;
   wherein said alkynyl substituent is substituted with an aryl moiety, wherein said aryl moiety is unsubstituted or optionally substituted with one to three radicals selected from the group consisting of perhaloalkyl, halo, alkyl, alkoxy, cyano, and perhaloalkoxy; and
(iii) $R^5$ and $R^6$ taken together with the nitrogen to which they shown attached is pyrrolodinyl;
   wherein said pyrrolodinyl is unsubstituted or substituted with an aryl substituent;
   wherein said aryl substituent is unsubstituted or substituted with one to three moieties independently selected from the group consisting of perhaloalkyl, halo, alkyl, alkoxy, cyano, and perhaloalkoxy.

2. The compound of claim 1, wherein $R^1$ and $R^2$ are both hydrogen.

3. The compound according to claim 1, wherein:
the aryl substituent of the benzopyrrolyl is substituted with an alkynyl moiety, wherein said alkynyl moiety is substituted with an aryl radical; and
the alkynyl substituent of the benzopyrrolyl comprising $R^3$ and $R^4$ is substituted with an aryl moiety.

4. The compound according to claim 3, wherein the aryl substituent of the benzopyrrolyl is phenyl.

5. The compound according to claim 3, wherein the aryl radical of the alkynyl moiety is phenyl.

6. The compound according to claim 1, wherein said pyrrolodinyl is unsubstituted.

7. The compound according to claim 1, wherein said pyrrolodinyl is substituted with an aryl substituent, wherein said aryl substituent is substituted with a halo moiety.

8. The compound according to claim 7, wherein said aryl substituent is phenyl.

9. The compound according to claim 1, wherein said aryl substituent of said benzopyrrollyl is unsubstituted or substituted with perhaloalkyl.

10. The compound according to claim 9, wherein said aryl substituent is phenyl.

11. A compound selected from the group consisting of:

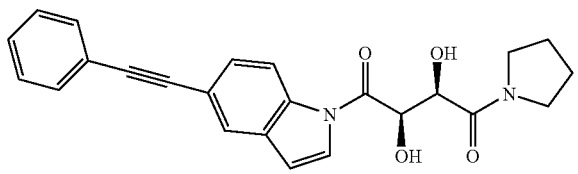

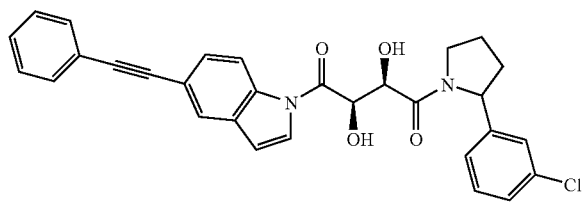

and

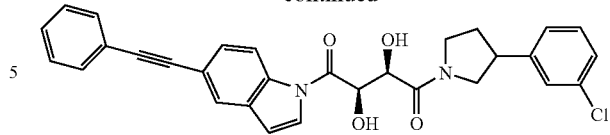

or a pharmaceutically acceptable salt thereof.

12. A pharmaceutical composition comprising as an active ingredient at least one compound of claim 1, or a pharmaceutically acceptable salt thereof.

13. The pharmaceutical composition of claim 12 additionally comprising at least one pharmaceutically acceptable carrier.

14. A method of treating a condition or disease selected from the group consisting of rheumatoid arthritis, osteoarthritis, periodontitis, gingivitis, corneal ulceration, neovascular glaucoma, inflammatory bowel disease, multiple sclerosis and psoriasis in a subject, comprising: administering to the subject in need of such treatment a therapeutically effective amount of at least one compound of claim 1, or a pharmaceutically acceptable salt thereof.

* * * * *